(12) United States Patent
Ye et al.

(10) Patent No.: US 8,574,576 B2
(45) Date of Patent: Nov. 5, 2013

(54) HUMANIZED ANTI-EGFL7 ANTIBODIES AND METHODS USING SAME

(71) Applicant: Genentech, Inc., South San Francisco, CA (US)

(72) Inventors: Weilan Ye, Foster City, CA (US); Mark S. Dennis, San Carlos, CA (US); Jill Fredrickson, Sunnyvale, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/668,129

(22) Filed: Nov. 2, 2012

(65) Prior Publication Data

US 2013/0064822 A1    Mar. 14, 2013

Related U.S. Application Data

(62) Division of application No. 12/776,259, filed on May 7, 2010, now Pat. No. 8,404,811.

(60) Provisional application No. 61/176,817, filed on May 8, 2009.

(51) Int. Cl.
*A61K 39/395*    (2006.01)

(52) U.S. Cl.
USPC .................................... 424/133.1; 530/387.1

(58) Field of Classification Search
None
See application file for complete search history.

(56) References Cited

U.S. PATENT DOCUMENTS

| | | | |
|---|---|---|---|
| 6,217,895 B1 | 4/2001 | Guo et al. |
| 6,582,959 B2 | 6/2003 | Kim |
| 6,703,020 B1 | 3/2004 | Thorpe et al. |
| 6,820,632 B2 | 11/2004 | Ohmi et al. |
| 6,884,879 B1 | 4/2005 | Baca et al. |
| 6,916,648 B2 | 7/2005 | Goddard et al. |
| 6,962,797 B2 | 11/2005 | Goddard et al. |
| 6,972,325 B2 | 12/2005 | Fong et al. |
| 6,974,696 B2 | 12/2005 | Botstein et al. |
| 7,019,115 B2 | 3/2006 | Desnoyers et al. |
| 7,019,124 B2 | 3/2006 | Desnoyers et al. |
| 7,029,874 B2 | 4/2006 | Baker et al. |
| 7,037,710 B2 | 5/2006 | Goddard et al. |
| 7,067,636 B2 | 6/2006 | Desnoyers et al. |
| 7,074,593 B2 | 7/2006 | Goddard et al. |
| 7,084,258 B2 | 8/2006 | Desnoyers et al. |
| 7,087,428 B2 | 8/2006 | Goddard et al. |
| 7,105,335 B2 | 9/2006 | Goddard et al. |
| 7,105,640 B2 | 9/2006 | Desnoyers et al. |
| 7,109,305 B2 | 9/2006 | Baker et al. |
| 7,112,657 B2 | 9/2006 | Goddard et al. |
| 7,115,415 B2 | 10/2006 | Goddard et al. |
| 7,132,283 B2 | 11/2006 | Fong et al. |
| 7,135,334 B2 | 11/2006 | Goddard et al. |
| 7,164,007 B2 | 1/2007 | Goddard et al. |
| 7,164,009 B2 | 1/2007 | Goddard et al. |
| 7,166,700 B2 | 1/2007 | Goddard et al. |
| 7,169,912 B2 | 1/2007 | Desnoyers et al. |
| 7,189,529 B2 | 3/2007 | Desnoyers et al. |
| 7,192,589 B2 | 3/2007 | Ashkenazi et al. |
| 7,193,049 B2 | 3/2007 | Desnoyers et al. |
| 7,193,050 B2 | 3/2007 | Baker et al. |
| 7,195,760 B2 | 3/2007 | Desnoyers et al. |
| 7,196,165 B2 | 3/2007 | Ashkenazi et al. |
| 7,196,176 B2 | 3/2007 | Goddard et al. |
| 7,202,335 B2 | 4/2007 | Goddard et al. |
| 7,202,338 B2 | 4/2007 | Goddard et al. |
| 7,208,575 B2 | 4/2007 | Desnoyers et al. |
| 7,214,656 B2 | 5/2007 | Desnoyers et al. |
| 7,220,835 B2 | 5/2007 | Baker et al. |
| 7,232,889 B2 | 6/2007 | Goddard et al. |
| 7,250,495 B2 | 7/2007 | Goddard et al. |
| 7,265,210 B2 | 9/2007 | Goddard et al. |
| 7,279,553 B2 | 10/2007 | Goddard et al. |
| 7,285,623 B2 | 10/2007 | Gao et al. |
| 7,294,700 B2 | 11/2007 | Goddard et al. |
| 7,368,250 B2 | 5/2008 | Goddard et al. |
| 7,371,836 B2 | 5/2008 | Desnoyers et al. |
| 7,419,663 B2 | 9/2008 | Ashkenazi et al. |
| 7,495,083 B2 | 2/2009 | Goddard et al. |
| 7,514,538 B2 | 4/2009 | Goddard et al. |
| 7,589,172 B2 | 9/2009 | Goddard et al. |
| 7,741,056 B2 | 6/2010 | Ashkenazi et al. |
| 7,771,719 B1 | 8/2010 | Filvaroff et al. |
| 8,007,798 B2 | 8/2011 | Ashkenazi et al. |
| 8,034,342 B2 | 10/2011 | Chen et al. |
| 8,088,386 B2 | 1/2012 | Ashkenazi et al. |
| 2003/0113798 A1 | 6/2003 | Burmer et al. |
| 2003/0166907 A1 | 9/2003 | Sheppard et al. |
| 2003/0190317 A1 | 10/2003 | Baca et al. |
| 2003/0203409 A1 | 10/2003 | Kim |
| 2003/0206899 A1 | 11/2003 | Ferrara et al. |
| 2003/0224984 A1 | 12/2003 | Baker et al. |
| 2004/0043927 A1 | 3/2004 | Baker et al. |
| 2005/0112126 A1 | 5/2005 | Baca et al. |

(Continued)

FOREIGN PATENT DOCUMENTS

DE    19817946    10/1999
EP    0666868    8/1995

(Continued)

OTHER PUBLICATIONS

Lee et al., "High-affinity human antibodies from phage-displayed synthetic fab libraries with a single framework scaffold", *Journal of Molecular Biology*, 340:1073-1093 (2004).

(Continued)

*Primary Examiner* — Laura B Goddard
*Assistant Examiner* — Meera Natarajan
(74) *Attorney, Agent, or Firm* — Clark & Elbing LLP; Karen L. Elbing

(57) ABSTRACT

The present invention concerns antibodies to EGFL7 and the uses of same.

30 Claims, 31 Drawing Sheets

(56) References Cited

U.S. PATENT DOCUMENTS

| | | | |
|---|---|---|---|
| 2007/0020735 | A1 | 1/2007 | Chen et al. |
| 2007/0031437 | A1 | 2/2007 | Filvaroff et al. |
| 2007/0160585 | A1 | 7/2007 | Fujinaga et al. |
| 2008/0160021 | A1 | 7/2008 | Chen et al. |
| 2008/0292619 | A1 | 11/2008 | Sehara et al. |
| 2009/0297512 | A1 | 12/2009 | Filvaroff et al. |
| 2010/0203041 | A1 | 8/2010 | Ye et al. |
| 2011/0200602 | A1 | 8/2011 | Ye et al. |
| 2012/0003208 | A1 | 1/2012 | Filvaroff et al. |
| 2012/0058909 | A1 | 3/2012 | Chen et al. |
| 2012/0064073 | A1 | 3/2012 | Chen et al. |
| 2012/0189626 | A1 | 7/2012 | Ashkenazi et al. |

FOREIGN PATENT DOCUMENTS

| | | | |
|---|---|---|---|
| JP | 2002-539263 | | 11/2002 |
| JP | 2006-507813 | | 3/2006 |
| KR | 20080099328 | A | 11/2008 |
| WO | WO 94/10202 | | 5/1994 |
| WO | WO 96/30046 | | 10/1996 |
| WO | WO 98/45332 | | 10/1998 |
| WO | WO 98/57983 | | 12/1998 |
| WO | WO 99/46281 | | 9/1999 |
| WO | WO 99/54353 | | 10/1999 |
| WO | WO 99/54437 | | 10/1999 |
| WO | WO 00/34477 | | 6/2000 |
| WO | WO 00/53752 | | 9/2000 |
| WO | WO 00/53756 | | 9/2000 |
| WO | WO 00/56340 | | 9/2000 |
| WO | WO 00/58473 | | 10/2000 |
| WO | WO 01/02563 | | 1/2001 |
| WO | WO 01/54477 | | 8/2001 |
| WO | WO 02/00690 | | 1/2002 |
| WO | WO 02/08284 | | 1/2002 |
| WO | WO 02/28888 | | 4/2002 |
| WO | WO-03/048902 | A2 | 6/2003 |
| WO | WO 2004/033630 | | 4/2004 |
| WO | WO 2004/076482 | | 9/2004 |
| WO | WO 2005/012359 | | 2/2005 |
| WO | WO 2005/044853 | | 5/2005 |
| WO | WO-2005/080432 | A2 | 9/2005 |
| WO | WO 2005/094846 | | 10/2005 |
| WO | WO-2005/117968 | A2 | 12/2005 |
| WO | WO 2006/013904 | | 2/2006 |
| WO | WO-2006/066171 | A1 | 6/2006 |
| WO | WO 2007/106915 | | 9/2007 |
| WO | WO-2007/106915 | A2 | 9/2007 |
| WO | WO2007106915 | * | 9/2007 |
| WO | WO-2008/076560 | A2 | 6/2008 |
| WO | WO-2008/129124 | A1 | 10/2008 |
| WO | WO-2009/012268 | A1 | 1/2009 |
| WO | WO-2009/012394 | A1 | 1/2009 |
| WO | WO-2009/042746 | A1 | 4/2009 |
| WO | WO 2009/073160 | | 6/2009 |
| WO | WO 2009/091810 | | 7/2009 |
| WO | WO-2009/149185 | A2 | 12/2009 |

OTHER PUBLICATIONS

Office Action for Japanese Patent Application No. 2012-510022, dated Nov. 20, 2012.

Parker et al., "The endothelial-cell-derived secreted factor Egfl7 regulates vascular tube formation," *Nature* 428: 754-758 (2004).

Office Action for Japanese Patent Application No. 2012-510022, dated Apr. 2, 2013.

Office Action for Taiwanese Patent Application No. 099114730, dated Dec. 21, 2012.

Office Action for Ukrainian Patent Application No. 201114544, dated Feb. 26, 2013.

Adamis et al., "Inhibition of vascular endothelial growth factor prevents retinal ischemia-associated iris neovascularization in a nonhuman primate," *Arch. Ophthalmol.* 114: 66-71 (1996).

Aiello et al., "Vascular endothelial growth factor in ocular fluid of patients with diabetic retinopathy and other retinal disorders," *N. Engl. J. Med.* 331: 1480-1487 (1994).

Auerbach et al., "Angiogenesis assays: a critical overview," *Clin. Chem.* 49: 32-40 (2003).

Caetano et al., "Expression and purification of recombinant vascular endothelial-statin," *Protein Expr. Purif.* 46: 136-142 (2006).

Cameron et al., "Therapeutic Electromagnetic Field (TEMF) and gamma irradiation on human breast cancer xenograft growth, angiogenesis and metastasis," *Cancer Cell Int.* 5: 23 (2005).

Campagnolo et al., "EGFL7 is a chemoattractant for endothelial cells and is up-regulated in angiogenesis and arterial injury," *Am. J. Pathol.* 167: 275-284 (2005).

Campbell, *Monoclonal Antibody Technology: The Production and Characterization of Rodent and Human Hybridomas*, Elsevier Science Ltd, pp. 1-32 (1984).

Casset et al., "A peptide mimetic of an anti-CD4 monoclonal antibody by rational design," *Biochem. Biophys. Res. Commun.* 307: 198-205 (2003).

De Pascalis et al., "Grafting of "abbreviated" complementarity-determining regions containing specificity-determining residues essential for ligand contact to engineer a less immunogenic humanized monoclonal antibody," *J. Immunol.* 169: 3076-3084 (2002).

Ferrara et al., "The biology of vascular endothelial growth factor," *Endocr. Rev.* 18: 4-25 (1997).

Finkle et al., "HER2-targeted therapy reduces incidence and progression of midlife mammary tumors in female murine mammary tumor virus huHER2-transgenic mice," *Clin. Cancer Res.* 10: 2499-2511 (2004).

Fitch et al., "Egfl7, a novel epidermal growth factor-domain gene expressed in endothelial cells," *Dev. Dyn.* 230: 316-324 (2004).

Folkman et al., "Induction of angiogenesis during the transition from hyperplasia to neoplasia," *Nature* 339: 58-61 (1989).

Folkman et al., "Angiogenesis," *J. Biol. Chem.* 267: 10931-10934 (1992).

Folkman, "Angiogenesis in cancer, vascular, rheumatoid and other disease," *Nat. Med.* 1: 27-31 (1995).

Gaudreault et al., "Preclinical Pharmacokinetics of Ranibizumab (rhuFabV2) After a Single Intravitreal Administration," *Invest. Ophthalmol. Vis. Sci.* 46: 726-733 (2005).

Hanahan, "Signaling vascular morphogenesis and maintenance," *Science* 277: 48-50 (1997).

Harlow & Lane, *Antibodies, A Laboratory Manual*, Cold Spring Harbor Laboratory Press, pp. 72-76 (1988).

Hogan et al., "Organogenesis: molecular mechanisms of tubulogenesis," *Nat. Rev. Genet.* 3: 513-523 (2002).

Hoogenboom, "Selecting and Screening Recombinant Antibody Libraries," *Nat. Biotechnol.* 23:1105-1116 (2005).

Horak et al., "Angiogenesis, assessed by platelet/endothelial cell adhesion molecule antibodies, as indicator of node metastases and survival in breast cancer," *Lancet* 340: 1120-1124 (1992).

iHOP (information hyperlinked over proteins), "EGFL7" printed Mar. 6, 2012 (3 pages).

Ishida et al., "Age-Related Macular Degeneration: Basic Research and Clinical Practice," *Igaku no Ayumi* [*A Walk in Medicine*] 211: 956-961 (2004) (In Japanese).

Kim et al., "Inhibition of vascular endothelial growth factor-induced angiogenesis suppresses tumour growth in vivo," *Nature* 362: 841-844 (1993).

Klagsbrun et al., "Regulators of angiogenesis," *Annu. Rev. Physiol.* 53: 217-239 (1991).

Lee et al., "Response of non-small cell lung cancer cells to the inhibitors of phosphatidylinositol 3-kinase/Akt- and MAPK kinase 4/c-Jun NH2-terminal kinase pathways: an effective therapeutic strategy for lung cancer," *Clin. Cancer Res.* 11: 6065-6074 (2005).

Lopez et al., "Transdifferentiated retinal pigment epithelial cells are immunoreactive for vascular endothelial growth factor in surgically excised age-related macular degeneration-related choroidal neovascular membranes," *Invest. Ophthalmol. Vis. Sci.* 37: 855-868 (1996).

Lubarsky et al., "Tube morphogenesis: making and shaping biological tubes," *Cell* 112: 19-28 (2003).

MacCallum et al., "Antibody-antigen interactions: contact analysis and binding site topography," *J. Mol. Biol.* 262: 732-745 (1996).

(56) References Cited

OTHER PUBLICATIONS

Macchiarini et al., "Relation of neovascularisation to metastasis of non-small-cell lung cancer," *Lancet* 340: 145-146 (1992).
Paul, *Fundamental Immunology*, 3rd Ed., Raven Press: NY, pp. 292-295 (1993).
Popkov et al., "Human/mouse cross-reactive anti-VEGF receptor 2 recombinant antibodies selected from an immune b9 allotype rabbit antibody library," *J. Immunol. Methods* 288: 149-164 (2004).
Rak et al., "Consequences of angiogenesis for tumor progression, metastasis and cancer therapy," *Anticancer Drugs* 6: 3-18 (1995).
Rudikoff et al., "Single amino acid substitution altering antigen-binding specificity," *Proc. Natl. Acad. Sci. USA* 79: 1979-1983 (1982).
Schmidt et al., "Vascular Changes in Mouse Tumors Following Endothelial Cell Targeted Therapy," *FASEB J.* 20: A1100 (2006).
Schmidt et al., "EGFL7 regulates the collective migration of endothelial cells by restricting their spatial distribution," *Development* 134: 2913-2923 (2007).
Shields et al., "High resolution mapping of the binding site on human IgG1 for Fc gamma RI, Fc gamma RII, Fc gamma RIII, and FcRn and design of IgG1 variants with improved binding to the Fc gamma R," *J. Biol. Chem.* 276: 6591-6604 (2000).
Soncin et al., "VE-statin, an endothelial repressor of smooth muscle cell migration," *EMBO J.* 22: 5700-5711 (2003).
Stinchcombe et al., "Bevacizumab in the treatment of non-small-cell lung cancer," *Oncogene* 26: 3691-3698 (2007).
Stupack et al., "Apoptotic cues from the extracellular matrix: regulators of angiogenesis," *Oncogene* 22: 9022-9029 (2003).
Weidner et al., "Tumor angiogenesis and metastasis—correlation in invasive breast carcinoma," *N. Engl. J. Med.* 324: 1-8 (1991).
Zips et al., "New anticancer agents: in vitro and in vivo evaluation," *In Vivo* 19: 1-7 (2005).
Office Action for Australian Patent Application No. 2010245739, dated May 28, 2012.
Office Action for Canadian Patent Application No. 2,760,246, dated Jan. 21, 2013.
Office Action for New Zealand Patent Application No. 595641, dated Apr. 30, 2012.
Ewert et al., "Stability improvement of antibodies for extracellular and intracellular applications: CDR grafting to stable frameworks and structure-based framework engineering," Methods. 34(2):184-199 (2004).
Office Action for Russian Patent Application No. 2011149798, dated Jul. 23, 2013 (9 pages).

* cited by examiner

Figure 1

Amino Acid Sequences of Human and Mouse EGFL7

```
Human EGFL7   1  ---MRGSQEVLLMWLLVLAVGG-TEHAYRPGRRVCAVRAHGDPVSESFVQ
Mouse EGFL7   1  MQTMWGSGELLVAWFLVLAADGTTEHVYRPSRRVCTVGISGGSISETFVQ 47  RVYQPFLTTCDGHRACSTYRTIYRTAYRRSPGLAPARPRYACCPGWKRTS
             51  RVYQPYLTTCDGHRACSTYRTIYRTAYRRSPGVTPARPRYACCPGWKRTS
                       EMI1         p4                  EMI2      p2

97  GLPGACGAAICQPPCRNGGSCVQPGRCRCPAGWRGDTCQSDVDECSARRG
            101  GLPGACGAAICQPPCGNGGSCIRPGHCRCPVGWQGDTCQTDVDECSTGEA
                                      p5       p6                   EGF domains 141  GCPQRCINTAGSYWCQCWEGHSLSADGTLCVPKGGPPRVAPNPTG-VDSA
            151  SCPQRCVNTVGSYWCQGWEGQSPSADGTRCLSKEGPSPVAPNPTAGVDSM 196  MKEEVQRLQSRVDLLEEKLQLVLAPLHSLASQALEHGLPDPGSLLVHSFQ
            201  AREEVYRLQARVDVLEQKLQLVLAPLHSLASRSTEHGLQDPGSLLAHSFQ
                                   Coiled-coiled domains 246  QLGRIDSLSEQISFLEEQLGSCSCKKDSG
            251  QLDRIDSLSEQVSFLEEHLGSCSCKKDL-
```

Figure 2

4F11 Variable Light Domain

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | Kabat - CDR L1 | | |
| | | | | | | | | | | | | | | | | | | | | | | | | | | | | | | | | | | | | | | | | Chothia - CDR L1 | | | |
| | | | | | | | | | | | | | | | | | | | | | | | | | | | | | | | | | | | | | | | | | | Contact - CDR L1 |
| huKI | D | I | Q | M | T | Q | S | P | S | S | L | S | A | S | V | G | D | R | V | T | I | T | C | R | A | S | Q | | | | | | | S | I | S | N | Y | L | A | W | Y | Q |
| hu4F11.v1 | D | I | Q | M | T | Q | S | P | S | S | L | S | A | S | V | G | D | R | V | T | I | T | C | K | A | S | Q | | | | | | | D | G | D | S | Y | M | S | W | Y | Q |

| Kabat# | 38 | 39 | 40 | 41 | 42 | 43 | 44 | 45 | 46 | 47 | 48 | A | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | Kabat - CDR L2 | | | | | | | | | | | | | | | | | | | | | | | | | | | | | | |
| | | | | | | | | | | | | | | Chothia - CDR L2 | | | | | | | | | | | | | | | | | | | | | | | | | | | | | | |
| | | | | | | | | | | | | | Contact - CDR L2 | | | | | | | | | | | | | | | | | | | | | | | | | | | | | | | |
| huKI | Q | K | P | G | K | A | P | K | L | L | I | Y | A | A | S | S | L | E | S | G | V | P | S | R | F | S | G | S | G | S | G | T | D | F | T | L | T | I | S | S | L | Q | P |
| hu4F11.v1 | Q | K | P | G | K | A | P | K | L | L | I | Y | G | A | S | N | L | E | S | G | V | P | S | R | F | S | G | S | G | S | G | T | D | F | T | L | T | I | S | S | L | Q | P |

| Kabat# | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | Kabat - CDR L3 | | | | | | | | | | | | |
| | | | | | | | | | | | | | | | | | | | | | | Chothia - CDR L3 | | | | | | | | | | | | |
| | | | | | | | | | | | | | | | | | | | | | | Contact - CDR L3 | | | | | | | | | | | | |
| huKI | E | D | F | A | T | Y | Y | C | Q | Q | Y | N | S | L | P | | | | | | | W | T | F | G | Q | G | T | K | V | E | I | K | R |
| hu4F11.v1 | E | D | F | A | T | Y | Y | C | Q | Q | N | E | D | P | | | | | | | | Y | T | F | G | Q | G | T | K | V | E | I | K | R |

Figure 3

4F11 Variable Heavy Domain

```
Kabat#    1  2  3  4  5  6  7  8  9 10 11 12 13 14 15 16 17 18 19 20 21 22 23 24 25 26 27 28 29 30 31 32 33 34 35 A  B  36 37 38 39 40 41
                                                                                                          |—Kabat - CDR H1—|
                                                                                        |—Chothia - CDR H1—|
                                                                                              |—Contact - CDR H1—|
hum III   E  V  Q  L  V  E  S  G  G  G  L  V  Q  P  G  G  S  L  R  L  S  C  A  A  S  G  F  T  F  S  S  Y  A  M  S           W  V  R  Q  A  P
hu4F11.v1 E  V  Q  L  V  E  S  G  G  G  L  V  Q  P  G  G  S  L  R  L  S  C  A  A  S  G [H] T  T [T] Y [G] M  S              W  V  R  Q  A  P Kabat#   42 43 44 45 46 47 48 49 50 51 52 a  b  c  53 54 55 56 57 58 59 60 61 62 63 64 65 66 67 68 69 70 71 72 73 74 75 76 77 78 79 80
                           |———————— Kabat - CDR H2 ————————|
                           |——————— Chothia - CDR H2 ———————|
                        |—————————— Contact - CDR H2 ——————————|
hum III   G  K  G  L  E  W  V  S  V  I  S  G           D  G  G  S  T  Y  Y  A  D  S  V  K  G  R  F  T  I  S  R  D  N  S  K  N  T  L  Y  L
hu4F11.v1 G  K  G  L  E  W  V [G][W][I][N][T]          [H][S][G][V][P][T] Y  A  D  D [F] K  G  R  F  T  I  S  R  D  N  S  K  N  T  L  Y  L Kabat#   81 82 A  B  C  83 84 85 86 87 88 89 90 91 92 93 94 95 96 97 98 99 100 A  B  C  D  E  F  G  H  I  J  K 101 102 103 104 105 106 107 108 109 110 111 112 113
                                                                       |——————— Kabat - CDR H3 ———————|
                                                                       |—————— Chothia - CDR H3 ——————|
                                                                    |————————— Contact - CDR H3 —————————|
hum III   Q  M  N  S  L  R  A  E  D  T  A  V  Y  Y  C  A  R  G                                                              F  D  Y  W  G  Q  G  T  L  V  T  V  S  S
hu4F11.v1 Q  M  N  S  L  R  A  E  D  T  A  V  Y  Y  C  A  R [L][G][S][S][A]                                                  V  D  Y  W  G  Q  G  T  L  V  T  V  S  S
```

Figure 4

Oligonucleotide Design for the Framework Toggle Library

VL-framework 1 Region

```
      GCC TAT GCA GAT ATC CAG ATG ACC CAG TCC CCG AGC TCC  (13)
       A   Y   A   D   I   Q   M   T   Q   S   P   S   S   (14)
4F11
       GCC TAT GCA GAT ATC CAG [V] [L] ACC CAG TCC CCG [A] TCC  (15)
                                                                (16)
                   1           5                    10
```

VH-framework 1 Region

```
      ACA AAC GCG TAC GCT GAG GTT CAG CTG GTG GAG ATT GGT  (17)
       T   N   A   Y   A   E   V   Q   L   V   E   S   G   (18)
                                    Q   I           Q   S   G   (19)
      ACA AAC GCG TAC GCT [Q] [I] CAG CTG GTG GAG [Q] TCT GGC  (20)
                      1                5
```

VH-framework 2 Region

```
      GGT AAG GGC CTG GAA TGG GTT GCA AGG ATT TAT CCT  (21)
       G   K   G   L   E   W   V   A   R   I   Y   P   (22)
                       K       M       W               N       (23)
      GGT AAG GGC CTG GAA TGG [RTG] GCA AGG ATT TAT CCT  (24)
                  45                50           52   52
```

VH-framework 3 Region

```
GTC AAG GGC CGT TTC ACT ATA [I] [F] AGC CGC GAC [R] [L] [CKC] AGC  (  )
 V   K   G   R   F   T   I   T   A   S   R   D   R   L   S   S   
 [F] K   G   R   F   T   [A] [WTC] S   S                                
GTC AAG GGC CGT TTC ACT [A] [WTC] AGC                                  
      65              70
```

```
AAA AAC TCC [N] [S] GAC [E] [L] GAC [AMC] ACA CTG TAC CTA CAA CTA CAA ATG AAC AGC  
 K   N   S   S   D   E   L   D   T   T   L   Y   L   Q   L   Q   M   N   S  
 [K] [A] [RMA] [ARC]         [A] [RYG]  
         +TE            +VP
      75              80                      82  82  82
```

```
GAG GAC ACT GCC GTC TAT TAT TGT AGC CGC TGG GGA  (25)
 E   D   T   A   V   Y   Y   C   S   R   W   G   (26)
             [E] [T] [F]                [A] [L]     (27)
GAG GAC ACT GCC GTC TAT [TWC] TGT GCG [A] CGT CTG GGT  (28)
      85      90                          96
```

Figure 9A

SP Library Results

| CDR-L1 | CDR-L2 | CDR-L3 |
|---|---|---|
| KASQSVDYDGDSYMS (31) | GASNLES (32) | QQNNEDPYT (33) |

4F11.v1 framework

| | | |
|---|---|---|
| KRSQSVDYDGDSYMS (37) | GASYLES (44) | |
| KASHSVDYDGDSYMS (38) | GASNRES (45) | |
| KASQSGDYDGDSYMS (39) | GASNYES (46) | |
| | GASNRES (45) | |
| | GASNLEQ (47) | |

4F11.v2 framework

| | | |
|---|---|---|
| KASQSVDYRGDSYMS (40) | GASYLES (44) | QQNNEDPFT (48) |
| KASQSVDYDGDSYVS (41) | GASYLES | QQNNEDPFT |
| KASQSVDYDGDSYVS | GASYLES | |
| KASQSVDYDGDSYVS | GASYLES | |
| KASQSVDYDGDSYVS | GASYLES | |
| | GASYLES | |
| | GASYLES | |
| | GASYLES | |
| | GASYLES | |
| | GASYLES | |
| | GASYLES | |
| | GASYLES | |
| | GASYLES | |
| | GASYLES | |
| | GASYLES | |
| | GASYLES | |
| | GASYLES | |
| | GASYLES | |
| | GASYLES | |
| | GASYLES | |
| | GASYLES | |
| | GASYLES | |
| | GASYLES | |
| | GASYLES | |
| | GASYLES | |

4F11.v3 framework

| | | |
|---|---|---|
| *KASQSVDYRGDSYMS (40) | GASYLES (44) | |
| KASQSVDYLGDSYMS (42) | GASYLES | |
| KASQSVDYWGDSYMS (43) | GASYLES | |
| | GASYLES | |
| | GASYLES | |
| | GASYLES | |
| | GASYLES | |
| | GASYLES | |
| | GASYLES | |

Figure 9B

| CDR-H1 | CDR-H2 | CDR-H3 |
|---|---|---|
| GHTFTTYGMS (34) | GWINTHSGVPTYADDFKG (35) | ARLGSSAVDY (36) |

| | | |
|---|---|---|
| GHTGTTYGMS (49) | GWINWHSGVPTYADDFKG (58) | |
| GHTFTTYGYS (50) | GWINWHSGVPTYADDFKG (58) | |
| | GWINMHSGVPTYADDFKG (59) | |
| | GWINTHSGVPTMADDFKG (60) | |
| | GWINTHSGVPTMADDFKG (60) | |
| | GWINTHSGVPTYAHDFKG (61) | |
| | GWINTHSGVPTYADXFKG (62) | |

| | | |
|---|---|---|
| GHTFDTYGMS (51) | GWINIHSGVPTYADDFKG (63) | ANLGSSAVDY (74) |
| GHTFRTYGMS (52) | GWINWHSGVPTYADDFKG (64) | |
| GVTFTTYGMS (53) | GWINTRSGVPTYADDFKG (65) | |
| GHRFTTYGMS (54) | GWINTHSGVPTIADDFKG (66) | |
| GHTFGTYGMS (55) | GWINTHSGVPTYADFSG (67) | |
| | GWINTHSGVPTTADDFKG (68) | |
| | GWINTHSGVPTYADTFKG (69) | |

| | | |
|---|---|---|
| GHTRTTYGMS (56) | GWINIHSGVPTYADDFKG (70) | ARLGSCAVDY (75) |
| GHTSTTYGMS (57) | GWINTHSGVPTYADMFKG (71) | ARLGSCAVDY (75) |
| GHTRTTYGMS (56) | GWINTHSGVPTYADDYKG (72) | ARLGSYAVDY (76) |
| GHTRTTYGMS | GWINTHSGVPTYADDFKR (73) | ARLGSYAVDY (76) |
| GHTRTTYGMS | | ARLGSCAVDY (75) |
| | | ARLGSCAVDY (75) |
| | | ARLGSSAVDA (77) |

Figure 10

Light Chain Library Design

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | | |
| | | | | | | | | | | | | | | | | | | | | | | | | | | | | | | | | | | | Kabat - CDR L1 | | | | | | | |
| | | | | | | | | | | | | | | | | | | | | | | | | | | | | | | | | | | | Chothia - CDR L1 | | | | | | | |
| | | | | | | | | | | | | | | | | | | | | | | | | | | | | | | | | | | | | | Contact - CDR L1 | | | | | |
| huKI | D | I | Q | M | T | Q | S | P | S | S | L | S | A | S | V | G | D | R | V | T | I | T | C | R | A | S | Q | | | | | | | S | I | S | N | Y | L | A | W | Y | Q |
| hu4F11graft | D | I | Q | M | T | Q | S | P | S | S | L | S | A | S | V | G | D | R | V | T | I | T | C | K | A | S | Q | | | | | | | D | G | D | S | Y | M | S | W | Y | Q |
| Library 1 | D | I | Q | L | T | Q | S | P | S | S | L | S | A | S | V | G | D | R | V | T | I | T | C | K | A | S | Q | | | | | | | S | G | D | S | Y | M | S | W | Y | Q |
| Library 2 | D | I | Q | L | T | Q | S | P | S | S | L | S | A | S | V | G | D | R | V | T | I | T | C | K | A | S | Q | | | | | | | S | G | D | S | Y | M | S | W | Y | Q |

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | A | | | | | | | Kabat - CDR L2 | | | | | | | | | | | | | | | | | | | | | | | | | |
| | | | | | | | | | | | | | | Chothia - CDR L2 | | | | | | | | | | | | | | | | | | | | | | | | | | | | |
| | | | | | | | | | | | | | | Contact - CDR L2 | | | | | | | | | | | | | | | | | | | | | | | | | | | | |
| huKI | Q | K | P | G | K | A | P | K | L | L | I | Y | A | A | S | S | L | E | S | G | V | P | S | R | F | S | G | S | G | S | G | T | D | F | T | L | T | I | S | S | L | Q |
| hu4F11graft | Q | K | P | G | K | A | P | K | L | L | I | Y | G | A | S | N | L | E | S | G | V | P | S | R | F | S | G | S | G | S | G | T | D | F | T | L | T | I | S | S | L | Q |
| Library 1 | Q | K | P | G | K | A | P | K | L | L | I | Y | G | A | S | N | L | E | S | G | V | P | S | R | F | S | G | S | G | S | G | T | D | F | T | L | T | I | S | S | L | Q |
| Library 2 | Q | K | P | G | K | A | P | K | L | L | I | Y | G | A | S | N | L | E | S | G | V | P | S | R | F | S | G | S | G | S | G | T | D | F | T | L | T | I | S | S | L | Q |

| Kabat# | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | Kabat - CDR L3 | | | | | | | | | | | | | | | | |
| | | | | | | | | | | | | | | | | | | Chothia - CDR L3 | | | | | | | | | | | | | | | | |
| | | | | | | | | | | | | | | | | | | Contact - CDR L3 | | | | | | | | | | | | | | | | |
| huKI | E | D | F | A | T | Y | Y | C | Q | Q | Y | N | S | L | P | | | | | | | W | T | F | G | Q | G | T | K | V | E | I | K | R |
| hu4F11graft | E | D | F | A | T | Y | Y | C | Q | Q | N | N | E | D | P | | | | | | | Y | T | F | G | Q | G | T | K | V | E | I | K | R |
| Library 1 | E | D | F | A | T | Y | Y | C | Q | Q | N | N | E | E | P | | | | | | | Y | T | F | G | Q | G | T | K | V | E | I | K | R |
| Library 2 | E | D | F | A | T | Y | Y | C | Q | Q | N | N | E | E | P | | | | | | | Y | T | F | G | Q | G | T | K | V | E | I | K | R |

Figure 11

Heavy Chain Library Design

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | Chothia - CDR H1 | | | | | Kabat - CDR H1 | | | | | | | | | | |
| | | | | | | | | | | | | | | | | | | | | | | | | | | | | | | | | Contact - CDR H1 | | | | | | | | | | |
| hum III | E | V | Q | L | V | E | S | G | G | G | L | V | Q | P | G | G | S | L | R | L | S | C | A | A | S | G | F | T | F | S | S | Y | A | M | S | | | W | V | R | Q | A | P |
| hu4F11graft | E | V | Q | L | L | E | S | G | G | G | L | V | Q | P | G | G | S | L | R | L | S | C | A | A | S | G | H | T | F | T | T | Y | G | M | S | | | W | V | R | Q | A | P |
| Library 1 | E | V | Q | L | V | E | S | G | G | G | L | V | Q | P | G | G | S | L | R | L | S | C | A | A | S | G | H | T | F | K | T | Y | G | M | S | | | W | V | R | Q | A | P |
| Library 2 | E | V | Q | L | V | E | S | G | G | G | L | V | Q | P | G | G | S | L | R | L | S | C | A | A | S | G | H | T | F | T | T | Y | G | M | S | | | W | V | R | Q | A | P |

| Kabat# | 42 | 43 | 44 | 45 | 46 | 47 | 48 | 49 | 50 | 51 | 52 | a | b | c | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | Kabat - CDR H2 | | | | | | | | | | | | | | | | | | | | | | | | | | | | | | | | | |
| | | | | | | | | | Chothia - CDR H2 | | | | | | | | | | | | | | | | | | | | | | | | | | | | | | | | | |
| | | | | | | | | | | | | | | Contact - CDR H2 | | | | | | | | | | | | | | | | | | | | | | | | | | | |
| hum III | G | K | G | L | E | W | V | S | V | I | S | G | | | D | G | G | S | T | Y | Y | A | D | S | V | K | G | R | F | T | I | S | R | D | N | S | K | N | T | L | Y | L |
| hu4F11graft | G | K | G | L | E | W | V | G | W | N | T | | | | H | S | G | V | P | T | Y | A | D | D | F | K | G | R | F | T | I | S | R | D | N | S | K | N | T | L | Y | L |
| Library 1 | G | K | G | L | E | W | V | G | W | N | X | | | | H | S | G | V | P | T | Y | A | D | D | F | K | G | R | F | T | I | S | L | D | N | S | K | N | T | L | Y | L |
| Library 2 | G | K | G | L | E | W | V | G | W | N | X | | | | H | S | G | V | P | T | Y | A | D | D | F | K | G | R | F | T | I | S | L | D | N | S | K | N | T | L | Y | L |

| Kabat# | 81 | 82 | A | B | C | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | Kabat - CDR H3 | | | | | | | | | | | | |
| | | | | | | | | | | | | | | | | | | | | | | | | | | | | | | | | | | | Chothia - CDR H3 | | | | | | | | | | | | |
| | | | | | | | | | | | | | | | | | | | | | | | | | | | | | | | | | | | Contact - CDR H3 | | | | | | | | | | | | |
| hum III | Q | M | N | S | L | R | A | E | D | T | A | V | Y | Y | C | A | R | | | | | | G | | | | | | | | | | | | F | D | Y | W | G | Q | G | T | L | V | T | V | S |
| hu4F11graft | Q | M | N | S | L | R | A | E | D | T | A | V | Y | Y | C | A | R | L | G | S | S | A | | | | | | | | | | | | | D | Y | W | G | Q | G | T | L | V | T | V | S | S |
| Library 1 | Q | M | N | S | L | R | A | E | D | T | A | V | Y | Y | C | A | R | L | G | S | X | A | | | | | | | | | | | | | V | D | Y | W | G | Q | G | T | L | V | T | V | S | S |
| Library 2 | Q | M | N | S | L | R | A | E | D | T | A | V | Y | Y | C | F | R | L | G | S | X | A | | | | | | | | | | | | | V | D | Y | W | G | Q | G | T | L | V | T | V | S | S |

Figure 12
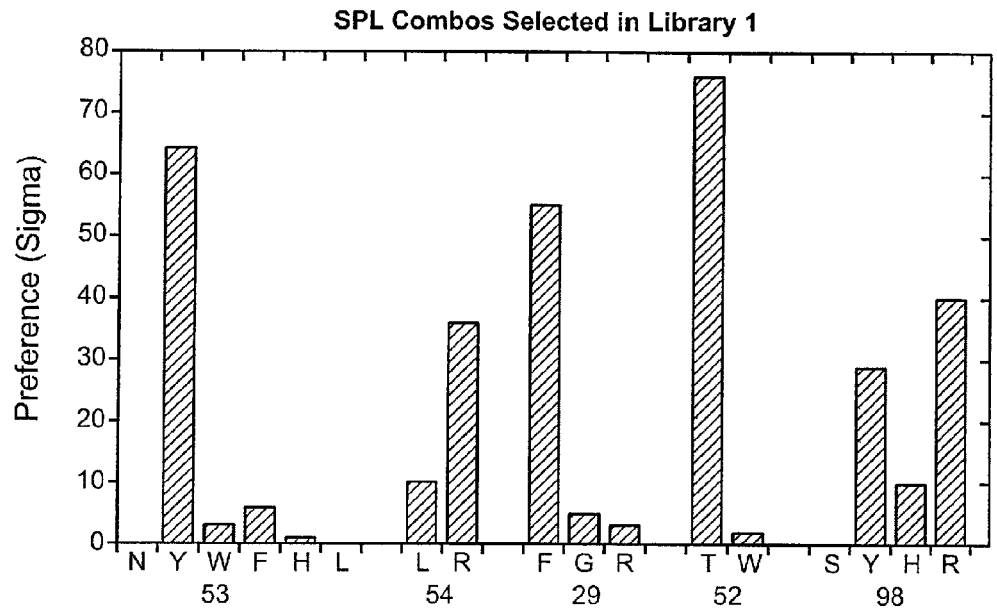
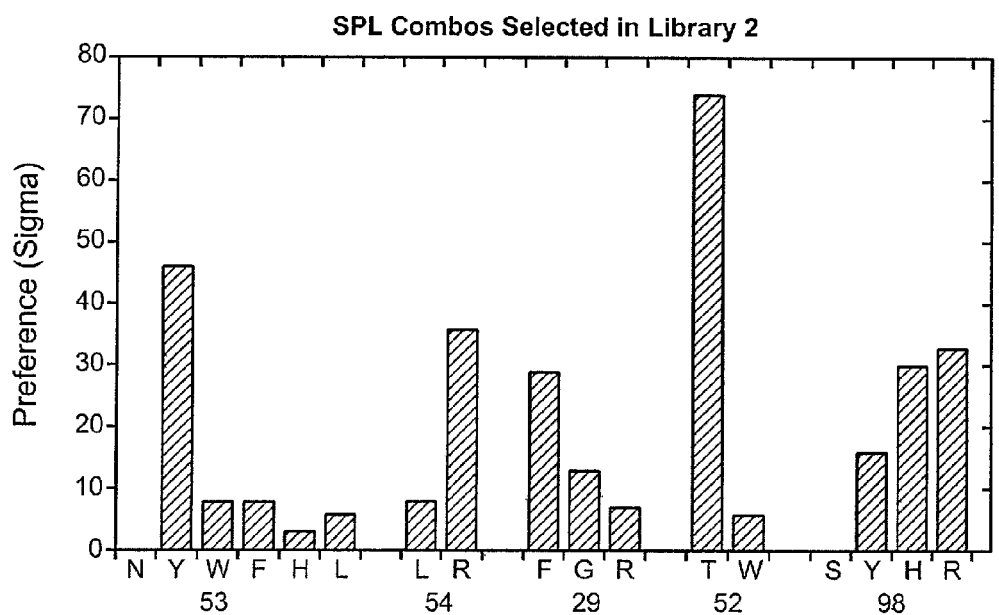

Figure 15

Humanized 4F11 Variable Light Chain

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | | |
| | | | | | | | | | | | | | | | | | | | | | | | | | | | | | | | | | | Kabat - CDR L1 | | | | | | | | | |
| | | | | | | | | | | | | | | | | | | | | | | | | | | | | | | Chothia - CDR L1 | | | | | | | | | | | |
| | | | | | | | | | | | | | | | | | | | | | | | | | | | | | | | | | | | | Contact - CDR L1 | | | | | | |
| huKI | D | I | Q | M | T | Q | S | P | S | S | L | S | A | S | V | G | D | R | V | T | I | T | C | R | A | S | Q | | | | | | | S | I | S | N | Y | L | A | W | Y | Q |
| hu4F11graft | D | I | Q | M | T | Q | S | P | S | S | L | S | A | S | V | G | D | R | V | T | I | T | C | K | A | S | Q | S | V | D | | | | D | G | D | S | Y | M | S | W | Y | Q |
| 4F11.v17 | D | I | Q | M | T | Q | S | P | S | S | L | S | A | S | V | G | D | R | V | T | I | T | C | K | A | S | Q | S | V | D | | | | S | G | D | S | Y | M | S | W | Y | Q |
| 4F11.v22 | D | I | Q | M | T | Q | S | P | S | S | L | S | A | S | V | G | D | R | V | T | I | T | C | K | A | S | Q | S | V | D | | | | S | G | D | S | Y | M | S | W | Y | Q |

| Kabat# | 38 | 39 | 40 | 41 | 42 | 43 | 44 | 45 | 46 | 47 | 48 | A | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | Kabat - CDR L2 | | | | | | | | | | | | | | | | | | | | | | | | | | | | |
| | | | | | | | | | | | | | | | | | Chothia - CDR L2 | | | | | | | | | | | | | | | | | | | | | | | | | | |
| | | | | | | | | | | | | Contact - CDR L2 | | | | | | | | | | | | | | | | | | | | | | | | | | | | | | | |
| huKI | Q | K | P | G | K | A | P | K | L | L | I | | Y | A | A | S | S | L | E | S | G | V | P | S | R | F | S | G | S | G | S | G | T | D | F | T | L | T | I | S | S | L | Q | P |
| hu4F11graft | Q | K | P | G | K | A | P | K | L | L | I | | Y | G | A | S | N | L | E | S | G | V | P | S | R | F | S | G | S | G | S | G | T | D | F | T | L | T | I | S | S | L | Q | P |
| 4F11.v17 | Q | K | P | G | K | A | P | K | L | L | I | | Y | G | A | S | Y | R | E | S | G | V | P | S | R | F | S | G | S | G | S | G | T | D | F | T | L | T | I | S | S | L | Q | P |
| 4F11.v22 | Q | K | P | G | K | A | P | K | L | L | I | | Y | G | A | S | Y | R | E | S | G | V | P | S | R | F | S | G | S | G | S | G | T | D | F | T | L | T | I | S | S | L | Q | P |

| Kabat# | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|---|---|---|---|---|---|
| | | | | | | | | | | | | | | Kabat - CDR L3 | | | | | | | | | | | | | | | | | | | | |
| | | | | | | | | | | | | | | Chothia - CDR L3 | | | | | | | | | | | | | | | | | | | | |
| | | | | | | | | | | | | | | Contact - CDR L3 | | | | | | | | | | | | | | | | | | | | |
| huKI | E | D | F | A | T | Y | Y | C | Q | Q | Y | N | S | L | P | | | | | | | W | T | F | G | Q | G | T | K | V | E | I | K | R |
| hu4F11graft | E | D | F | A | T | Y | Y | C | Q | Q | N | N | E | D | P | | | | | | | Y | T | F | G | Q | G | T | K | V | E | I | K | R |
| 4F11.v17 | E | D | F | A | T | Y | Y | C | Q | Q | N | N | E | E | P | | | | | | | Y | T | F | G | Q | G | T | K | V | E | I | K | R |
| 4F11.v22 | E | D | F | A | T | Y | Y | C | Q | Q | N | N | E | E | P | | | | | | | Y | T | F | G | Q | G | T | K | V | E | I | K | R |

Figure 16

Humanized 4F11 Variable Heavy Chain

Figure 17

18F7 Variable Light Domain

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | | |
| | | | | | | | | | | | | | | | | | | | | | | | | | | | | | | | | | | Kabat - CDR L1 | | | | | | | | | |
| | | | | | | | | | | | | | | | | | | | | | | | | | | | | | | | | | | | | | | Chothia - CDR L1 | | | | |
| | | | | | | | | | | | | | | | | | | | | | | | | | | | | | | | | | | | | | | | Contact - CDR L1 | | | | |
| huKI | D | I | Q | M | T | Q | S | P | S | S | L | S | A | S | V | G | D | R | V | T | I | T | C | R | A | S | Q | | | | | | S | I | S | N | Y | L | A | W | Y | Q |
| 18F7-graft | D | I | Q | M | T | Q | S | P | S | S | L | S | A | S | V | G | D | R | V | T | I | T | C | R | T | S | Q | S | L | V | H | I | N | G | I | T | Y | L | H | W | Y | Q |
| | * | | | * | | | | | | | | | | | | | | | | | | | | | * | * | | * | * | * | * | * | * | * | * | * | * | * | * | | | * |

| Kabat# | 38 | 39 | 40 | 41 | 42 | 43 | 44 | 45 | 46 | 47 | 48 | A | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | Kabat - CDR L2 | | | | | | | | | | | | | | | | | | | | | | | | | | | | |
| | | | | | | | | | | | | | | | | Chothia - CDR L2 | | | | | | | | | | | | | | | | | | | | | | | | | | | |
| | | | | | | | | | | | | | | | Contact - CDR L2 | | | | | | | | | | | | | | | | | | | | | | | | | | | | |
| huKI | Q | K | P | G | K | A | P | K | L | L | I | Y | A | A | S | S | L | E | S | G | V | P | S | R | F | S | G | S | G | S | G | T | D | F | T | L | T | I | S | S | L | Q | P |
| 18F7-graft | Q | K | P | G | K | A | P | K | L | L | I | Y | R | V | S | N | R | F | S | G | V | P | S | R | F | S | G | S | G | S | G | T | D | F | T | L | T | I | S | S | L | Q | P |
| | * | | | | | | | | | | | | * | * | * | * | * | * | | | | | | | | | | | | | | | | | | | | | | | | | |

| Kabat# | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|---|---|---|---|---|---|
| | | | | | | | | | | | | | | Kabat - CDR L3 | | | | | | | | | | | | | | | | | | | | |
| | | | | | | | | | | | | | | Chothia - CDR L3 | | | | | | | | | | | | | | | | | | | | |
| | | | | | | | | | | | | | | Contact - CDR L3 | | | | | | | | | | | | | | | | | | | | |
| huKI | E | D | F | A | T | Y | Y | C | Q | Q | Y | N | S | L | P | | | | | | | W | T | F | G | Q | G | T | K | V | E | I | K | R |
| 18F7-graft | E | D | F | A | T | Y | Y | C | S | Q | S | T | H | V | P | | | | | | | L | T | F | G | Q | G | T | K | V | E | I | K | R |
| | | | | | | | | | * | | * | * | * | | | | | | | | | * | | | | | | | | | | | | |

Figure 18

18F7 Variable Heavy Domain

| Kabat# | 1 2 3 4 5 6 7 8 9 10 11 12 13 14 15 16 17 18 19 20 21 22 23 24 25 26 27 28 29 30 31 32 33 34 35 A B 36 37 38 39 40 41 |
|---|---|
| hum III  | E V Q L V E S G G G L V Q P G G S L R L S C A A S G F T F S S Y A M S W V R Q A P |
| 18F7-graft | E V Q L V E S G G G L V Q P G G S L R L S C A A S G Y T F I D Y Y M N W V R Q A P |
|  | * * * * * * * |

Kabat – CDR H1 spans 31–35B; Chothia – CDR H1 spans 26–32; Contact – CDR H1 spans 30–35B

| Kabat# | 42 43 44 45 46 47 48 49 50 51 52 a b c 53 54 55 56 57 58 59 60 61 62 63 64 65 66 67 68 69 70 71 72 73 74 75 76 77 78 79 80 |
|---|---|
| hum III | G K G L E W V S V I S G D G G S T Y Y A D S V K G R F T I S R D N S K N T L Y L |
| 18F7-graft | G K G L E W V G D I N L D N G T H Y N Q K F K G R F T I S R D N S K N T L Y L |
|  | * * * * * * * * * * |

Kabat – CDR H2 spans 50–65; Chothia – CDR H2 spans 52–56; Contact – CDR H2 spans 47–58

| Kabat# | 81 82 A B C 83 84 85 86 87 88 89 90 91 92 93 94 95 96 97 98 99 100 A B C D E F G H I J K 101 102 103 104 105 106 107 108 109 110 111 112 113 |
|---|---|
| hum III | Q M N S L R A E D T A V Y Y C A R G                                 F D Y W G Q G T L V T V S S |
| 18F7-graft | Q M N S L R A E D T A V Y Y C A R E G V Y H D Y D D Y A M D Y W G Q G T L V T V S S |
|  | * * * * |

Kabat – CDR H3 spans 95–102; Chothia – CDR H3 spans 95–102; Contact – CDR H3 spans 93–101

Figure 19

Oligonucleotide Design for the Framework Toggle Library

VL-framework 3 Region

```
                              85           87        90
      E   D   F   A   T   Y   C   Q   S   T   T
      E   D   L   G   V   Y   C   Q   S   T   H
      GAA GAC TTC GCA ACT TAT TGT CAG AGC ACC ACC  (88)
      GAA GAC TTC GCA ACT TAT TAC TGT CAG AGC ACC CAC  (89)
                                                       (90)
      GAA GAC TTC GCA ACT TAT TWC TGT CAG AGC ACC CAC  (91)
```

VH-framework 2 Region

```
              45           48   50              52  52
      G   K   G   L   E   W   V   D   I   N   L   D
      G   K   S   L   E   W   I   D   I   N   L   D
      GGT AAG GGC CTG GAA TGG GTT GAT ATC AAC CTG GAT  (92)
                                                      (93)
                                                      (94)
      GGT AAG GGC CTG GAA TGG RTC GAT ATC AAC CTG GAT  (95)
```

VH-framework 3 Region

```
 61          65          67          69  70  71      73          75  76      78          80          82  82  82  82  82
 Q   K   F   K   G   R   F   T   F   I   S   R   D   T   S   K   N   T   L   Y   L   Q   M   N   S   L   R
 Q   K   F   K   G   R   A   T   L   L   T   V   K   K   S   A   I   M   H   E   L   T
 CAG AAA TTC AAA GGT CGT TTC ACT TTC ATA AGC CGT GAC ACC TCC AAA AAC ACA CTG TAC CAA ATG AAC AGC TTA AGA
                         KYC     MTC             SKT     AMG     ARS ARC     SYG     MTG
                         +SV     +LG             +LG     +PV     +NR +PV     +PV
 CAG AAA TTC AAA GGT CGT KYC ACT MTC AGC SKT GAC AMG TCC ARS ARC ACA SYG TAC MTG CAA ATG AAC AGC TTA AGA
```
(96) (97) (98) (99)

Figure 24A

SP Library Results

| CDR-L1 | CDR-L2 | CDR-L3 |
|---|---|---|
| RTSQSLVHINGITYLH (100) | RVSNRFS (101) | SQSTHVPLT (102) |

18F7-graft (N73, L78)

| | | |
|---|---|---|
| QTSQSLVHINGITYLH (106) | RVSNDFS (125) | *AQSTHVPLT (130) |
| RTSQSLVHYNGITYLH (107) | | *GQSTHVPLT (131) |
| RTSQSLVPINGITYLH (108) | | *LQSTHVPLT (132) |
| | | SQSCHVPLT (133) |
| | | SQSTFVPLT (134) |

18F7-K (K73, L78)

| | | |
|---|---|---|
| STSQSLVHINGITYLH (109) | | *AQSTHVPLT (135) |
| RTSQSLVHLNGITYLH (110) | | *GQSTHVPLT (136) |
| | | *LQSTHVPLT (137) |

18F7-KV (K73, V78)

| | | |
|---|---|---|
| LTSQSLVHINGITYLH (111) | RVSNRIS (126) | *AQSTHVPLT (138) |
| RWSQSLVHINGITYLH (112) | RVSNRTS (127) | NQSTHVPLT (139) |
| RPSQSLVHINGITYLH (113) | | |
| RTHQHLVHINGITYLH (114) | | |
| RTSQSVVHINGITYLH (115) | | |
| RTSQSLVHTNGITYLH (116) | | |
| RTSQSLVHLNGITYLH (117) | | |
| RTSQSLVHPNGITYLH (118) | | |
| RTSQSLVHINGITYLG (119) | | |

18F7-KA (K73, A78)

| | | |
|---|---|---|
| TTSQSLVHINGITYLH (120) | RVSNRGS (128) | *AQSTHVPLT (140) |
| LTSQSLVHINGITYLH (121) | RVSNRAS (129) | IQSTHVPLT (141) |
| RTSDSLVHINGITYLH (122) | | *LQSTHVPLT (142) |
| RTSQGLVHINGITYLH (123) | | *VQSTHVPLT (143) |
| RTSQSLVHYNGITYLH (124) | | TQSTHVPLT (144) |
| | | KQSTHVPLT (145) |

\* Highly Abundant Clones

Figure 24B

| CDR-H1 | CDR-H2 | CDR-H3 |
|---|---|---|
| GYTFIDYYMN (103) | GDINLDNGGTHYNQKFKG (104) | AREGVYHDYDDYAMDY (105) |

| | | |
|---|---|---|
| GYTVIDYYMN (146) | GDINLDGGGTHYNQKFKG (154) | NREGVYHDYDDYAMDY (188) |
| GYTFIDYYIN (147) | GDINLDNGKTHYNQKFKG (155) | |
| | GDINLLNGGTHYNQKFKG (156) | |
| | GDINLDNGRTHYNQKFKG (157) | |
| | GDINLDNGITHYNQKFKG (158) | |
| | GDINLDNGGHYNQKFKG (159) | |
| | GDINLDNGGTHYSQKFKG (160) | |
| | GDINLDNGGTHYNNKFKG (161) | |
| | GDINLDNGGTHYNQKQTG (162) | |
| | GDINLDNGGTHYNQKFTG (163) | |
| | GDINLDNGGTHYNQKFKH (164) | |
| | GDINLDNGGTHYNQKFKS (165) | |

| | | |
|---|---|---|
| | GDINADNGGTHYNQKFKG (166) | TREGVYHDYDDYAMDY (189) |
| | GDINLDNGTTHYNQKFKG (167) | AREGVYHPYDDYAMDY (190) |
| | GDINLDNGGTHYNAKFKG (168) | |
| | GDINLDNGGTHYNNKFKG (169) | |
| | GDINLDNGGTHYNQVFKG (170) | |
| | GDINLDNGGTHYNQKFKR (171) | |
| | GDINLDRGGTHYNQKFKG (172) | |

| | | |
|---|---|---|
| GYNFIDYYMN (148) | GDINNDNGGTHYNQKFKG (173) | AREGVYHPYDDYAMDY (191) |
| GYTFMDYYMN (149) | GDINPDNGGTHYNQKFKG (174) | AREGVYHDYDDYAWDY (192) |
| GYTFRDYYMN (150) | GDINLRNGGTHYNQKFKG (175) | |
| GYTFSDYYMN (151) | GDINLDYGGTHYNQKFKG (176) | |
| GYTFIDQYMN (152) | GDINLDSGGTHYNQKFKG (177) | |
| GYTFIDKYMN (153) | GDINLDRGGTHYNQKFKG (178) | |
| | GDINLDKGGTHYNQKFKG (179) | |
| | GDINLDNGVTHYNQKFKG (180) | |
| | GDINLDNGSTHYNQKFKG (181) | |
| | GDINLDNGRHYNQKFKG (182) | |
| | GDINLDNGGTHVNQKFKG (183) | |
| | GDINLDNGGTHINQKFKG (184) | |
| | GDINLDNGGTHLNQKFKG (185) | |
| | GDINLDNGGTHYNQKFKR (186) | |
| | GDINLDNGGTHYNQKFKS (187) | |

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | |
| | | | | | | | | | | | | | | | | | | | | | | | | | | | Kabat - CDR L1 | | | | | | | | |
| | | | | | | | | | | | | | | | | | | | | | | | | Chothia - CDR L1 | | | | | | | | | | |
| | | | | | | | | | | | | | | | | | | | | | | | | | | | | Contact - CDR L1 | | | | | | |
| huKI | D | I | Q | M | T | Q | S | P | S | S | L | S | A | S | V | G | D | R | V | T | I | T | C | R | A | S | Q | S | I | S | N | Y | L | A | W | Y | Q |
| 18F7.v6 | D | I | Q | M | T | Q | S | P | S | S | L | S | A | S | V | G | D | R | V | T | I | T | C | R | T | S | Q | S | L | V | H | I | T | Y | H | W | Y | Q |
| 18F7.v6k | D | I | Q | M | T | Q | S | P | S | S | L | S | A | S | V | G | D | R | V | T | I | T | C | R | T | S | Q | S | L | V | H | I | N G A | I | T | Y | H | W | Y | Q |

| Kabat# | 38 | 39 | 40 | 41 | 42 | 43 | 44 | 45 | 46 | 47 | 48 | A | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | Kabat - CDR L2 | | | | | | | | | | | | | | | | | | | | | | | | | | | | | |
| | | | | | | | | | | | | | | | Chothia - CDR L2 | | | | | | | | | | | | | | | | | | | | | | | | | | | | |
| | | | | | | | | | | | | | | | | | Contact - CDR L2 | | | | | | | | | | | | | | | | | | | | | | | | |
| huKI | Q | K | P | G | K | A | P | K | L | L | I | Y | A | A | S | S | L | E | S | G | V | P | S | R | F | S | G | S | G | S | G | T | D | F | T | L | T | I | S | S | L | Q | P |
| 18F7.v6 | Q | K | P | G | K | A | P | K | L | L | I | Y | R | V | S | N | R | F | S | G | V | P | S | R | F | S | G | S | G | S | G | T | D | F | T | L | T | I | S | S | L | Q | P |

| Kabat# | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|---|---|---|---|---|---|
| | | | | | | | | | | | | | | | Kabat - CDR L3 | | | | | | | | | | | | | | | | | | | |
| | | | | | | | | | | | | | | | Chothia - CDR L3 | | | | | | | | | | | | | | | | | | |
| | | | | | | | | | | | | | | | Contact - CDR L3 | | | | | | | | | | | | | | | | | | |
| huKI | E | D | F | A | T | Y | Y | C | Q | Q | Y | N | S | L | P | | | | | | | W | T | F | G | Q | G | T | K | V | E | I | K | R |
| 18F7.v6 | E | D | F | A | T | Y | Y | C | G | Q | S | T | H | V | P | | | | | | | L | T | F | G | Q | G | T | K | V | E | I | K | R |

HUMANIZED ANTI-EGFL7 ANTIBODIES AND METHODS USING SAME

RELATED APPLICATION

This application is a divisional of U.S. application Ser. No. 12/776,259, filed 7 May 2010, which claims priority under 35 USC 119(e) to provisional application No. 61/176,817, filed 8 May 2009, the contents of which are incorporated herein by reference.

FIELD OF THE INVENTION

The present invention relates generally to the field of molecular biology. More specifically, the invention concerns anti-EGFL7 antibodies, and uses of same.

BACKGROUND OF THE INVENTION

The development of a vascular supply is a fundamental requirement for many physiological and pathological processes. Actively growing tissues such as embryos and tumors require adequate blood supply. They satisfy this need by producing pro-angiogenic factors, which promote new blood vessel formation from existing vessels via a process called angiogenesis; or from progenitor cells through a process called vasculogenesis. Tubulogenesis is an essential step in vascular development. Vascular tube formation is a complex but orderly biological event involving all or many of the following steps: a) endothelial cells (EC) proliferate from existing ECs or differentiate from progenitor cells; b) EC migration; c) ECs coalesce to form cord-like structures; d) vascular cords then undergo tubulogenesis to form vessels with a central lumen e) existing cords or vessels send out sprouts to form secondary vessels (angiogenesis); f) primitive vascular plexus undergo further remodeling and reshaping; and g) peri-endothelial cells are recruited to encase the endothelial tubes, providing maintenance and modulatory functions to the vessels; such cells including pericytes for small capillaries, smooth muscle cells for larger vessels, and myocardial cells in the heart. Hanahan, D. Science 277, 48-50 (1997); Hogan, B. L. & Kolodziej, P. A. Nature Reviews Genetics. 3, 513-23 (2002); Lubarsky, B. & Krasnow, M. A. Cell. 112, 19-28 (2003).

It is now well established that angiogenesis, which involves the formation of new blood vessels from preexisting endothelium, is implicated in the pathogenesis of a variety of disorders. These include solid tumors and metastasis, atherosclerosis, retrolental fibroplasia, hemangiomas, chronic inflammation, intraocular neovascular syndromes such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Folkman et al., J. Biol. Chem., 267: 10931-10934 (1992); Klagsbrun et al., Annu. Rev. Physiol., 53: 217-239 (1991); and Garner A., "Vascular diseases", In: Pathobiology of Ocular Disease. A Dynamic Approach, Garner A., Klintworth G K, eds., 2nd Edition (Marcel Dekker, N.Y., 1994), pp 1625-1710.

In the case of tumor growth, angiogenesis appears to be crucial for the transition from hyperplasia to neoplasia, and for providing nourishment for the growth and metastasis of the tumor. Folkman et al., Nature, 339: 58 (1989). The neovascularization allows the tumor cells to acquire a growth advantage and proliferative autonomy compared to normal cells. A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. Accordingly, a correlation has been observed between density of microvessels in tumor sections and patient survival in breast cancer as well as in several other tumors. Weidner et al., N. Engl. J. Med, 324: 1-6 (1991); Horak et al., Lancet, 340: 1120-1124 (1992); Macchiarini et al., Lancet, 340: 145-146 (1992). The precise mechanisms that control the angiogenic switch is not well understood, but it is believed that neovascularization of tumor mass results from the net balance of a multitude of angiogenesis stimulators and inhibitors (Folkman, 1995, Nat Med 1(1):27-31).

The process of vascular development is tightly regulated. To date, a significant number of molecules, mostly secreted factors produced by surrounding cells, have been shown to regulate EC differentiation, proliferation, migration and coalescence into cord-like structures. For example, vascular endothelial growth factor (VEGF) has been identified as the key factor involved in stimulating angiogenesis and in inducing vascular permeability. Ferrara et al., Endocr. Rev., 18: 4-25 (1997). The finding that the loss of even a single VEGF allele results in embryonic lethality points to an irreplaceable role played by this factor in the development and differentiation of the vascular system. Furthermore, VEGF has been shown to be a key mediator of neovascularization associated with tumors and intraocular disorders. Ferrara et al., Endocr. Rev., supra. The VEGF mRNA is overexpressed by the majority of human tumors examined. Berkman et al., J. Clin. Invest., 91: 153-159 (1993); Brown et al., Human Pathol., 26: 86-91 (1995); Brown et al., Cancer Res., 53: 4727-4735 (1993); Mattern et al., Brit. J. Cancer, 73: 931-934 (1996); Dvorak et al., Am. J. Pathol., 146: 1029-1039 (1995).

Some of the steps during vessel tube formation are still poorly defined. Particularly, little is know about how tubulogenesis is regulated—how vascular cords progress to become tubes, and what factors regulate this transition. In view of the role of vasculogenesis and angiogenesis in many diseases and disorders, it is desirable to have a means of reducing or inhibiting one or more of the biological effects causing these processes. All references cited herein, including patent applications and publications, are incorporated by reference in their entirety.

SUMMARY OF THE INVENTION

The invention is in part based on a variety of antibodies to EGFL7. EGFL7 presents as an important and advantageous therapeutic target, and the invention provides antibodies as therapeutic and diagnostic agents for use in targeting pathological conditions associated with expression and/or activity of EGFL7. Accordingly, the invention provides methods, compositions, kits and articles of manufacture related to EGFL7.

For example, in some embodiments, the invention provides anti-EGFL7 antibodies. In some embodiments, the invention provides an anti-EGFL7 antibody comprising a variable domain comprising at least one, two, three, four or five hypervariable region (HVR) sequences selected from the group consisting of: (i) HVR-L1 comprising $KX_1SX_2SX_3DYX_4GDSYX_5S$, wherein $X_1$ is A or R; $X_2$ is H or Q; $X_3$ is G or V; $X_4$ is selected from the group consisting of D, L, R, S, and W; and $X_5$ is M or V (SEQ ID NO: 210); (ii) HVR-L2 comprising GASX$_1$X$_2$EX$_3$, wherein $X_1$ is N or Y; $X_2$ is selected from the group consisting of L, R and Y; and $X_3$ is Q or S (SEQ ID NO: 211); (iii) HVR-L3 comprising QQNNEX$_1$PX$_2$T, wherein $X_1$ is D or E; and $X_2$ is F or Y (SEQ ID NO: 212); (iv) HVR-H1 comprising GX$_1$X$_2$X$_3$X$_4$TYGX$_5$S, wherein $X_1$ is H or V; $X_2$ is R or T; $X_3$ is selected from the group consisting of F, G, R, and S; $X_4$ is selected from the group consisting of D, G, R, and T; and $X_5$ is M or Y (SEQ ID NO: 213); (v) HVR-H2 comprising GWINX$_1$X$_2$SGVPTX$_3$AX$_4$X$_5$X$_6$X$_7$X$_8$, wherein $X_1$ is selected from the group consisting of I, M, T, and W; $X_2$ is H or R; $X_3$ is selected from group consisting of I, M, T, and Y; $X_4$ is D or H; $X_5$ is selected from group consisting of D, M and T; $X_6$ is F or Y; $X_7$ is K or S; and $X_8$ is G or R (SEQ ID NO: 214; and (vi) HVR-H3 comprising AX$_1$LGSX$_2$AVDX$_3$, wherein $X_1$ is N or R; $X_2$ is selected from the group consisting of C, S, and Y; and $X_3$ is A or Y (SEQ ID NO: 215). In some embodiments, the anti-EGFL7 antibody comprises all six of the aforementioned HVRs. In some embodiments, HVR-L1 comprises an amino acid sequence selected from SEQ ID NOs: 31 and 37-43, HVR-L2 comprises an amino acid sequence selected from the group consisting of SEQ ID NOs: 32 and 44-47, HVR-L3 comprises an amino acid sequence selected from the group consisting of SEQ ID NOs: 33 and 48, HVR-H1 comprises an amino acid sequence selected from the group consisting of SEQ ID NOs: 34 and 49-57, HVR-H2 comprises an amino acid sequence selected from the group consisting of SEQ ID NOs: 35 and 58-73, and HVR-H3 comprises an amino acid sequence selected from the group consisting of SEQ ID NOs: 36 and 74-77. In some embodiments the heavy chain comprises the following framework sequences: FR-H1 comprises EX$_1$QLVESGGGLVQPGGSLRLSCAAS, wherein $X_1$ is I or V (SEQ ID NO: 216); FR-H2 comprises WVRQAPGK-GLEWX$_1$, wherein $X_1$ is I or V (SEQ ID NO: 217); FR-H3 comprises RFTX$_1$SX$_2$DX$_3$SX$_4$X$_5$TX$_6$YLQMNSLRAEDTAVYX$_7$CAR, wherein $X_1$ is F or I; $X_2$ is L or R; $X_3$ is N or T, $X_4$ is selected from the group consisting of A, E, K and T; $X_5$ is N or S; $X_6$ is selected from the group consisting of A, L, M, T and V; and $X_7$ is F or Y (SEQ ID NO: 218); and FR-H4 comprises WGQGTLVTVSS (SEQ ID NO: 219). In some embodiments, the heavy chain comprises the following framework sequences: FR-H1 comprises EVQLVESGGGLVQPGGSL-RLSCAAS (SEQ ID NO: 197); FR-H2 comprises WVRQAPGKGLEWV (SEQ ID NO: 198); FR-H3 comprises RFTISX$_1$DNSKNTX$_2$YLQMNSLRAEDTAVYYCAR, wherein $X_1$ L or R; $X_2$ is selected from the group consisting of A, L, M, T and V (SEQ ID NO: 220); and FR-H4 comprises WGQGTLVTVSS (SEQ ID NO: 200). In some embodiments, the light chain comprises the following framework sequences: FR-L1 comprises DIQMTQSPSSLSAS-VGDRVTITC (SEQ ID NO: 201), FR-L2 comprises WYQQKPGKAPKLLIY (SEQ ID NO: 202), FR-L3 comprises GVPSRFSGSGSGTDFTLTISSLQPEDFATYYC (SEQ ID NO: 203), FR-L4 comprises FGQGTKVEIK (SEQ ID NO: 221) or FGQGTKVEIKR (SEQ ID NO: 204). In some embodiments, the light chain comprises the variable domain sequence of 4F11.v17 or 4F11.v22 as shown in FIG. 15 (SEQ ID NOs: 82 and 83). In some embodiments, the heavy chain comprises the variable domain sequence of 4F11.v17 or 4F11.v22 as shown in FIG. 16 (SEQ ID NOs: 84 and 85). In some embodiments, the invention provides an antibody wherein the light chain comprises the variable domain sequence of 4F11.v17 as shown in FIG. 15 (SEQ ID NO: 82) and the heavy chain comprises the variable domain sequence of 4F11.v17 as shown in FIG. 16 (SEQ ID NO: 84). In some embodiments, the invention provides an antibody wherein the light chain comprises the variable domain sequence of 4F11.v22 as shown in FIG. 15 (SEQ ID NO: 83) and the heavy chain comprises the variable domain sequence of 4F11.v22 as shown in FIG. 16 (SEQ ID NO: 85).

In some embodiments, the invention provides a anti-EGFL7 antibody comprising a variable domain comprising at least one, two, three, four or five HVR sequences selected from the group consisting of: (i) HVR-L1 comprising $X_1X_2X_3X_4X_5X_6VX_7X_8X_9X_{10}$ITYLX$_{11}$, wherein $X_1$ is selected from the group consisting of L, Q, R, S, and T; $X_2$ is selected from the group consisting of P, T, and W; $X_3$ is H or S; $X_4$ is D or Q; $X_5$ is G or S; $X_6$ is L or V; $X_7$ is H or P; $X_8$ is selected from the group consisting of I, L, P, T, and Y; $X_9$ is selected from the group consisting of N, Q or S; $X_{10}$ is selected from the group consisting of A, G, and S; and $X_{11}$ is G or H (SEQ ID NO: 222); (ii) HVR-L2 comprising RVSNX$_1$X$_2$S, wherein $X_1$ is D or R; and $X_2$ is selected from the group consisting of A, G, F, I, and T (SEQ ID NO: 223); (iii) HVR-L3 comprising X$_1$QSX$_2$X$_3$VPLT, wherein $X_1$ is selected from the group consisting of A, G, I, K, L, N, S, T, and V; $X_2$ is C or T; and $X_3$ is F or H (SEQ ID NO: 224); (iv) HVR-H1 comprising GYX$_1$X$_2$X$_3$DX$_4$YX$_5$N, wherein $X_1$ is N or T; $X_2$ is F or V; $X_3$ is selected from the group consisting of I, M, R, and S; $X_4$ is selected from the group consisting of Y, Q, and K; and $X_5$ is I or M (SEQ ID NO: 225); (v) HVR-H2 comprising GDINX$_1$X$_2$X$_3$X$_4$X$_5$X$_6$HX$_7$X$_8$X$_9$X$_{10}$X$_{11}$X$_{12}$X$_{13}$, wherein $X_1$ is selected from the group consisting of A, L, N, and P; $X_2$ is selected from the group consisting of D, L, and R; $X_3$ is selected from the group consisting of G, K, N, R, S, and Y; $X_4$ is G or S; $X_5$ is selected from the group consisting of G, I, K, R, S, T, and V; $X_6$ is selected from the group consisting of G, R, and T; $X_7$ is selected from the group consisting of I, V, and Y; $X_8$ is N or S; $X_9$ is selected from the group consisting of A, N, and Q; $X_{10}$ is K or V; $X_{11}$ is F or Q; $X_{12}$ is K or T; and $X_{13}$ is selected from the group consisting of G, H, R, and S (SEQ ID NO: 226), and (vi) HVR-H3 comprising X$_1$REGVYHX$_2$YDDYAX$_3$DY, wherein $X_1$ is selected from the group consisting of A, N, and T; $X_2$ is D or P; and $X_3$ is M or W (SEQ ID NO: 227). In some embodiments, the anti-EGFL7 antibody comprises all six of the aforementioned HVRs. In some embodiments, HVR-L1 comprises an amino acid sequence selected from SEQ ID NOs: 100 and 106-124, HVR-L2 comprises an amino acid sequence selected from the group consisting of SEQ ID NOs: 101 and 125-129, HVR-L3 comprises an amino acid sequence selected from the group consisting of SEQ ID NOs: 102 and 130-145, HVR-H1 comprises an amino acid sequence selected from the group consisting of SEQ ID NOs: 103 and 146-153, HVR-H2 comprises an amino acid sequence selected from the group consisting of SEQ ID NOs: 104 and 154-187, and HVR-H3 comprises an amino acid sequence selected from the group consisting of SEQ ID NOs: 105 and 188-192. In some embodiments, the heavy chain comprises the following framework sequences: FR-H1 comprises EVQLVESGGGLVQPGGSLRLSCAAS (SEQ ID NO: 197); FR-H2 comprises WVRQAPGKGLEWX$_1$, wherein $X_1$ is I or V (SEQ ID NO: 228); FR-H3 comprises RX$_1$TX$_2$SX$_3$DX$_4$SX$_5$X$_6$TX$_7$YX$_8$QMNSLRAEDTAVYYC, wherein $X_1$ is F or V; $X_2$ is I or L; $X_3$ is selected from the group consisting of L, R, and V; $X_4$ is K or N; $X_5$ is selected from the group consisting of K, N, R, and S; $X_6$ is N or S; $X_7$ is selected from the group consisting of A, L, and V; and $X_8$ is L or M (SEQ ID NO: 229); and FR-H4 comprises WGQGTLVTVSS (SEQ ID NO: 200). In some embodiments, the heavy chain comprises the following framework sequences: FR-H1 comprises EVQLVESGGGLVQPGGSLRLSCAAS (SEQ ID NO: 197); FR-H2 comprises WVRQAPGKGLEWV (SEQ ID NO: 198); FR-H3 comprises RFTISRDX$_1$SKNTX$_2$YLQMNSLRAEDTAVYYCAR, wherein X$_1$ is N or K; and X$_2$ is selected from the group consisting of A, L, and V (SEQ ID NO: 230); and FR-H4 comprises WGQGTLVTVSS (SEQ ID NO: 200). In some embodiments, the light chain comprises the following framework sequences: FR-L1 comprises DIQMTQSPSSLSASVGDRVTITC (SEQ ID NO: 201), FR-L2 comprises WYQQKPGKAPKLLIY (SEQ ID NO: 202), FR-L3 comprises GVPSRFSGSGSGTDFTLTISSLQPEDFATYYC (SEQ ID NO: 203), FR-L4 comprises FGQGTKVEIK (SEQ ID NO: 221) or FGQGTKVEIKR (SEQ ID NO: 204). In some embodiments, the light chain comprises the variable domain sequence of 18F7.v6 or 18F7.v6k as shown in FIG. 27 (SEQ ID NOs: 193 and 194). In some embodiments, the heavy chain comprises the variable domain sequence of 18F7.v6 or 18F7v6k as shown in FIG. 28 (SEQ ID NOs: 195 and 196). In some embodiments, the invention provides an antibody wherein the light chain comprises the variable domain sequence of 18F7.v6 as shown in FIG. 27 (SEQ ID NO: 193) and the heavy chain comprises the variable domain sequence of 18F7.v6 as shown in FIG. 28 (SEQ ID NO: 195). In some embodiments, the invention provides an antibody wherein the light chain comprises the variable domain sequence of 18F7.v6k as shown in FIG. 27 (SEQ ID NO: 194) and the heavy chain comprises the variable domain sequence of 18F7.v6k as shown in FIG. 28 (SEQ ID NO: 196).

In some embodiments, the invention provides an antibody where at least a portion of the framework sequence is a human consensus framework sequence. In some embodiments, the antibody comprises human κ subgroup 1 consensus framework sequence. In some embodiments, the antibody comprises heavy chain human subgroup III consensus framework sequence.

In some embodiments, the invention provides an anti-EGFL7 antibody that is a bispecific antibody. In some embodiments, the bispecific antibody binds to vascular endothelial growth factor (VEGF), e.g. to the same VEGF epitope as bevacizumab or ranibizumab.

In some embodiments, the invention provides a nucleic acid encoding an antibody of the invention. In some embodiments, the invention provides a vector comprising such a nucleic acid. In some embodiments, the invention provides a host cell comprising the nucleic acid or vector.

In some embodiments, the invention provides a composition comprising an antibody of the invention. In some embodiments, the composition comprises a carrier. In some embodiments, the composition in a pharmaceutical composition.

In some embodiments, the invention provides a method for making an anti-EGFL7 antibody by expressing in a suitable host cell a vector comprising a nucleic acid encoding an antibody of the invention and recovering the antibody. In some embodiments, the host cell is prokaryotic. In some embodiments, the host cell is eukaryotic.

In some embodiments, the invention provides a method for treating a tumor, a cancer, or a cell proliferative disorder, the method comprising administering an effective amount of an anti-EGFL7 antibody of the invention to an individual in need of such treatment. In some embodiments, the invention provides an anti-EGFL7 antibody for use in the treatment of a tumor, a cancer, or a cell proliferative disorder. In some embodiments, the cancer is selected from the group consisting of breast cancer, colorectal cancer, lung cancer, esophageal cancer, bladder cancer, ovarian cancer, pancreatic cancer, and hepatocellular carcinoma. In some embodiments, the cancer is breast cancer, colorectal cancer or lung cancer. In some embodiments, the cell proliferative disorder is cancer.

In some embodiments, the treatment also comprises an effective amount of a second medicament, wherein the anti-EGFL7 antibody is a first medicament. In some embodiments, the second medicament is another antibody, a chemotherapeutic agent, a cytotoxic agent, an anti-angiogenic agent, an immunosuppressive agent, a prodrug, a cytokine, a cytokine antagonist, cytotoxic radiotherapy, a corticosteroid, an anti-emetic, a cancer vaccine, an analgesic, or a growth-inhibitory agent. In some embodiments, the second medicament is an anti-VEGF antibody, e.g. bevacizumab. In some embodiments, the second medicament is administered prior to or subsequent to the administration of the anti-EGFL7 antibody. In some embodiments, the second medicament is administered concurrently with the anti-EGFL7 antibody.

In some embodiments, the invention provides a method of reducing or inhibiting angiogenesis in a subject having a pathological condition associated with angiogenesis, comprising administering to the subject an antibody of the invention, thereby reducing or inhibiting angiogenesis in the subject. In some embodiments, the invention provides an antibody of the invention for use in the treatment of a pathological condition associated with angiogenesis. In some embodiments, the pathological condition is a neoplastic condition. In some embodiments, the pathological condition in a non-neoplastic condition. In some embodiments, the non-neoplastic condition is selected from the group consisting of diabetic and other proliferative retinopathies, retinopathy of prematurity, neovascular glaucoma, age-related macular degeneration, diabetic macular edema, corneal neovascularization, corneal graft neovascularization, retinal/choroidal neovascularization.

In some embodiments, the invention provides a method of enhancing efficacy of an anti-angiogenesis agent in a subject having a pathological condition associated with angiogenesis, comprising administering to the subject an effective amount of an antibody of the invention in combination with the anti-angiogenesis agent, thereby enhancing said anti-angiogenesis agent's inhibitory activity. In some embodiments, the invention provides an antibody of the invention for use in enhancing efficacy of an anti-angiogenesis agent in a subject having a pathological condition associated with angiogenesis. In some embodiments, the pathological condition associated with angiogenesis is a tumor, cancer or cell proliferative disorder. In some embodiments, the pathological condition associated with angiogenesis in a non-neoplastic condition. In some embodiments, the non-neoplastic condition is selected from the group consisting of diabetic and other proliferative retinopathies, retinopathy of prematurity, neovascular glaucoma, age-related macular degeneration, diabetic macular edema, corneal neovascularization, corneal graft neovascularization, retinal/choroidal neovascularization. In some embodiments, the anti-angiogenesis agent is administered prior to or subsequent to the administration of the anti-EGFL7 antibody. In some embodiments, the anti-angiogenesis agent is administered concurrently with the anti-EGFL7 antibody. In some embodiments, the anti-antigenesis agent is an anti-VEGF agent, an anti-VEGF antibody, e.g. bevacizumab or ranibizumab.

In some embodiments, the invention provides a method of reducing or inhibiting perfusion and permeability of a tumor in a subject, comprising administering to the subject an antibody of the invention. In some embodiments, the invention provides an antibody of the invention for use in reducing or inhibiting perfusion and permeability of a tumor in a subject. In some embodiments, the method or use further comprises administering an anti-angiogenesis agent, e.g. an anti-VEGF agent (e.g. an anti-VEGF antibody such as bevacizumab).

BRIEF DESCRIPTION OF THE FIGURES

FIG. 1 depicts amino acid sequences of EGFL7 from mouse (SEQ ID NO: 1) and human (SEQ ID ON: 2). The locations of the EMI1, EMI2, EGF and coiled-coiled domains are indicated. Truncated EGFL7 lacks the coiled-coiled domains. The sequence of peptides EMI1 (SEQ ID NO: 3), EMI2 (SEQ ID NO: 4) and p2 (SEQ ID NO: 5), P4 (SEQ ID NO: 6), p5 (SEQ ID NO: 7), and p6 (SEQ ID NO: 8) are underlined. Peptides EMI2 and p2 are able to prevent 4F11 binding to the truncated recombinant EGFL7 protein. Truncated huEGFL7 protein contains positions Methionine 1-Proline 182. Truncated muEGFL7 protein contains positions Methionine 1-Proline 186. The EMI1 and EMI 2 peptides are underlined with thick lines; the p2, p4, p5, and p6 peptides are underlined with thin lines.

FIG. 2 depicts the amino acid sequence of the variable light domain of the human Kappa I consensus (SEQ ID NO: 9) and 4F11.v1 (SEQ ID NO: 10). Positions are numbered according to Kabat and hypervariable regions are boxed.

FIG. 3 depicts the amino acid sequence of the variable heavy domain of the human subgroup III consensus (SEQ ID NO: 11) and 4F11.v1 (SEQ ID NO: 12). Positions are numbered according to Kabat and hypervariable regions are boxed.

FIG. 4 depicts oligonucleotides used to toggle positions in the Framework Toggle Library. The DNA sequence of 4F11.v1 and the oligonucleotides used to generate the framework toggle are shown. The amino acid sequences of the original and some resulting framework toggle regions are also shown. In some cases additional amino acid residues were also incorporated based on how the degenerate codons were designed. Sequence identifiers are shown in parentheses to the right of the corresponding sequence (SEQ ID NOs: 13-28).

FIG. 9 depicts CDR sequence changes observed in each of the 6 "single position libraries" (SPLs) for each of the 3 frameworks. Libraries were separated by framework used (4F11.v1, 4F11.v2 and 4F11.v3). Changes obtained from each of the SPLs versus the particular CDR sequence are highlighted. The VL and VH sequences outside of these changes were identical to the corresponding framework and are now shown. Sequence identifiers are shown in parentheses to the right of the corresponding sequence (SEQ ID NOs: 31-77). Individual sequences that appear more than once may not always have a corresponding sequence identifier.

FIG. 10 depicts the framework and library design for the variable light domain of limited libraries 1 and 2. The amino acid sequence of the human Kappa I consensus (SEQ ID NO: 9) and 4F11.v1 (SEQ ID NO: 10) are shown compared to the template used for library 1 (SEQ ID NO: 78) and library 2 (SEQ ID NO: 79). Positions that were randomized to all 20 amino acids are shown with slash through the amino acid.

FIG. 11 depicts the framework and library design for the variable heavy domain of limited libraries 1 and 2. The amino acid sequence of the human subgroup III consensus (SEQ ID NO: 11) and 4F11.v1 (SEQ ID NO: 12) are shown compared to the template used for library 1 (SEQ ID NO: 80) and library 2 (SEQ ID NO: 81). Positions that were randomized to all 20 amino acids are shown with slash through the amino acid.

FIG. 12 depicts the frequency of changes observed at randomized positions in limited libraries 1 and 2. The preference of amino acids selected at positions 53 and 54 in the light chain and 29, 52, and 98 in the heavy chain is shown. The preference (Sigma) for any amino acid is reported as the number of standard deviations above a random chance occurrence of a given residue in the library assuming a binomial distribution of amino acids. Scoring by this method accounts for the expected codon bias and sampling statistics when establishing a consensus.

FIG. 15 depicts the amino acid sequence of the variable light domain of the human Kappa I consensus (SEQ ID NO: 9), 4F11.v1 (SEQ ID NO: 10), 4F11.v17 (SEQ ID NO: 82), and 4F11.v22 (SEQ ID NO: 83). Positions are numbered according to Kabat and hypervariable regions (SEQ ID NOs: 234-236) are boxed.

FIG. 16 depicts the amino acid sequence of the variable heavy domain of the human subgroup III consensus (SEQ ID NO: 11), 4F11.v1 (SEQ ID NO: 12), 4F11.v17 (SEQ ID NO: 84), and 4F11.v22 (SEQ ID NO: 85; SEQ ID NOs: 238-240). Positions are numbered according to Kabat and hypervariable regions (SEQ ID NOs: 34, 35, 237) are boxed.

FIG. 17 depicts the amino acid sequence of the variable light domain of the human Kappa I consensus (SEQ ID NO: 9) and the 18F7-graft (SEQ ID NO: 86). Positions are numbered according to Kabat and hypervariable regions are boxed.

FIG. 18 depicts the amino acid sequence of the variable heavy domain of the human subgroup III consensus (SEQ ID NO: 11) and the 18F7-graft (SEQ ID NO: 87). Positions are numbered according to Kabat and hypervariable regions are boxed.

FIG. 19 depicts oligonucleotides used to toggle positions in the Framework Toggle Library. The DNA sequence of 18F7-graft and the oligonucleotides used to generate the framework toggle are shown. The amino acid sequences of the original and some resulting framework toggle regions are also shown. In some cases additional amino acid residues were also incorporated based on how the degenerate codons were designed. Sequence identifiers are shown in parentheses to the right of the corresponding sequence (SEQ ID NOs: 88-99).

FIG. 24 depicts CDR sequence changes observed in each of the 6 SPLs for each of the 3 frameworks. Libraries were separated by framework used (18F7-graft, 18F7-K, 18F7-KV, and 18F7-KA). Changes obtained from each of the SPLs versus the particular CDR sequence are highlighted. The VL and VH sequences outside of these changes were identical to the corresponding framework and are now shown. Sequence identifiers are shown in parentheses to the right of the corresponding sequence (SEQ ID NOs: 100-192). Individual sequences that appear more than once may not always have a corresponding sequence identifier.

FIG. 27 depicts the amino acid sequence of the variable light domain of the human Kappa I consensus (SEQ ID NO: 9), 18F7.v6 (SEQ ID NO: 193), and 18F7.v6k (SEQ ID NO: 194). Positions are numbered according to Kabat and hypervariable regions (SEQ ID NOs: 241, 101, 131) are boxed. Where sequence for 18F7.v6k is not shown (in the second and third parts of the alignment), the corresponding sequence is identical to the sequence for 18F7.v6.

DETAILED DESCRIPTION OF THE INVENTION

Figure 5:
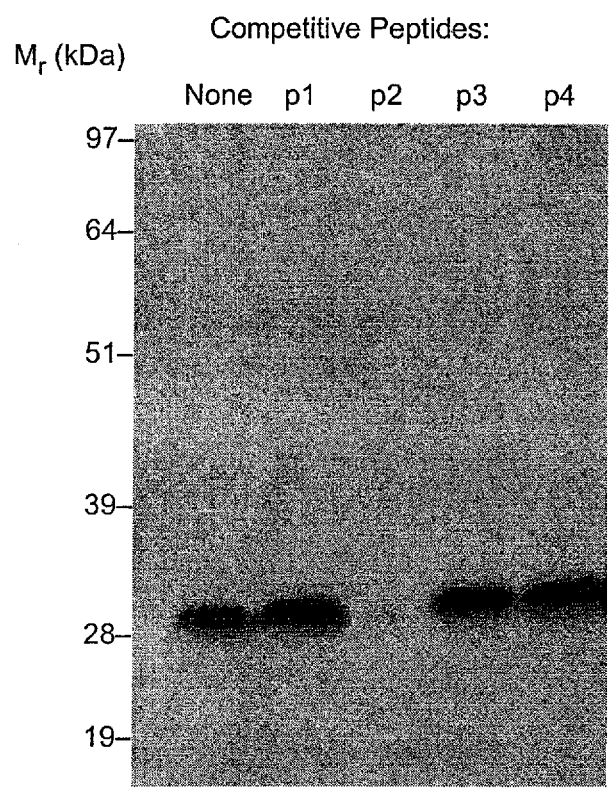
FIG. 5 depicts results demonstrating that mu4F11 binding to EGFL7 can be blocked by Peptide 2 (SEQ ID NO: 5), but not by overlapping Peptides 1 or 3 (SEQ ID NOs: 29 and 30, respectively) or a random control peptide. Cell lysates from 293 cells transfected with hEGfl7-His were immunoprecipitated with 4F11 in the presence or absence of different Peptides. Peptide 1: RSPGLAPARPRYA (SEQ ID NO: 29). Peptide 2: RPRYACCPGWKRT (SEQ ID NO: 5). Peptide 3: GWKRTSGLPGACG (SEQ ID NO: 30). Peptide 4: random control peptide.

The invention provides methods, compositions, kits and articles of manufacture for anti-EGFL7 antibodies.

Details of these methods, compositions, kits and articles of manufacture are provided herein.

General Techniques

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "anti-EGFL7 antibody" or "an antibody that binds to EGFL7" refers to an antibody that is capable of binding EGFL7 with sufficient affinity such that the antibody is useful as a diagnostic and/or therapeutic agent in targeting EGFL7. In certain embodiments, an antibody that binds to EGFL7 has a dissociation constant (Kd) of ≤1 µM, ≤100 nM, ≤10 nM, ≤1 nM, or ≤0.1 nM.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol Biol 293: 865-881). To establish conditions for the assay, microtiter plates (Dynex) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween™-20 in PBS. When the plates have dried, 150 µl/well of scintillant (MicroScint™-20; Packard) is added, and the plates are counted on a TopCount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10mM sodium acetate, pH 4.8, into 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween™ 20 (PBST) at 25° C. at a flow rate of approximately 25 µl/min. Association rates ($k_{on}$) and dissociation rates ($k_{off}$) are calculated using a simple one-to-one Langmuir binding model (BIAcore™ Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol. Biol. 293:865-881. If the on-rate exceeds $10^6 M^{-1} S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM Aminco spectrophotometer (ThermoSpectronic) with a stirred cuvette.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors" or "expression vectors"). In general, expression vectors of utility in recombinant DNA techniques are often in the form of plasmids. In the present specification, "plasmid" and "vector" may be used interchangeably.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O) R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "EGFL7" (interchangeably termed "EGF-like-domain, multiple 7"), as used herein, refers, unless specifically or contextually indicated otherwise, to any native or variant (whether native or synthetic) EGFL7 polypeptide. The term "native sequence" specifically encompasses naturally occurring truncated or secreted forms (e.g., an extracellular domain sequence), naturally occurring variant forms (e.g., alternatively spliced forms) and naturally-occurring allelic variants. The term "wild type EGFL7" generally refers to a polypeptide comprising the amino acid sequence of a naturally occurring EGFL7 protein. The term "wild type EGFL7 sequence" generally refers to an amino acid sequence found in a naturally occurring EGFL7.

The terms "antibody" and "immunoglobulin" are used interchangeably in the broadest sense and include monoclonal antibodies (for e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions or hypervariable regions (CDRs or HVRs, used interchangeably herein) both in the light-chain and the heavy-chain variable domains. The more highly conserved portions of variable domains are called the framework (FR). The variable domains of native heavy and light chains each comprise four FR regions, largely adopting a β-sheet configuration, connected by three HVRs, which form loops connecting, and in some cases forming part of, the β-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, and IgA$_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature,* 256:495-97 (1975); Hongo et al., *Hybridoma,* 14 (3): 253-260 (1995), Harlow et al., *Antibodies: A Laboratory Manual,* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816, 567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in *The Pharmacology of Monoclonal Antibodies,* vol. 113, Rosenburg and Moore eds., Springer-Verlag, New York, pp. 269-315 (1994).

An "antigen" is a predetermined antigen to which an antibody can selectively bind. The target antigen may be polypeptide, carbohydrate, nucleic acid, lipid, hapten or other naturally occurring or synthetic compound.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993). Triabodies and tetrabodies are also described in Hudson et al., *Nat. Med.* 9:129-134 (2003).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227:381 (1991); Marks et al., *J. Mol. Biol.,* 222:581 (1991). Also available for the preparation of human monoclonal antibodies are methods described in Cole et al., *Monoclonal Antibodies and Cancer Therapy,* Alan R. Liss, p. 77 (1985); Boerner et al., *J. Immunol.,* 147 (1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

A "blocking" antibody or an "antagonist" antibody is one which inhibits or reduces biological activity of the antigen it binds. Certain blocking antibodies or antagonist antibodies substantially or completely inhibit the biological activity of the antigen.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology*, 15(7):637-640 (1997); Hinton et al., *J. Biol. Chem.* 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS (USA)* 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. *J. Immunol.* 164: 4178-4184 (2000).

The term "Fc region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this invention can comprise an antibody with K447, with all K447 removed, or a mixture of antibodies with and without the K447 residue.

An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences:

```
                                       (SEQ ID NO: 197)
    EVQLVESGGGLVQPGGSLRLSCAAS- (SEQ ID NO: 198)
    H1-WVRQAPGKGLEWV- (SEQ ID NO: 199
    H2-RFTISRDNSKNTLYLQMNSLRAEDTAVYYC- (SEQ ID NO: 200)
    H3-WGQGTLVTVSS.
```

A "VL subgroup I consensus framework" comprises the consensus sequence obtained from the amino acid sequences in variable light kappa subgroup I of Kabat et al. In one embodiment, the VH subgroup I consensus framework amino acid sequence comprises at least a portion or all of each of the following sequences:

```
                                       (SEQ ID NO: 201)
    DIQMTQSPSSLSASVGDRVTITC- (SEQ ID NO: 202)
    L1-WYQQKPGKAPKLLIY- (SEQ ID NO: 203)
    L2-GVPSRFSGSGSGTDFTLTISSLQPEDFATYYC- (SEQ ID NO: 221)
    L3-FGQGTKVEIK.
```

A "biological sample" (interchangeably termed "sample" or "tissue or cell sample") encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention. In some embodiments, the same section of tissue sample is analyzed at both morphological and molecular levels, or is analyzed with respect to both protein and nucleic acid.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

A "medicament" is an active drug to treat the disorder in question or its symptoms, or side effects.

A "disorder" or "disease" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; carcinoma, blastoma, and sarcoma.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer. Dysregulation of angiogenesis can lead to many disorders that can be treated by compositions and methods of the invention. These disorders include both non-neoplastic and neoplastic conditions. Neoplastics include but are not limited those described above. Non-neoplastic disorders include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

The term "wasting" disorders (e.g., wasting syndrome, cachexia, sarcopenia) refers to a disorder caused by undesirable and/or unhealthy loss of weight or loss of body cell mass. In the elderly as well as in AIDS and cancer patients, wasting disease can result in undesired loss of body weight, including both the fat and the fat-free compartments. Wasting diseases can be the result of inadequate intake of food and/or metabolic changes related to illness and/or the aging process. Cancer patients and AIDS patients, as well as patients following extensive surgery or having chronic infections, immunologic diseases, hyperthyroidism, Crohn's disease, psychogenic disease, chronic heart failure or other severe trauma, frequently suffer from wasting disease which is sometimes also referred to as cachexia, a metabolic and, sometimes, an eating disorder. Cachexia is additionally characterized by hypermetabolism and hypercatabolism. Although cachexia and wasting disease are frequently used interchangeably to refer to wasting conditions, there is at least one body of research which differentiates cachexia from wasting syndrome as a loss of fat-free mass, and particularly, body cell mass (Mayer, 1999, J. Nutr. 129(1S Suppl.):256S-259S). Sarcopenia, yet another such disorder which can affect the aging individual, is typically characterized by loss of muscle mass. End stage wasting disease as described above can develop in individuals suffering from either cachexia or sarcopenia.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or disorder.

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. For example, an anti-angiogenesis agent is an antibody or other antagonist to an angiogenic agent as defined above, e.g., antibodies to VEGF, antibodies to VEGF receptors, small molecules that block VEGF receptor signaling (e.g., PTK787/ZK2284, SU6668, SUTENT®/SU11248 (sunitinib malate), AMG706). Anti-angiogenesis agents also include native angiogenesis inhibitors, e.g., angiostatin, endostatin, etc. See, e.g., Klagsbrun and D'Amore, Annu. Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5(12): 1359-1364 (1999); Tonini et al., Oncogene, 22:6549-6556 (2003) (e.g., Table 2 listing antiangiogenic factors); and, Sato Int. J. Clin. Oncol., 8:200-206 (2003) (e.g., Table 1 lists Anti-angiogenic agents used in clinical trials).

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutensing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

A "growth inhibitory agent" when used herein refers to a compound or composition which inhibits growth of a cell (such as a cell expressing EGFL7) either in vitro or in vivo. Thus, the growth inhibitory agent may be one which significantly reduces the percentage of cells (such as a cell expressing EGFL7) in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "Fc region-comprising polypeptide" refers to a polypeptide, such as an antibody or immunoadhesin (see definitions below), which comprises an Fc region. The C-terminal lysine (residue 447 according to the EU numbering system) of the Fc region may be removed, for example, during purification of the polypeptide or by recombinant engineering the nucleic acid encoding the polypeptide. Accordingly, a composition comprising a polypeptide having an Fc region according to this invention can comprise polypeptides with K447, with all K447 removed, or a mixture of polypeptides with and without the K447 residue.

Throughout this specification and claims, the word "comprise," or variations such as "comprises" or "comprising," will be understood to imply the inclusion of a stated integer or group of integers but not the exclusion of any other integer or group of integers.

Generatin Variant Antibodies Exhibitin Reduced or Absence of HAMA Response

Reduction or elimination of a HAMA response is a significant aspect of clinical development of suitable therapeutic agents. See, e.g., Khaxzaeli et al., J. Natl. Cancer Inst. (1988), 80:937; Jaffers et al., Transplantation (1986), 41:572; Shawler et al., J. Immunol. (1985), 135:1530; Sears et al., J. Biol. Response Mod. (1984), 3:138; Miller et al., Blood (1983), 62:988; Hakimi et al., J. Immunol. (1991), 147:1352; Reichmann et al., Nature (1988), 332:323; Junghans et al., Cancer Res. (1990), 50:1495. As described herein, the invention provides antibodies that are humanized such that HAMA response is reduced or eliminated. Variants of these antibodies can further be obtained using routine methods known in the art, some of which are further described below.

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), preferably the acceptor human frameworks are from, or derived from, a human consensus framework sequence as such frameworks have been demonstrated to have minimal, or no, immunogenicity in human patients.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor.

In one embodiment, human consensus frameworks herein are from, or derived from, VH subgroup III and/or VL kappa subgroup I consensus framework sequences.

Thus, the VH acceptor human framework may comprise one, two, three or all of the following framework sequences:

```
                                            (SEQ ID NO: 197)
FR1 comprising EVQLVESGGGLVQPGGSLRLSCAAS, (SEQ ID NO: 198)
FR2 comprising WVRQAPGKGLEWV, (SEQ ID NO: 205)
FR3 comprising FR3 comprises
RFTISX₁DX₂SKNTX₃YLQMNSLRAEDTAVYYC, wherein X₁ is A or R, X₂ is T or N, and X₃ is A or
L, (SEQ ID NO: 200)
FR4 comprising WGQGTLVTVSS.
```

In one embodiment, the VH acceptor human framework comprises one, two, three or all of the following framework sequences:

```
                                            (SEQ ID NO: 197)
  FR1 comprising EVQLVESGGGLVQPGGSLRLSCAAS, (SEQ ID NO: 198)
  FR2 comprising WVRQAPGKGLEWV, (SEQ ID NO: 231)
  FR3 comprising RFTISADTSKNTAYLQMNSLRAEDTAVYYC, (SEQ ID NO: 206)
  RFTISADTSKNTAYLQMNSLRAEDTAVYYCA, (SEQ ID NO: 207)
  RFTISADTSKNTAYLQMNSLRAEDTAVYYCAR, (SEQ ID NO: 208)
  RFTISADTSKNTAYLQMNSLRAEDTAVYYCS,
  or
```

```
                                            (SEQ ID NO: 209)
  RFTISADTSKNTAYLQMNSLRAEDTAVYYCSR (SEQ ID NO: 200)
  FR4 comprising WGQGTLVTVSS.
```

The VL acceptor human framework may comprise one, two, three or all of the following framework sequences:

```
                                            (SEQ ID NO: 201)
FR1 comprising DIQMTQSPSSLSASVGDRVTITC, (SEQ ID NO: 202)
FR2 comprising WYQQKPGKAPKLLIY, (SEQ ID NO: 203)
FR3 comprising GVPSRFSGSGSGTDFTLTISSLQPEDFATYYC, (SEQ ID NO: 221)
FR4 comprising FGQGTKVEIK.
```

While the acceptor may be identical in sequence to the human framework sequence selected, whether that is from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

Hypervariable region residues of the non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-34 (L1), 50-56 (L2) and 89-97 (L3), 26-35 (H1), 50-65 or 49-65 (H2) and 93-102, 94-102, or 95-102 (H3).

While "incorporation" of hypervariable region residues is discussed herein, it will be appreciated that this can be achieved in various ways, for example, nucleic acid encoding the desired amino acid sequence can be generated by mutating nucleic acid encoding the mouse variable domain sequence so that the framework residues thereof are changed to acceptor human framework residues, or by mutating nucleic acid encoding the human variable domain sequence so that the hypervariable domain residues are changed to non-human residues, or by synthesizing nucleic acid encoding the desired sequence, etc.

In the examples herein, hypervariable region-grafted variants were generated by Kunkel mutagenesis of nucleic acid encoding the human acceptor sequences, using a separate oligonucleotide for each hypervariable region. Kunkel et al., *Methods Enzymol.* 154:367-382 (1987). Appropriate changes can be introduced within the framework and/or hypervariable region, using routine techniques, to correct and re-establish proper hypervariable region-antigen interactions.

Phage(mid) display (also referred to herein as phage display in some contexts) can be used as a convenient and fast method for generating and screening many different potential variant antibodies in a library generated by sequence randomization. However, other methods for making and screening altered antibodies are available to the skilled person.

Phage(mid) display technology has provided a powerful tool for generating and selecting novel proteins which bind to a ligand, such as an antigen. Using the techniques of phage (mid) display allows the generation of large libraries of protein variants which can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phagemid display systems where the nucleic acid sequence encoding the protein or polypeptide is fused to a nucleic acid sequence encoding a portion of the gene III protein have been developed. (Bass, S., *Proteins*, 8:309 (1990); Lowman and Wells, *Methods: A Companion to Methods in Enzymology*, 3:205 (1991)). In a monovalent phagemid display system, the gene fusion is expressed at low levels and wild type gene III proteins are also expressed so that infectivity of the particles is retained. Methods of generating peptide libraries and screening those libraries have been disclosed in many patents (e.g. U.S. Pat. No. 5,723,286, U.S. Pat. No. 5,432,018, U.S. Pat. No. 5,580,717, U.S. Pat. No. 5,427,908 and U.S. Pat. No. 5,498,530).

Libraries of antibodies or antigen binding polypeptides have been prepared in a number of ways including by altering a single gene by inserting random DNA sequences or by cloning a family of related genes. Methods for displaying antibodies or antigen binding fragments using phage(mid) display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with the desired characteristics.

Methods of substituting an amino acid of choice into a template nucleic acid are well established in the art, some of which are described herein. For example, hypervariable region residues can be substituted using the Kunkel method. See, e.g., Kunkel et al., *Methods Enzymol.* 154:367-382 (1987).

The sequence of oligonucleotides includes one or more of the designed codon sets for the hypervariable region residues to be altered. A codon set is a set of different nucleotide triplet sequences used to encode desired variant amino acids. Codon sets can be represented using symbols to designate particular nucleotides or equimolar mixtures of nucleotides as shown in below according to the IUB code.

IUB CODES
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T)
N (A or C or G or T)

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al. *Nucleic Acids Res.* 10:6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., *Proc. Nat'l. Acad. Sci. USA*, 75:5765 (1978).

The DNA template is generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. coli* JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. *Meth. Enzymol.*, 153:3 (1987). Thus, the DNA that is to be mutated must be inserted into one of these vectors in order to generate single-stranded template. Production of the single-stranded template is described in sections 4.21-4.41 of Sambrook et al., supra.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

The sequence of the PCR primers includes one or more of the designed codon sets for the solvent accessible and highly diverse positions in a hypervariable region. As described above, a codon set is a set of different nucleotide triplet sequences used to encode desired variant amino acids.

Antibody selectants that meet the desired criteria, as selected through appropriate screening/selection steps can be isolated and cloned using standard recombinant techniques.

Antibody Fragments

The present invention encompasses antibody fragments. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, supra. The antibody fragment may also be a "linear antibody", e.g., as described in U.S. Pat. No. 5,641,870, for example. Such linear antibodies may be monospecific or bispecific.

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies. See, e.g., Carter et al. (1992) *Proc. Natl. Acad. Sci. USA*, 89:4285; Presta et al. (1993) *J. Immunol.*, 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human antibodies of the invention can be constructed by combining Fv clone variable domain sequence(s) selected from human-derived phage display libraries with known human constant domain sequences(s) as described above. Alternatively, human monoclonal antibodies of the invention can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci USA*, 90: 2551 (1993); Jakobovits et al., *Nature*, 362: 255 (1993); Bruggermann et al., *Year in Immunol.*, 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by HVR grafting, this technique provides completely human antibodies, which have no FR or HVR residues of non-human origin.

Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for EGFL7 and the other is for any other antigen. In certain embodiments, the other antigen is vascular endothelial growth factor (VEGF), e.g. the epitope bound by the antibodies bevacizumab and ranibizumab. In certain embodiments, the bispecific antibody has a first arm comprising the HVR sequences of an antibody of the invention and a second arm comprising the HVR sequences of bevacizumab or ranibizumab. In certain embodiments, the bispecific antibody comprises the VH and VL sequences of bevacizumab or ranibizumab. In certain embodiments, bispecific antibodies may bind to two different epitopes of EGFL7. Bispecific antibodies may also be used to localize cytotoxic agents to cells which express EGFL7. These antibodies possess a EGFL7-binding arm and an arm which binds a cytotoxic agent, such as, e.g., saporin, anti-interferon-$\alpha$, vinca alkaloid, ricin A chain, methotrexate or radioactive isotope hapten. Bispecific antibodies can be prepared as full length antibodies or antibody fragments (e.g. F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature*, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.*, 10: 3655 (1991).

According to a different approach, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach, the interface between a pair of antibody molecules can be engineered to maximize the percentage of heterodimers which are recovered from recombinant cell culture. The interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/00373, and EP 03089). Heteroconjugate antibodies may be made using any convenient cross-linking method. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

Antibody Variants

In some embodiments, amino acid sequence modification (s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science*, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. (1997) *TIBTECH* 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

For example, antibody variants are provided having a carbohydrate structure that lacks fucose attached (directly or indirectly) to an Fc region. Such variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336: 1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, an antibody variant comprises an Fc region with one or more amino acid substitutions which further improve ADCC, for example, substitutions at positions 298, 333, and/or 334 of the Fc region (Eu numbering of residues). Such substitutions may occur in combination with any of the variations described above.

In certain embodiments, the invention contemplates an antibody variant that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). Non-limiting examples of in vitro assays to assess ADCC activity of a molecule of interest is described in U.S. Pat. No. 5,500,362 (see, e.g. Hellstrom, I., et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. To assess complement activation, a CDC assay may be performed (see, for example, Gazzano-Santoro et al., *J. Immunol. Methods* 202: 163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, for example, Petkova, S. B. et al., *Int'l. Immunol.* 18(12):1759-1769 (2006)).

Other antibody variants having one or more amino acid substitutions are provided. Sites of interest for substitutional mutagenesis include the hypervariable regions, but FR alterations are also contemplated. Conservative substitutions are shown in Table 1 under the heading of "preferred substitutions." More substantial changes, denominated "exemplary substitutions" are provided in the "Amino Acid Substitution Table", or as further described below in reference to amino acid classes. Amino acid substitutions may be introduced into an antibody of interest and the products screened, e.g., for a desired activity, such as improved antigen binding, decreased immunogenicity, improved ADCC or CDC, etc.

Amino Acid Substitution Table

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His(H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. An exemplary substitutional variant is an affinity matured antibody, which may be conveniently generated using phage display-based affinity maturation techniques. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and variants with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter, *Nature* 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. See, also, Shields et al. *J. Biol. Chem.* 9(2): 6591-6604 (2001). Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. See, also, Idusogie et al. *J. Immunol.* 164: 4178-4184 (2000).

In another aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

In yet another aspect, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region.

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Activity Assays

The antibodies of the present invention can be characterized for their physical/chemical properties and biological functions by various assays known in the art.

In one aspect, assays are provided for identifying anti-EGFL7 antibodies thereof having biological activity. Biological activity may include, e.g., the modulation of one or more aspects of EGFL7-associated effects, including but not limited to EGFL7 binding, EGFL7-mediated protection of endothelial cells under hypoxic stress, and the ability of EGFL7 to mediate endothelial cell adhesion.

In certain embodiments of the invention, the immunoglobulins produced herein are analyzed for their biological activity. In some embodiments, the immunoglobulins of the present invention are tested for their antigen binding activity. The antigen binding assays that are known in the art and can be used herein include without limitation any direct or competitive binding assays using techniques such as western blots, radioimmunoassays, ELISA (enzyme linked immnosorbent assay), "sandwich" immunoassays, immunoprecipitation assays, fluorescent immunoassays, and protein A immunoassays. An illustrative antigen binding assay is provided below in the Examples section.

The purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In some embodiments, the present invention contemplates altered antibodies that possess some but not all effector functions, which make it a desired candidate for many applications in which the half life of the antibody in vivo is important yet certain effector functions (such as complement and ADCC) are unnecessary or deleterious. In certain embodiments, the Fc activities of the produced immunoglobulin are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). An example of an in vitro assay to assess ADCC activity of a molecule of interest is described in U.S. Pat. Nos. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, e.g. as described in Gazzano-Santoro et al., J. Immunol. Methods 202:163 (1996), may be performed. FcRn binding and in vivo clearance/half life determinations can also be performed using methods known in the art.

In some embodiments, the invention provides altered antibodies that possess increased effector functions and/or increased half-life.

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

a. Generating Antibodies Using Prokaryotic Host Cells:
   i. Vector Construction Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB- strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies of the invention include Archaebacteria and Eubacteria, such as Gram-negative or Gram-positive organisms. Examples of useful bacteria include Escherichia (e.g., E. coli), Bacilli (e.g., B. subtilis), Enterobacteria, Pseudomonas species (e.g., P. aeruginosa), Salmonella typhimurium, Serratia marcescans, Klebsiella, Proteus, Shigella, Rhizobia, Vitreoscilla, or Paracoccus. In one embodiment, gram-negative cells are used. In one embodiment, E. coli cells are used as hosts for the invention. Examples of E. coli strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as E. coli 294 (ATCC® 31,446), E. coli B, E. coli λ 1776 (ATCC® 31,537) and E. coli RV308 (ATCC® 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, E. coli, Serratia, or Salmonella species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For E. coli growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For E. coli, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex® G-75.

In one aspect, Protein A immobilized on a solid phase is used for immunoaffinity purification of the full length antibody products of the invention. Protein A is a 41 kD cell wall protein from *Staphylococcus aureas* which binds with a high affinity to the Fc region of antibodies. Lindmark et al (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

b. Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC® CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT (SEQ ID NO: 232) region where N may be any nucleotide. At the 3' end of most eukaryotic genes is an AATAAA (SEQ ID NO: 233) sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC® CRL 1651); human embryonic kidney line (293 or 293 cells subcloned for growth in suspension culture, Graham et al., J. Gen Virol. 36:59 (1977)); baby hamster kidney cells (BHK, ATCC® CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC® CCL 70); African green monkey kidney cells (VERO-76, ATCC® CRL-1587); human cervical carcinoma cells (HELA, ATCC® CCL 2); canine kidney cells (MDCK, ATCC® CCL 34); buffalo rat liver cells (BRL 3A, ATCC® CRL 1442); human lung cells (W138, ATCC® CCL 75); human liver cells (Hep G2, HB 8065); mouse mammary tumor (MMT 060562, ATCC® CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Immunoconjugates

The invention also provides immunoconjugates (interchangeably referred to as "antibody-drug conjugates," or "ADCs") comprising an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

Immunoconjugates have been used for the local delivery of cytotoxic agents, i.e., drugs that kill or inhibit the growth or proliferation of cells, in the treatment of cancer (Lambert, J. (2005) Curr. Opinion in Pharmacology 5:543-549; Wu et al (2005) Nature Biotechnology 23(9):1137-1146; Payne, G. (2003) i 3:207-212; Syrigos and Epenetos (1999) Anticancer Research 19:605-614; Niculescu-Duvaz and Springer (1997) Adv. Drug Deliv. Rev. 26:151-172; U.S. Pat. No. 4,975,278). Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Baldwin et al., Lancet (Mar. 15, 1986) pp. 603-05; Thorpe (1985) "Antibody Carriers Of Cytotoxic Agents In Cancer Therapy: A Review," in Monoclonal Antibodies '84: Biological And Clinical Applications (A. Pinchera et al., eds) pp. 475-506. Both polyclonal antibodies and monoclonal antibodies have been reported as useful in these strategies (Rowland et al., (1986) Cancer Immunol. Immunother. 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may exert their cytotoxic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111In or 90Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody-drug conjugate composed of a huCD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody-drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and other cancers. MLN-2704 (Millennium Pharm., BZL Biologics, Immunogen Inc.), an antibody-drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnol. 21(7):778-784) and are under therapeutic development.

In certain embodiments, an immunoconjugate comprises an antibody and a chemotherapeutic agent or other toxin. Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

Maytansine and Maytansinoids

In some embodiments, the immunoconjugate comprises an antibody (full length or fragments) conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10_5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and non-patent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolastatins

In some embodiments, the immunoconjugate comprises an antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998)

Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", U.S. Ser. No. 10/983, 340, filed Nov. 5, 2004 (disclosing, e.g., linkers and methods of preparing monomethylvaline compounds such as MMAE and MMAF conjugated to linkers).

Calicheamicin

In other embodiments, the immunoconjugate comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma 1I$, $\alpha 2I$, $\alpha 3I$, N-acetyl-$\gamma 1I$, PSAG and $\theta I1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99}m$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as his (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC), an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab\text{-}(L\text{-}D)_p \quad\quad\quad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC'), and N-Succinimidyl (4-iodo-acetyl) aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Pharmaceutical Formulations

Therapeutic formulations comprising an antibody of the invention are prepared for storage by mixing the antibody having the desired degree of purity with optional physiologically acceptable carriers, excipients or stabilizers (*Remington: The Science and Practice of Pharmacy* 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington: The Science and Practice of Pharmacy* 20th edition (2000).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L- glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the present invention may be used in, for example, in vitro, ex vivo and in vivo therapeutic methods.

The invention provides methods and compositions useful for modulating disease states associated with expression and/or activity of EGFL7, such as increased expression and/or activity or undesired expression and/or activity, said methods comprising administration of an effective dose of an anti-EGFL7 antibody to an individual in need of such treatment.

In one aspect, the invention provides methods for treating or preventing a tumor, a cancer, and/or a cell proliferative disorder, the methods comprising administering an effective amount of an anti-EGFL7 antibody to an individual in need of such treatment.

In one aspect, the invention provides methods for inhibiting angiogenesis, the methods comprising administering an effective amount of an anti-EGFL7 antibody to an individual in need of such treatment.

In one aspect, the invention provides methods for enhancing the efficacy of another anti-angiogenic agent, the methods comprising administering an effective amount of an anti-EGFL7 antibody to an individual in need of such treatment. In some embodiments, the individual has a tumor, a cancer, and/or a cell proliferative disorder. In some embodiments, the other anti-angiogenic agent targets VEGF, e.g. an anti-VEGF antibody.

It is understood that any suitable anti-EGFL7 antibody may be used in methods of treatment, including monoclonal and/or polyclonal antibodies, a human antibody, a chimeric antibody, an affinity-matured antibody, a humanized antibody, and/or an antibody fragment. In some embodiments, any anti-EGFL7 antibody described herein is used for treatment.

In any of the methods herein, one may administer to the subject or patient along with the antibody herein an effective amount of a second medicament (where the antibody herein is a first medicament), which is another active agent that can treat the condition in the subject that requires treatment. For instance, an antibody of the invention may be co-administered with another antibody, chemotherapeutic agent(s) (including cocktails of chemotherapeutic agents), anti-angiogenic agent(s), immunosuppressive agents(s), cytokine(s), cytokine antagonist(s), and/or growth-inhibitory agent(s). The type of such second medicament depends on various factors, including the type of disorder, the severity of the disease, the condition and age of the patient, the type and dose of first medicament employed, etc.

Where an antibody of the invention inhibits tumor growth, for example, it may be particularly desirable to combine it with one or more other therapeutic agents that also inhibit tumor growth. For instance, an antibody of the invention may be combined with an anti-angiogenic agent, such as an anti-VEGF antibody (e.g., AVASTIN®) and/or anti-ErbB antibodies (e.g. HERCEPTIN® trastuzumab anti-HER2 antibody or an anti-HER2 antibody that binds to Domain II of HER2, such as OMNITARG™ pertuzumab anti-HER2 antibody) in a treatment scheme, e.g. in treating any of the disease described herein, including colorectal cancer, lung cancer, hepatocellular carcinoma, breast cancer and/or pancreatic cancer. In some instances, the previous combinations may be accomplished using a bispecific antibody. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the antibody of the invention can occur prior to, and/or following, administration of the adjunct therapy or therapies. In addition, combining an antibody of this invention with a relatively non-cytotoxic agent such as another biologic molecule, e.g., another antibody is expected to reduce cytotoxicity versus combining the antibody with a chemotherapeutic agent of other agent that is highly toxic to cells.

Treatment with a combination of the antibody herein with one or more second medicaments preferably results in an improvement in the signs or symptoms of cancer. For instance, such therapy may result in an improvement in survival (overall survival and/or progression-free survival) relative to a patient treated with the second medicament only (e.g., a chemotherapeutic agent only), and/or may result in an objective response *(partial or complete, preferably complete). Moreover, treatment with the combination of an antibody herein and one or more second medicament(s) preferably results in an additive, and more preferably synergistic (or greater than additive), therapeutic benefit to the patient. Preferably, in this combination method the timing between at least one administration of the second medicament and at least one administration of the antibody herein is about one month or less, more preferably, about two weeks or less.

For treatment of cancers, the second medicament is preferably another antibody, chemotherapeutic agent (including cocktails of chemotherapeutic agents), anti-angiogenic agent, immunosuppressive agent, prodrug, cytokine, cytokine antagonist, cytotoxic radiotherapy, corticosteroid, anti-emetic, cancer vaccine, analgesic, anti-vascular agent, and/or growth-inhibitory agent. The cytotoxic agent includes an agent interacting with DNA, the antimetabolites, the topoisomerase I or II inhibitors, or the spindle inhibitor or stabilizer agents (e.g., preferably vinca alkaloid, more preferably selected from vinblastine, deoxyvinblastine, vincristine, vindesine, vinorelbine, vinepidine, vinfosiltine, vinzolidine and vinfunine), or any agent used in chemotherapy such as 5-FU, a taxane, doxorubicin, or dexamethasone.

In some embodiments, the second medicament is another antibody used to treat cancers such as those directed against the extracellular domain of the HER2/neu receptor, e.g., trastuzumab, or one of its functional fragments, pan-HER inhibitor, a Src inhibitor, a MEK inhibitor, or an EGFR inhibitor (e.g., an anti-EGFR antibody (such as one inhibiting the tyrosine kinase activity of the EGFR), which is preferably the mouse monoclonal antibody 225, its mouse-man chimeric derivative C225, or a humanized antibody derived from this antibody 225 or derived natural agents, dianilinophthalimides, pyrazolo- or pyrrolopyridopyrimidines, quinazilines, gefitinib, erlotinib, cetuximab, ABX-EFG, canertinib, EKB-569 and PKI-166), or dual-EGFR/HER-2 inhibitor such as lapatanib. Additional second medicaments include alemtuzumab (CAMPATH™), FavID (IDKLH), CD20 antibodies with altered glycosylation, such as GA-101/GLYCART™, oblimersen (GENASENSE™), thalidomide and analogs thereof, such as lenalidomide (REVLIMID™), imatinib, sorafenib, ofatumumab (HUMAX-CD20™), anti-CD40 antibody, e.g. SGN-40, and anti-CD-80 antibody, e.g. galiximab.

The anti-emetic agent is preferably ondansetron hydrochloride, granisetron hydrochloride, metroclopramide, domperidone, haloperidol, cyclizine, lorazepam, prochlorperazine, dexamethasone, levomepromazine, or tropisetron. The vaccine is preferably GM-CSF DNA and cell-based vaccines, dendritic cell vaccine, recombinant viral vaccines, heat shock protein (HSP) vaccines, allogeneic or autologous tumor vaccines. The analgesic agent preferably is ibuprofen, naproxen, choline magnesium trisalicylate, or oxycodone hydrochloride. The anti-vascular agent preferably is bevacizumab, or rhuMAb-VEGF. Further second medicaments include antiproliferative agents such a farnesyl protein transferase inhibitors, anti-VEGF inhibitors, p53 inhibitors, or PDGFR inhibitors. The second medicament herein includes also biologic-targeted therapy such as treatment with antibodies as well as small-molecule-targeted therapy, for example, against certain receptors.

Many anti-angiogenic agents have been identified and are known in the art, including those listed herein, e.g., listed under Definitions, and by, e.g., Carmeliet and Jain, Nature 407:249-257 (2000); Ferrara et al., Nature Reviews:Drug Discovery, 3:391-400 (2004); and Sato Int. J. Clin. Oncol., 8:200-206 (2003). See also, US Patent Application US20030055006. In one embodiment, an anti-EGFL7 antibody is used in combination with an anti-VEGF neutralizing antibody (or fragment) and/or another VEGF antagonist or a VEGF receptor antagonist including, but not limited to, for example, soluble VEGF receptor (e.g., VEGFR-1, VEGFR-2, VEGFR-3, neuropilins (e.g., NRP1, NRP2)) fragments, aptamers capable of blocking VEGF or VEGFR, neutralizing anti-VEGFR antibodies, low molecule weight inhibitors of VEGFR tyrosine kinases (RTK), antisense strategies for VEGF, ribozymes against VEGF or VEGF receptors, antagonist variants of VEGF; and any combinations thereof. Alternatively, or additionally, two or more angiogenesis inhibitors may optionally be co-administered to the patient in addition to VEGF antagonist and other agent. In certain embodiment, one or more additional therapeutic agents, e.g., anti-cancer agents, can be administered in combination with anti-EGFL7 antibody, the VEGF antagonist, and an anti-angiogenesis agent.

Chemotherapeutic agents useful herein are described supra, e.g., in the definition of "chemotherapeutic agent".

Such second medicaments may be administered within 48 hours after the antibodies herein are administered, or within 24 hours, or within 12 hours, or within 3-12 hours after said agent, or may be administered over a pre-selected period of time, which is preferably about 1 to 2 days. Further, the dose of such agent may be sub-therapeutic.

The antibodies herein can be administered concurrently, sequentially, or alternating with the second medicament or upon non-responsiveness with other therapy. Thus, the combined administration of a second medicament includes co-administration (concurrent administration), using separate formulations or a single pharmaceutical formulation, and consecutive administration in either order, wherein preferably there is a time period while both (or all) medicaments simultaneously exert their biological activities. All these second medicaments may be used in combination with each other or by themselves with the first medicament, so that the express "second medicament" as used herein does not mean it is the only medicament besides the first medicament, respectively. Thus, the second medicament need not be one medicament, but may constitute or comprise more than one such drug.

These second medicaments as set forth herein are generally used in the same dosages and with administration routes as the first medicaments, or about from 1 to 99% of the dosages of the first medicaments. If such second medicaments are used at all, preferably, they are used in lower amounts than if the first medicament were not present, especially in subsequent dosings beyond the initial dosing with the first medicament, so as to eliminate or reduce side effects caused thereby.

The invention also provides methods and compositions for inhibiting or preventing relapse tumor growth or relapse cancer cell growth. Relapse tumor growth or relapse cancer cell growth is used to describe a condition in which patients undergoing or treated with one or more currently available therapies (e.g., cancer therapies, such as chemotherapy, radiation therapy, surgery, hormonal therapy and/or biological therapy/immunotherapy, anti-VEGF antibody therapy, particularly a standard therapeutic regimen for the particular cancer) is not clinically adequate to treat the patients or the patients are no longer receiving any beneficial effect from the therapy such that these patients need additional effective therapy. As used herein, the phrase can also refer to a condition of the "non-responsive/refractory" patient, e.g., which describe patients who respond to therapy yet suffer from side effects, develop resistance, do not respond to the therapy, do not respond satisfactorily to the therapy, etc. In various embodiments, a cancer is relapse tumor growth or relapse cancer cell growth where the number of cancer cells has not been significantly reduced, or has increased, or tumor size has not been significantly reduced, or has increased, or fails any further reduction in size or in number of cancer cells. The determination of whether the cancer cells are relapse tumor growth or relapse cancer cell growth can be made either in vivo or in vitro by any method known in the art for assaying the effectiveness of treatment on cancer cells, using the art-accepted meanings of "relapse" or "refractory" or "non-responsive" in such a context. A tumor resistant to anti-VEGF treatment is an example of a relapse tumor growth.

The invention provides methods of blocking or reducing relapse tumor growth or relapse cancer cell growth in a subject by administering anti-EGFL7 antibody to block or reduce the relapse tumor growth or relapse cancer cell growth in subject. In certain embodiments, the antagonist can be administered subsequent to the other cancer therapeutic. In certain embodiments, the anti-EGFL7 antibody is administered simultaneously with cancer therapy. Alternatively, or additionally, the anti-EGFL7 antibody therapy alternates with another cancer therapy, which can be performed in any order. The invention also encompasses methods for administering one or more inhibitory antibodies to prevent the onset or recurrence of cancer in patients predisposed to having cancer. Generally, the subject was or is concurrently undergoing cancer therapy. In one embodiment, the cancer therapy is treatment with an anti-angiogenesis agent, e.g., a VEGF antagonist. The anti-angiogenesis agent includes those known in the art and those found under the Definitions herein. In one embodiment, the anti-angiogenesis agent is an anti-VEGF neutralizing antibody or fragment (e.g., humanized A4.6.1, AVASTIN® (Genentech, South San Francisco, Calif.), Y0317, M4, G6, B20, 2C3, etc.). See, e.g., U.S. Pat. Nos. 6,582,959, 6,884,879, 6,703,020; WO98/45332; WO 96/30046; WO94/10202; EP 0666868B1; US Patent Applications 20030206899, 20030190317, 20030203409, and 20050112126; Popkov et al., Journal of Immunological Methods 288:149-164 (2004); and, WO2005012359. Additional agents can be administered in combination with VEGF antagonist and an anti-EGFL7 antibody for blocking or reducing relapse tumor growth or relapse cancer cell growth.

The antibodies of the invention (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibodies are suitably administered by pulse infusion, particularly with declining doses of the antibody. Dosing can be by any suitable route, e.g. by injections, such as intravenous or subcutaneous injections, depending in part on whether the administration is brief or chronic.

The location of the binding target of an antibody of the invention may be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described, e.g., in Marasco, *Gene Therapy* 4: 11-15 (1997); Kontermann, *Methods* 34: 163-170 (2004); U.S. Pat. Nos. 6,004,940 and 6,329,173; U.S. Patent Application Publication No. 2003/0104402, and PCT Publication No. WO2003/077945. See also, for example, WO96/07321 published Mar. 14, 1996, concerning the use of gene therapy to generate intracellular antibodies.

Intracellular expression of an intrabody may be effected by introducing a nucleic acid encoding the desired antibody or antigen-binding portion thereof (lacking the wild-type leader sequence and secretory signals normally associated with the gene encoding that antibody or antigen-binding fragment) into a target cell. One or more nucleic acids encoding all or a portion of an antibody of the invention can be delivered to a target cell, such that one or more intrabodies are expressed which are capable of binding to an intracellular target polypeptide and modulating the activity of the target polypeptide. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest.

In certain embodiments, nucleic acid (optionally contained in a vector) may be introduced into a patient's cells by in vivo and ex vivo methods. In one example of in vivo delivery, nucleic acid is injected directly into the patient, e.g., at the site where therapeutic intervention is required. In a further example of in vivo delivery, nucleic acid is introduced into a cell using transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of certain gene marking and gene therapy protocols, see Anderson et al., *Science* 256:808-813 (1992), and WO 93/25673 and the references cited therein. In an example of ex vivo treatment, a patient's cells are removed, nucleic acid is introduced into those isolated cells, and the modified cells are administered to the patient either directly or, for example, encapsulated within porous membranes which are implanted into the patient (see, e.g., U.S. Pat. Nos. 4,892,538 and 5,283,187). A commonly used vector for ex vivo delivery of a nucleic acid is a retroviral vector.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the target protein may be advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993).

Entry of antibodies into target cells can be enhanced by other methods known in the art. For example, certain sequences, such as those derived from HIV Tat or the Antennapedia homeodomain protein are able to direct efficient uptake of heterologous proteins across cell membranes. See, e.g., Chen et al., *Proc. Natl. Acad. Sci. USA* (1999), 96:4325-4329.

When the binding target of an antibody is located in the brain, certain embodiments of the invention provide for the antibody to traverse the blood-brain barrier. Several art-known approaches exist for transporting molecules across the blood-brain barrier, including, but not limited to, physical methods, lipid-based methods, stem cell-based methods, and receptor and channel-based methods.

Physical methods of transporting an antibody across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., *Gene Therapy* 9: 398-406 (2002)), interstitial infusion/convection-enhanced delivery (see, e.g., Bobo et al., *Proc. Natl. Acad. Sci. USA* 91: 2076-2080 (1994)), and implanting a delivery device in the brain (see, e.g., Gill et al., *Nature Med.* 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., *Implication of the Blood-Brain Barrier and its Manipulation*, Vols 1 & 2, Plenum Press, N.Y. (1989)), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody (see, e.g., U.S. Patent Publication No. 2003/0083299).

Lipid-based methods of transporting an antibody across the blood-brain barrier include, but are not limited to, encapsulating the antibody in liposomes that are coupled to antibody binding fragments that bind to receptors on the vascular endothelium of the blood-brain barrier (see, e.g., U.S. Patent Application Publication No. 20020025313), and coating the antibody in low-density lipoprotein particles (see, e.g., U.S. Patent Application Publication No. 20040204354) or apolipoprotein E (see, e.g., U.S. Patent Application Publication No. 20040131692).

Stem-cell based methods of transporting an antibody across the blood-brain barrier entail genetically engineering neural progenitor cells (NPCs) to express the antibody of interest and then implanting the stem cells into the brain of the individual to be treated. See Behrstock et al. (2005) *Gene Ther.* 15 Dec. 2005 advanced online publication (reporting that NPCs genetically engineered to express the neurotrophic factor GDNF reduced symptoms of Parkinson disease when implanted into the brains of rodent and primate models).

Receptor and channel-based methods of transporting an antibody across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Diagnostic Methods and Methods of Detection

The anti-EGFL7 antibodies of the invention are useful in assays detecting EGFL7 expression (such as diagnostic or prognostic assays) in specific cells or tissues wherein the antibodies are labeled as described below and/or are immobilized on an insoluble matrix.

In another aspect, the invention provides methods for detection of EGFL7, the methods comprising detecting EGFL7-anti-EGFL7 antibody complex in the sample. The term "detection" as used herein includes qualitative and/or quantitative detection (measuring levels) with or without reference to a control.

In another aspect, the invention provides any of the anti-EGFL7 antibodies described herein, wherein the anti-EGFL7 antibody comprises a detectable label.

In another aspect, the invention provides a complex of any of the anti-EGFL7 antibodies described herein and EGFL7. In some embodiments, the complex is in vivo or in vitro. In some embodiments, the complex comprises a cancer cell. In some embodiments, the anti-EGFL7 antibody is detectably labeled.

Anti-EGFL7 antibodies (e.g., any of the EGFL7 antibodies described herein) can be used for the detection of EGFL7 in any one of a number of well known detection assay methods.

For example, a biological sample may be assayed for EGFL7 by obtaining the sample from a desired source, admixing the sample with anti-EGFL7 antibody to allow the antibody to form antibody/EGFL7 complex with any EGFL7 present in the mixture, and detecting any antibody/EGFL7 complex present in the mixture. The biological sample may be prepared for assay by methods known in the art which are suitable for the particular sample. The methods of admixing the sample with antibodies and the methods of detecting antibody/EGFL7 complex are chosen according to the type of assay used. Such assays include immunohistochemistry, competitive and sandwich assays, and steric inhibition assays. For sample preparation, a tissue or cell sample from a mammal (typically a human patient) may be used. Examples of samples include, but are not limited to, cancer cells such as colon, breast, prostate, ovary, lung, stomach, pancreas, lymphoma, and leukemia cancer cells. EGFL7 may also be measured in serum. The sample can be obtained by a variety of procedures known in the art including, but not limited to surgical excision, aspiration or biopsy. The tissue may be fresh or frozen. In one embodiment, the sample is fixed and embedded in paraffin or the like. The tissue sample may be fixed (i.e. preserved) by conventional methodology (See e.g., "Manual of Histological Staining Method of the Armed Forces Institute of Pathology," $3^{rd}$ edition (1960) Lee G. Luna, H T (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of ordinary skill in the art will appreciate that the choice of a fixative is determined by the purpose for which the sample is to be histologically stained or otherwise analyzed. One of ordinary skill in the art will also appreciate that the length of fixation depends upon the size of the tissue sample and the fixative used. By way of example, neutral buffered formalin, Bouin's or paraformaldehyde, may be used to fix a sample. Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine. If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De7 (CMS, Houston, Tex.) may be used.

Analytical methods for EGFL7 all use one or more of the following reagents: labeled EGFL7 analogue, immobilized EGFL7 analogue, labeled anti-EGFL7 antibody, immobilized anti-EGFL7 antibody and steric conjugates. The labeled reagents also are known as "tracers."

The label used is any detectable functionality that does not interfere with the binding of EGFL7 and anti-EGFL7 antibody. Numerous labels are known for use in immunoassay, examples including moieties that may be detected directly, such as fluorochrome, chemiluminescent, and radioactive labels, as well as moieties, such as enzymes, that must be reacted or derivatized to be detected.

The label used is any detectable functionality that does not interfere with the binding of EGFL7 and anti-EGFL7 antibody. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^3H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, (3-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., *Nature*, 144: 945 (1962); David et al., *Biochemistry*, 13: 1014-1021 (1974); Pain et al., *J. Immunol. Methods*, 40: 219-230 (1981); and Nygren, *J. Histochem. and Cytochem.*, 30: 407-412 (1982). Preferred labels herein are enzymes such as horseradish peroxidase and alkaline phosphatase. The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y., 1981), pp. 147-166.

Immobilization of reagents is required for certain assay methods. Immobilization entails separating the anti-EGFL7 antibody from any EGFL7 that remains free in solution. This conventionally is accomplished by either insolubilizing the anti-EGFL7 antibody or EGFL7 analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the anti-EGFL7 antibody or EGFL7 analogue afterward, e.g., by immunoprecipitation.

The expression of proteins in a sample may be examined using immunohistochemistry and staining protocols. Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods. For sample preparation, a tissue or cell sample from a mammal (typically a human patient) may be used. The sample can be obtained by a variety of procedures known in the art including, but not limited to surgical excision, aspiration or biopsy. The tissue may be fresh or frozen. In one embodiment, the sample is fixed and embedded in paraffin or the like. The tissue sample may be fixed (i.e. preserved) by conventional methodology. One of ordinary skill in the art will appreciate that the choice of a fixative is determined by the purpose for which the sample is to be histologically stained or otherwise analyzed. One of ordinary skill in the art will also appreciate that the length of fixation depends upon the size of the tissue sample and the fixative used.

IHC may be performed in combination with additional techniques such as morphological staining and/or fluorescence in-situ hybridization. Two general methods of IHC are available; direct and indirect assays. According to the first assay, binding of antibody to the target antigen (e.g., EGFL7) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available.

Aside from the sample preparation procedures discussed above, further treatment of the tissue section prior to, during or following IHC may be desired, For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

Specimens thus prepared may be mounted and coverslipped. Slide evaluation is then determined, e.g. using a microscope, and staining intensity criteria, routinely used in the art, may be employed.

Other assay methods, known as competitive or sandwich assays, are well established and widely used in the commercial diagnostics industry.

Competitive assays rely on the ability of a tracer EGFL7 analogue to compete with the test sample EGFL7 for a limited number of anti-EGFL7 antibody antigen-binding sites. The anti-EGFL7 antibody generally is insolubilized before or after the competition and then the tracer and EGFL7 bound to the anti-EGFL7 antibody are separated from the unbound tracer and EGFL7. This separation is accomplished by decanting (where the binding partner was preinsolubilized) or by centrifuging (where the binding partner was precipitated after the competitive reaction). The amount of test sample EGFL7 is inversely proportional to the amount of bound tracer as measured by the amount of marker substance. Dose-response curves with known amounts of EGFL7 are prepared and compared with the test results to quantitatively determine the amount of EGFL7 present in the test sample. These assays are called ELISA systems when enzymes are used as the detectable markers.

Another species of competitive assay, called a "homogeneous" assay, does not require a phase separation. Here, a conjugate of an enzyme with the EGFL7 is prepared and used such that when anti-EGFL7 antibody binds to the EGFL7 the presence of the anti-EGFL7 antibody modifies the enzyme activity. In this case, the EGFL7 or its immunologically active fragments are conjugated with a bifunctional organic bridge to an enzyme such as peroxidase. Conjugates are selected for use with anti-EGFL7 antibody so that binding of the anti-EGFL7 antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small EGFL7 fragment so that antibody to hapten is substantially unable to bind the conjugate at the same time as anti-EGFL7 antibody. Under this assay procedure the EGFL7 present in the test sample will bind anti-EGFL7 antibody, thereby allowing anti-hapten to bind the conjugate, resulting in a change in the character of the conjugate hapten, e.g., a change in fluorescence when the hapten is a fluorophore.

Sandwich assays particularly are useful for the determination of EGFL7 or anti-EGFL7 antibodies. In sequential sandwich assays an immobilized anti-EGFL7 antibody is used to adsorb test sample EGFL7, the test sample is removed as by washing, the bound EGFL7 is used to adsorb a second, labeled anti-EGFL7 antibody and bound material is then separated from residual tracer. The amount of bound tracer is directly proportional to test sample EGFL7. In "simultaneous" sandwich assays the test sample is not separated before adding the labeled anti-EGFL7. A sequential sandwich assay using an anti-EGFL7 monoclonal antibody as one antibody and a polyclonal anti-EGFL7 antibody as the other is useful in testing samples for EGFL7.

The foregoing are merely exemplary detection assays for EGFL7. Other methods now or hereafter developed that use anti-EGFL7 antibody for the determination of EGFL7 are included within the scope hereof, including the bioassays described herein.

In one aspect, the invention provides methods to detect (e.g., presence or absence of or amount) a polynucleotide(s) (e.g., EGFL7 polynucleotides) in a biological sample from an individual, such as a human subject. A variety of methods for detecting polynucleotides can be employed and include, for example, RT-PCR, taqman, amplification methods, polynucleotide microarray, and the like.

Methods for the detection of polynucleotides (such as mRNA) are well known and include, for example, hybridization assays using complementary DNA probes (such as in situ hybridization using labeled EGFL7 riboprobes), Northern blot and related techniques, and various nucleic acid amplification assays (such as RT-PCR using complementary primers specific for EGFL7, and other amplification type detection methods, such as, for example, branched DNA, SPIA, Ribo-SPIA, SISBA, TMA and the like).

Biological samples from mammals can be conveniently assayed for, e.g., EGFL7 mRNAs using Northern, dot blot or PCR analysis. For example, RT-PCR assays such as quantitative PCR assays are well known in the art. In an illustrative embodiment of the invention, a method for detecting EGFL7 mRNA in a biological sample comprises producing cDNA from the sample by reverse transcription using at least one primer; amplifying the cDNA so produced using an EGFL7 polynucleotide as sense and antisense primers to amplify EGFL7 cDNAs therein; and detecting the presence or absence of the amplified EGFL7 cDNA. In addition, such methods can include one or more steps that allow one to determine the amount (levels) of EGFL7 mRNA in a biological sample (e.g. by simultaneously examining the levels a comparative control mRNA sequence of a housekeeping gene such as an actin family member). Optionally, the sequence of the amplified EGFL7 cDNA can be determined.

Probes and/or primers may be labeled with a detectable marker, such as, for example, a radioisotope, fluorescent compound, bioluminescent compound, a chemiluminescent compound, metal chelator or enzyme. Such probes and primers can be used to detect the presence of EGFL7 polynucleotides in a sample and as a means for detecting a cell expressing EGFL7 proteins. As will be understood by the skilled artisan, a great many different primers and probes may be prepared (e.g., based on the sequences provided in herein) and used effectively to amplify, clone and/or determine the presence or absence of and/or amount of EGFL7 mRNAs.

Optional methods of the invention include protocols comprising detection of polynucleotides, such as EGFL7 polynucleotide, in a tissue or cell sample using microarray technologies. For example, using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (see, e.g., WO 01/75166 published Oct. 11, 2001; (See, for example, U.S. Pat. No. 5,700,637, U.S. Pat. No. 5,445,934, and U.S. Pat. No. 5,807,522, Lockart, Nature Biotechnology, 14:1675-1680 (1996); Cheung, V. G. et al., Nature Genetics 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1. preparation of fluorescently labeled target from RNA isolated from the sample, 2. hybridization of the labeled target to the microarray, 3. washing, staining, and scanning of the array, 4. analysis of the scanned image and 5. generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ).

The Affymetrix GeneChip® system is a commercially available microarray system which comprises arrays fabricated by direct synthesis of oligonucleotides on a glass surface. Probe/Gene Arrays: Oligonucleotides, usually 25 mers, are directly synthesized onto a glass wafer by a combination of semiconductor-based photolithography and solid phase chemical synthesis technologies. Each array contains up to 400,000 different oligos and each oligo is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligo. The Microarray Suite software subtracts the hybridization intensities of the mismatch probes from those of the perfect match probes to determine the absolute or specific intensity value for each probe set. Probes are chosen based on current information from GenBank® and other nucleotide repositories. The sequences are believed to recognize unique regions of the 3' end of the gene.

A GeneChip® Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

In some embodiments, the treatment is for a cancer selected from the group consisting of colorectal cancer, lung cancer, ovarian cancer, pituitary cancer, pancreatic cancer, mammary fibroadenoma, prostate cancer, head and neck squamous cell carcinoma, soft tissue sarcoma, breast cancer, neuroblastomas, melanoma, breast carcinoma, gastric cancer, colorectal cancer (CRC), epithelial carcinomas, brain cancer, endometrial cancer, testis cancer, cholangiocarcinoma, gallbladder carcinoma, and hepatocellular carcinoma.

Biological samples are described herein, e.g., in the definition of Biological Sample. In some embodiment, the biological sample is serum or of a tumor.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition(s) effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises an antibody of the invention; and (b) a second container with a composition contained therein. The article of manufacture in this embodiment of the invention may further comprise a package insert indicating that the first and second antibody compositions can be used to treat a particular condition, e.g. cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

Commercially available reagents referred to in the Examples were used according to manufacturer's instructions unless otherwise indicated.

Example 1

Generation of Humanized mu4F11 Antibodies

This example demonstrates the humanization of the murine antibody 4F11 (mu4F11) directed against EGFL7. Residue numbers are according to Kabat (Kabat et al., Sequences of proteins of immunological interest, 5th Ed., Public Health Service, National Institutes of Health, Bethesda, Md. (1991)). Single letter amino acid abbreviations are used.

Materials and Methods

Full length human EGFL7 and a truncated form of human EGFL7 (residues 1-182) containing the EMI and 2 EGF domains (lacking the 2 coiled-coiled domains) were expressed in CHO cells and purified by conventional means (FIG. 1). Peptides containing the 4F11 epitope on EGFL7 called p2 (RPRYACCPGWKRT; SEQ ID NO: 5) and EMI2 (PARPRYACCPGWKRTSGLPGACGAAICQPP; SEQ ID NO: 4) were made synthetically.

A hybridoma expressing the murine antibody 4F11 was obtained by immunizing Egfl7 knockout mice with recombinant full length human EGFL7 protein expressed in *E. coli* and refolded. Antibodies were screened by ELISA using recombinant human or murine EGFL7 coated plates. A panel of function blocking antibodies were identified by their ability to block HUVEC adhesion to EGFL7 coated plates. Several antibodies were identified as cross-species function blocking antibodies, including one designated 4F11 (see co-owned International Patent Application WO 2007/106915, filed 16 Mar. 2007 and published 20 Sep. 2007).

Cloning of Murine 4F11 Variable Domains and Generation of a Chimeric 4F11 Antibody—

Total RNA was extracted from hybridoma cells producing 4F11 using standard methods. The variable light (VL) and variable heavy (VH) domains were amplified using RT-PCR with degenerate primers to the heavy and light chains. The forward primers were specific for the N-terminal amino acid sequence of the VL and VH regions. Respectively, the LC and HC reverse primers were designed to anneal to a region in the constant light (CL) and constant heavy domain 1 (CH1), which are highly conserved across species. Amplified VL and VH were cloned into mammalian expression vectors to generate a chimeric antibody ch4F11. The polynucleotide sequence of the inserts was determined using routine sequencing methods.

Direct Hypervariable Region Grafts onto Acceptor Human Consensus Framework—

The phagemid used for this work is a monovalent Fab-g3 display vector and consists of 2 open reading frames under control of a single phoA promoter. The first open reading frame consists of the stII signal sequence fused to the VL and CH1 domains of the acceptor light chain and the second consists of the stII signal sequence fused to the VH and CH1 domains of the acceptor heavy chain followed by the minor phage coat protein P3.

To make the CDR grafts, hypervariable regions from mu4F11 were grafted into the huKI and huIII consensus acceptor frameworks to generate the direct CDR-graft (4F11.v1) (FIGS. 2 and 3). In the VL domain the following regions were grafted to the human consensus acceptor: positions 24-34 (L1; SEQ ID NO: 31), 50-56 (L2; SEQ ID NO: 32) and 89-97 (L3; SEQ ID NO: 33). In the VH domain, positions 26-35 (H1; SEQ ID NO: 34), 49-65 (H2; SEQ ID NO: 35) and 95-102 (H3; SEQ ID NO: 36) were grafted. MacCallum et al. (MacCallum et al. *J. Mol. Biol.* 262: 732-745 (1996)) have analyzed antibody and antigen complex crystal structures and found position 49 of the heavy chain to be part of the contact region thus it seems reasonable to include this position in the definition of CDR-H2 when humanizing antibodies.

4F11.v1 was generated by Kunkel mutagenesis as both a Fab displayed on phage and as an IgG using separate oligonucleotides for each hypervariable region. Correct clones were identified by DNA sequencing.

Framework Toggle—

To identify framework positions important for binding, a framework toggle phage library was generated to offer either the murine or human amino acid at position 4 in VL, and positions 2, 48, 69, 71, 73, 75, 76, 78 and 91 in VH. These positions were diversified as outlined in FIG. 4, by Kunkel mutagenesis using 5 oligonucleotides to mutate 4F11.v1 that was used as a template.

Randomization of the Hypervariable Regions—

Sequence diversity was introduced at positions in the hypervariable regions using Kunkel mutagenesis. To generate a single position library (SPL), each position in each hypervariable region was individually randomized to all possible 20 amino acids using oligonucleotides encoding NNS. This resulted in 76 sub-libraries, each having a diversity of 20 that were combined into a pooled "single position library" (SPL) encompassing variants with a single mutation located within one of the hypervariable regions. The six templates used for mutagenesis had one stop codon (TAA) in the middle of CDR L1, L2, L3 H1, H2 or H3 to avoid reselecting the wild type sequence. When generating the SPL, the oligonucleotides used to introduce diversity also repaired the stop codon in the corresponding template.

For the limited libraries, 4 oligonucleotides were incorporated simultaneously which repaired the stop codons (TAA) and introduced NNS at positions 53 and 54 in CDR-L2, 29 in CDR-H1, 52 in CDR-H2 and 98 in CDR-H3.

Generation of Phage Libraries—

Oligonucleotides designed to introduce diversity into framework positions or hypervariable regions as outlined above, were phosphorylated separately in 20 µl reactions containing 660 ng of oligonucleotide, 50 mM Tris pH 7.5, 10 mM MgCl$_2$, 1 mM ATP, 20 mM DTT, and 5 U polynucleotide kinase for 1 h at 37° C.

To generate the framework toggle or limited libraries all phosphorylated oligonucleotides directed to introduce diversity were added simultaneously to the mutagenesis reaction. For the SPL, 76 individual Kunkel mutagenesis reactions were performed in a 96-well PCR plate. From the phosphorylated oligonucleotides reactions (above), 2 µl was added to 300 ng Kunkel template containing the corresponding stop codon in 50 mM Tris pH 7.5, 10 mM MgCl$_2$ in a final volume of 10 µl. The mixture was annealed at 90° C. for 2 min, 50° C. for 5 min and then cooled on ice. The annealed template was then filled in by adding 0.5 µl 10 mM ATP, 0.5 µl 10 mM dNTPs (10 mM each of dATP, dCTP, dGTP and dTTP), 1 µl 100 mM DTT, 1 µl 10× TM buffer (0.5 M Tris pH 7.5, 0.1 M MgCl$_2$), 80 U T4 ligase, and 4 U T7 polymerase in a total volume of 20 µl for 2 h at room temperature. These filled-in and ligated products were then each transformed into XL1-Blue cells, grown in 0.5 ml of 2YT containing 5 µg/ml of tetracycline and M13/KO7 helper phage (MOI 10) for 2 hr at 37° C. and then pooled and transferred to 500 ml 2YT containing 50 µg/ml carbenicillin and grown 16 h at 37° C.

Phage Selections—

Multiple forms of antigen were used for phage selections. Full length or truncated EGFL7 (5 µg/ml) were immobilized in 50 mM sodium bicarbonate pH 9.6 on MaxiSorp™ microtiter plates (Nunc) overnight at 4° C. EMI2 and p2 peptides were also biotinylated either through their free cysteine (using maleimide PEO$_2$-biotin; Pierce) or through the free amine on their amino terminus (using NHS-LC-biotin, Pierce). For biotinylation reactions, a 2-fold molar excess of biotin reagent was used in PBS. Biotinylated EMI2 and p2 peptides were captured on NeutrAvidin® (2 µg/ml) that had been immobilized in 50 mM sodium bicarbonate pH 9.6 on MaxiSorp™ microtiter plates (Nunc) overnight at 4° C. All plates were blocked for at least 1 h using Blocker™ Casein (Pierce).

Phage were harvested from the culture supernatant and suspended in PBS containing 5% powdered milk and 0.05% Tween™ 20 (PBSBT). Following addition of the phage library and a 1 hr incubation, microtiter wells were washed extensively with PBS containing 0.05% Tween™ 20 (PBST) and bound phage were eluted by incubating the wells with 20 mM HCl, 500 mM KCl for 30 min. Eluted phage were neutralized with 1 M Tris, pH 8 and amplified using XL1-Blue cells and M13/KO7 helper phage and grown overnight at 37° C. in 2YT, 50 µg/ml carbenicillin. The titers of phage eluted from a target containing well were compared to titers of phage recovered from a non-target containing well to assess enrichment.

Selection stringency was increased by both capturing phage that bound to decreasing concentrations of biotinylated p2 peptide in solution followed by capture on NeutrAvidin® for 10 min (on rate selection) and by increasing the washing time and temperature to allow weak binding phage to be washed away (off rate selection).

IgG Production—

For screening purposes, IgG variants were initially produced in 293 cells. Vectors coding for VL and VH (25 µg) were transfected into 293 cells using the FuGENE® system. 500 µl of FuGENE® was mixed with 4.5 ml of DMEM media containing no FBS and incubated at room temperature for 5 min. Each chain (25 µg) was added to this mixture and incubated at room temperature for 20 min and then transferred to five T-150 flasks for transfection overnight at 37° C. in 5% CO$_2$. The following day the media containing the transfection mixture was removed and replaced with 23 ml PS04 media with 0.1 ml/L trace elements (A0934) and 10 mg/L insulin (A0940). Cells were incubated for an additional 5 days after which the media was harvested at 1000 rpm for 5 min and sterile filtered using a 0.22 µm low protein-binding filter. Samples could be stored at 4° C. after addition of 2.5 ml 0.1% PMSF for every 125 ml of media.

Affinity Determinations—

Affinity determinations were performed by surface plasmon resonance using a BIAcore™-2000. Truncated EGFL7 or p2 peptide was immobilized (approximately 50-200 RU) in 10 mM sodium acetate pH 4.8 on a CM5 sensor chip. Purified IgG variants were injected (using a 2-fold serial dilution of 0.5 to 1000 nM in PBST) at a flow rate of 30 µL/min. Each sample was analyzed with 3-minute association and 3.5-minute disassociation. After each injection the chip was regenerated using 10 mM glycine pH 1.7.

Binding response was corrected by subtracting a control flow cell from IgG variant flow cells. A 1:1 Languir model of simultaneous fitting of $k_{on}$ and $k_{off}$ was used for kinetics analysis.

Cell Adhesion Assay—

Mouse EGFL7 (mEGFL7-CB-His) or human EGFL7 (EGFL7-CB-His) were coated on microtiter plates at 5 µg/ml in sodium carbonate buffer O/N at 4° C. then blocked with 1% BSA in PBS. Anti-EGFL7 antibodies were added (0.01 µg/ml to 100 µg/ml), followed by the addition of 20,000 Human Umbilical Vein Endothelial Cells (HUVEC)/well in appropriate cell growth medium (EGM Lonza). Control cells were seeded in wells without antibody to calculate 100% of seeded cells. Each antibody concentration was tested in triplicate. The plates were spun down for 5 min at 140 g to synchronize contact of cells with substrate and then incubated in CO$_2$ incubator for 30 min and washed 3 times with PBS. Cells that adhered to the plates were counted using CyQUANT® buffer (Molecular Probes) and calculated as percent of the total cells plated. The percentages of cells that bound to the plate were plotted against the concentrations of each antibody.

Results and Discussion

Humanization of 4F11—

The human acceptor framework used for humanization of mu4F11 is based on the consensus human kappa I VL domain and the consensus human subgroup III VH domain. Each complimentarity determining region (CDR) for mu4F11 was identified and grafted into the human acceptor framework to generate a CDR graft (4F11.v1) that could be displayed as an Fab on phage (FIGS. 2 and 3).

Antigen Evaluation for Phage Selection—

Figure 6:
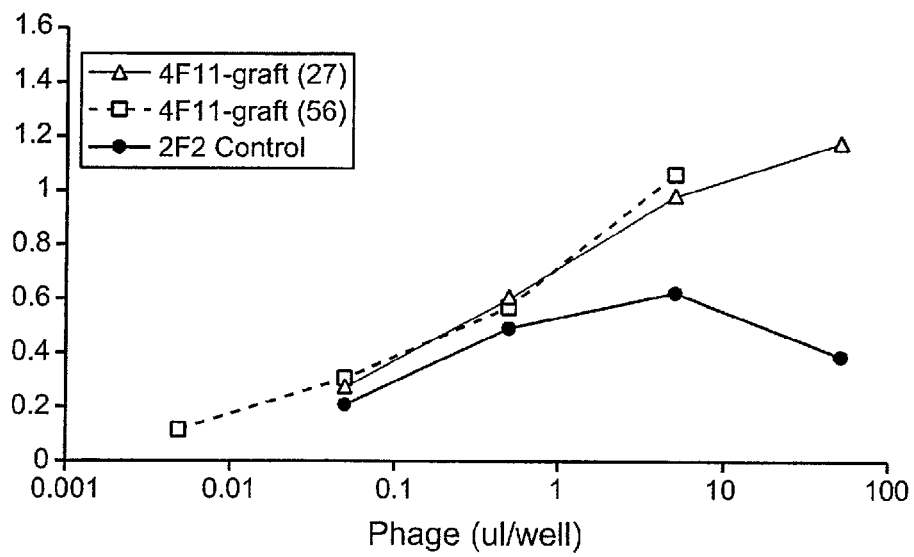
FIG. 6 depicts binding of phage displaying 4F11.v1 Fab to truncated EGFL7 immobilized on a microtiter plate. Both samples of 4F11.v1 phage show increased binding to immobilized EGFL7 as a function of increasing phage concentration. A control phage shows background binding similar to levels of 4F11.v1 phage at low phage concentrations suggesting some non-specific phage-EGFL7 interaction.
Figure 7:
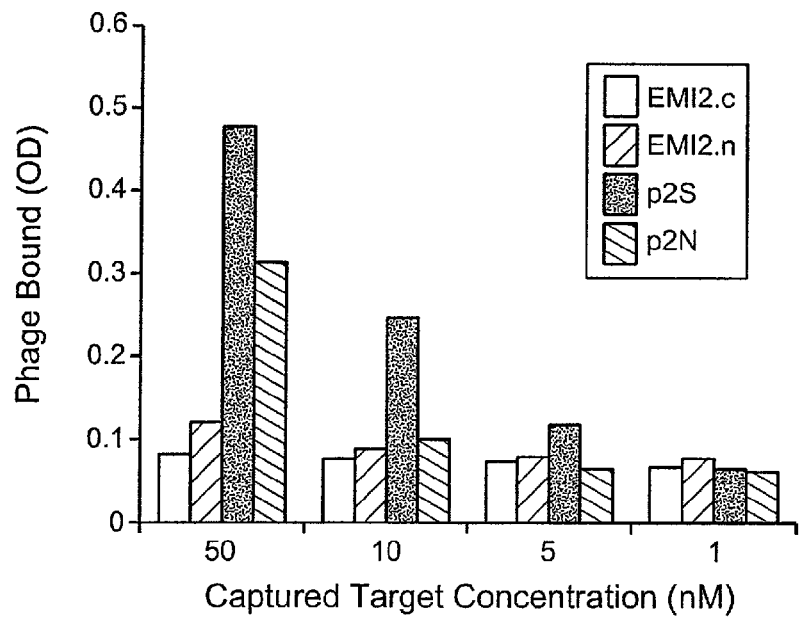
FIG. 7 depicts binding of phage displaying 4F11.v1 Fab to EMI2 domain or p2 peptide biotinylated either through a free amino or free thiol.

The 4F11 epitope on EGFL7 was mapped to the second EMI domain and more specifically to peptide p2 using a competition Western blot analysis (FIGS. 1 and 5). Phage displaying 4F11.v1 bound to immobilized full length and truncated EGFL7, but significant non-specific phage binding was also observed using a control phage (FIG. 6). For this reason, the p2 and EMI2 peptides that block 4F11 binding to truncated EGFL7 were used for phage selections. The peptides were biotinylated either through their free cysteine to generate p2S and EMI2c (using maleimide PEO$_2$-biotin; Pierce) or through the free amine on their amino terminus to generate p2N and EMI2.n (using NHS-LC-biotin, Pierce). To assess binding, biotinylated peptides were captured in microtiter wells coated with NeutrAvidin®. Phage displaying 4F11.v1 were used to assess binding to captured biotinylated EMI2 and p2 peptides. 4F11.v1 phage bound to best to p2S (FIG. 7). The amount of phage captured was greatest when a concentration of 50 nM biotinylated peptide was used for binding to the NeutrAvidin® coated well.

Screening Framework Positions—

Figure 8:
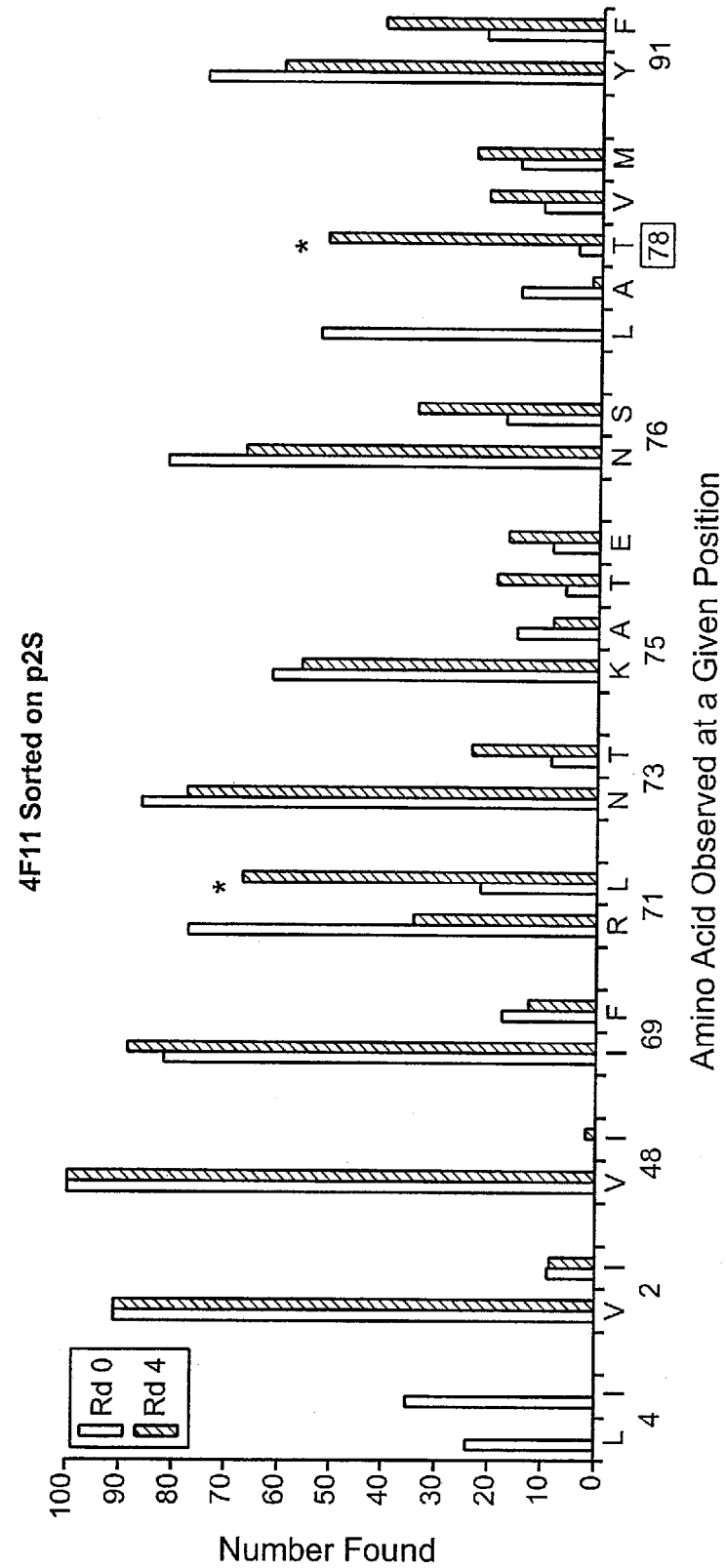
FIG. 8 depicts the abundance of residues found at each framework position during the Framework Toggle. Amino acids introduced at each framework position during the Framework Toggle are listed.

The framework toggle library was panned for 4 rounds of selection on immobilized biotinylated p2S peptide. DNA sequence analysis of 96 clones from the last round was used to evaluate the amino acid importance, based on abundance, at each toggled position (FIG. 8). Amino acid abundance prior to and after 4 rounds of selection suggested the replacement of L78 with Thr (L78T) or Val (L78V) might lead to improved binding.

Screening CDR Positions—

In order to identify further improvements, Single Position Libraries were generated using 3 frameworks: the initial CDR graft (4F11.v1), 4F11.v1 with L78T (4F11.v2), and 4F11.v1 with L78V (4F11.v3). For each SPL, each position in each CDR was individually randomized to all possible amino acids (a total of 76 libraries, each containing 20 members, pooled into one SPL for each framework). Six 4F11.v1 DNA templates (containing stop codons in the appropriate CDRs) were used to generate the three SPLs. The framework change at positions 78 in VH was introduced during SPL generation by using mutagenic oligonucleotides coding for the appropriate framework change (L78V or L78V). Thus, framework and individual CDR positions were mutated simultaneously. The SPLs were panned on soluble p2S peptide that was captured using immobilized NeutrAvidin® as outlined in Table 1:

TABLE 1

SPL Phage Selection Conditions

| | | Kon Selection | Koff Selection | |
|---|---|---|---|---|
| | Antigen | Binding Time | Excess Peptide | Capture |
| Round 1 | Immobilized p2S (50 nM on NeutrAvidin ®) | 1 hour | None | — |
| Round 2 | Immobilized p2S (50 nM on NeurAvidin) | 1 hour | None | — |
| Round 3 | 20 nM p2S in solution | 30 min | 3 hours | 10 min |
| Round 4 | 5 nM p2S in solution | 30 min | 4.5 hours; 37° C. | 10 min |
| Round 5 | 10 nM p2S in solution | 20 min | 70 hours; 37° C. | 10 min |

Selection stringency was gradually increased by decreasing the concentration of p2S peptide, reducing the time allowed for binding and increasing the wash time and temperature. The highest phage recovery during the last 3 rounds of selection was observed with SPLs based on 4F11.v2 and 4F11.v3.

Clones from the last round were picked for DNA sequence analysis. Individual sequence changes were identified in each CDR (FIG. 9). The most abundant SPL clones had changes in VL at position N53Y in CDR-L2. Changes that appeared frequently and in more than one SPL were incorporated into 4F11.v3. These variants (.v4 through .v12), the 4F11-graft (.v1) and changes to the VH framework (4F11.v2 and 4F11.v3), were expressed as IgG, purified and tested for binding to immobilized p2S by Biacore and using the Cell Adhesion Assay (Table 2). The weaker inhibition of cell adhesion observed for 4F11.v6 and 4F11.v10 compared to mu4F11 indicated further affinity improvements were desirable.

TABLE 2

Humanized 4F11 Variants Expressed as IgG

| Hu4F11 Variant | Light Chain | Heavy Chain | Binding to p2S (Biacore ™) | | | Cell Adhesion Assay Variant/ch4F11 (fold) |
|---|---|---|---|---|---|---|
| | | | ka (1/Ms) | kd (1/s) | KD (nM) | |
| chimera | | | 2.21E+05 | 7.51E−4 | 3.44 | 1.00 |
| .v1 | Graft | Graft | 3.42E+04 | 3.31E−03 | 96.8 | |
| .v2 | Graft | Graft + 78T | 5.35E+04 | 2.91E−03 | 54.4 | |
| .v3 | Graft | Graft + 78V | 8.45E+04 | 2.92E−03 | 34.6 | |
| .v4 | Graft + L1:D28R | Graft + 78V | 2.31E+05 | 3.14E−03 | 13.6 | |
| .v5 | Graft + L1:M33V | Graft + 78V | 7.11E+04 | 2.42E−03 | 34.0 | |
| .v6 | Graft + L2:N53Y | Graft + 78V | 1.23E+05 | 2.40E−03 | 19.5 | 4.01 |
| .v7 | Graft + L2:L54R | Graft + 78V | | | ND | |
| .v8 | Graft + L3:Y96F | Graft + 78V | | | ND | |
| .v9 | Graft | Graft + 78V + H1:F29R | 2.64E+05 | 2.30E−03 | 9.0 | |
| .v10 | Graft + L2:N53Y | Graft + 78V + H3:S98Y | 7.20E+04 | 1.97E−03 | 27.4 | 4.38 |
| .v11 | Graft | Graft + 78V + H3:S98Y | | | ND | |
| .v12 | Graft | Graft + 78V + H2:T52aI | 1.96E+05 | 2.18E−03 | 11.1 | |

Reassessment of Framework Positions—

Additional framework changes were incorporated in sets. Variants were expressed as IgG (variants 13 through 16) and tested by Biacore™ as outlined in Table 3:

TABLE 3

Humanized 4F11 Framework Variants Expressed as IgG

| Hu4F11 Variant | Light Chain | Heavy Chain | Binding to p2S (Biacore ™) | | |
|---|---|---|---|---|---|
| | | | ka (1/Ms) | kd (1/s) | KD (nM) |
| .v13 | Graft + M4L | Graft + R71L, L78A | 1.49E+05 | 1.86E−03 | 12.5 |
| .v14 | Graft + M4L | Graft + V2I, V48M, I69F, R71L, N73T, K75A, N76S, L78A, Y91F | 1.41E+05 | 9.84E−04 | 7.0 |
| .v15 | Graft | Graft + R71L, L78A | 9.05E+04 | 2.76E−03 | 30.5 |
| .v16 | Graft | Graft + V2I, V48M, I69F, R71L, N73T, K75A, N76S, L78A, Y91F | 9.81E+04 | 1.65E−03 | 16.8 |
| ch4F11 | | | 2.15E+05 | 7.92E−04 | 3.7 |

Of these, 4F11.v14 had the best affinity relative to mu4F11.

Limited Libraries—

Two limited libraries were generated based on 4F11.v13 as a template. Library 1 contained the same framework changes as 4F11.V13 (LC:M4L and HC: R71L, L78A) while library 2 contained 2 additional changes in the heavy chain: N76S and Y91F (FIGS. 10 and 11). CDR changes in L1 and L3 (D28S and D94E) were also incorporated into both libraries. Diversification was limited to positions where changes had been previously observed following selection of the SPLs (FIGS. 10 and 11). These positions (53 and 54 in the light chain and 29, 52, 98 in the heavy chain) were diversified to include all twenty amino acids and panned against immobilized p2S peptide that was captured using immobilized NeutrAvidin as outlined in Table 4:

TABLE 4

Limited Library Phage Selection Conditions

| | | Kon Selection | | Koff Selection | |
|---|---|---|---|---|---|
| | Antigen | Binding Time | Excess Peptide | | Capture |
| Round 1 | Immobilized b-p2S (50 nM on NeutrAvidin ®) | 1 hour | None | | — |
| Round 2 | Immobilized b-p2S (50 nM on NeurAvidin ®) | 1 hour | None | | — |
| Round 3 | 50 nM b-p2S in solution | 60 min | 30 min, r.t. | | 10 min |
| Round 4 | 10 nM b-p2S in solution | 30 min | 1 hr; 37° C. | | 5 min |
| Round 5 | 10 nM b-p2S in solution | 15 min | 2 hr; 37° C. | | 5 min |

Figure 13:
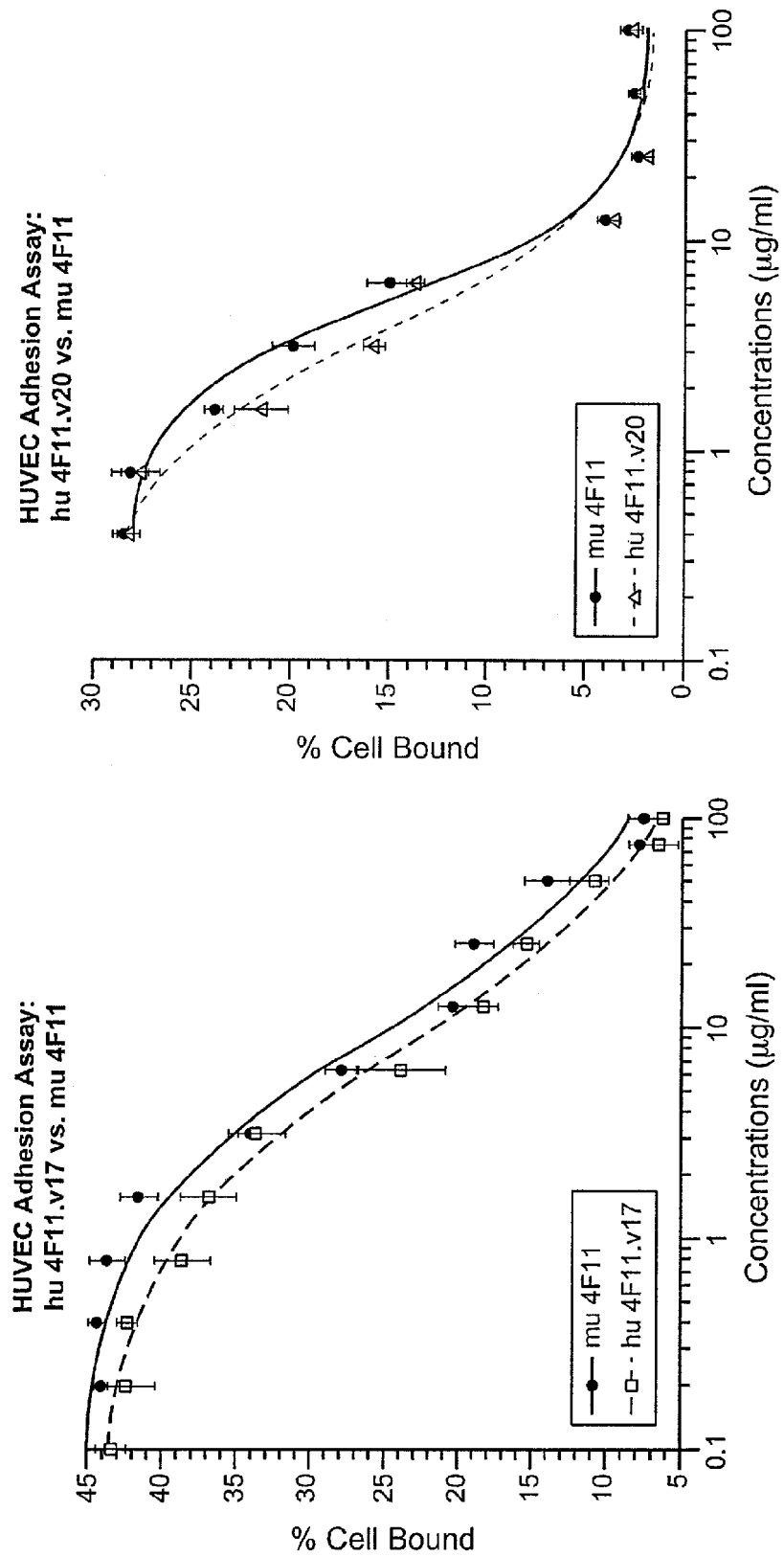
FIGS. 13 & 14 depict inhibition of HUVEC adhesion to immobilized human or mouse EGFL7 in vitro by humanized 4F11 variants. HUVECs (20,000 cells/well) were allowed to adhere to 96 well plates coated with 5 μg/ml human or murine EGFL7 in the presence of increasing concentrations of antibody. The number of cells that still adhered to the plates after washing were counted and calculated as percent of the total cells plated into each well.
Figure 14:
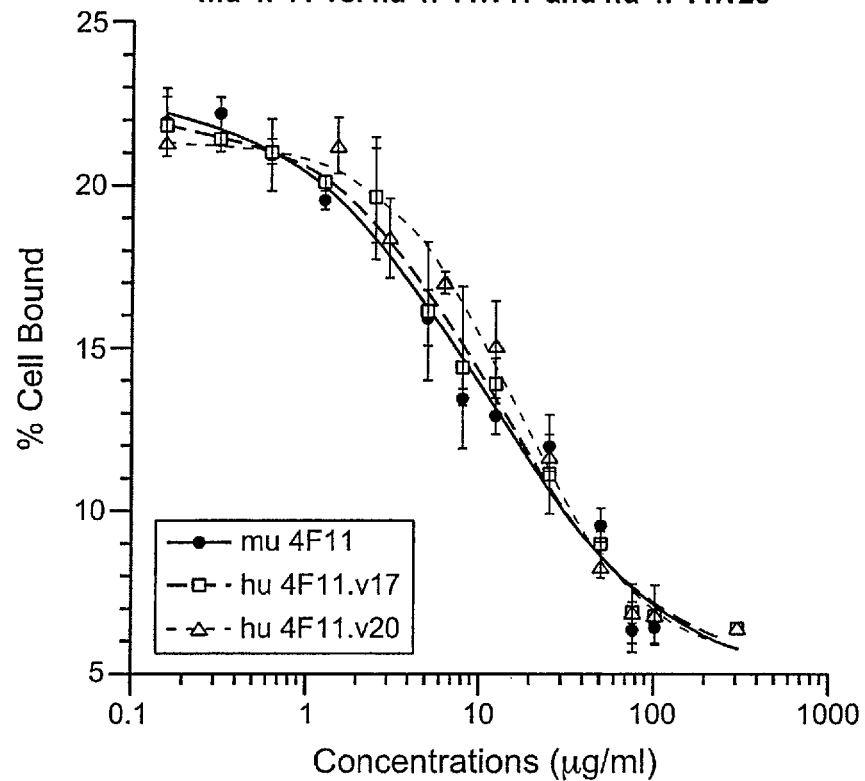

The preference for different amino acid residues at the randomized positions for each library is plotted in FIG. 12. In light chain, both libraries preferentially selected 53Y and 54R, while in the heavy chain, there was a preference for 29F and 52T. In CDR-H3 of the heavy chain, 3 amino acids were selected at position 98 (98Y, 98H, and 98R) in both libraries. To identify the best combination of these changes, variants 17 through 26 (Table 5) were constructed, expressed and characterized as IgG. Several variants had affinities as good or better than ch4F11. Variants were further characterized in the cell migration assay using human or mouse EGFL7 (Table 5 and FIGS. 13 and 14).

Example 2

Generation of Humanized mu18F7 Antibodies

This example demonstrates the humanization of the murine antibody 18F7 (mu18F7) directed against EGFL7. Residue numbers are according to Kabat (Kabat et al., Sequences of proteins of immunological interest, 5th Ed., Public Health Service, National Institutes of Health, Bethesda, Md. (1991)). Single letter amino acid abbreviations are used.

Materials and Methods

Full length human EGFL7 and a truncated form of human EGFL7 (residues 1-182) containing the EMI and 2 EGF domains (lacking the 2 coiled-coiled domains) were expressed in CHO cells and purified by conventional means (FIG. 1). Peptides containing the 18F7 epitope on EGFL7 called p5 (RACSTYRTIYRTA; SEQ ID NO: 7) and EMI1 (LTTCDGHRACSTYRTIYRTAYRRSPG; SEQ ID NO: 3) were made synthetically.

A hybridoma expressing the murine antibody 18F7 was obtained by immunizing Egfl7 knockout mice with recombinant full length human EGFL7 protein expressed in *E. coli* and refolded. Antibodies were screened by ELISA using recombinant human or murine EGFL7 coated plates. A panel of function blocking antibodies were identified by their ability to block HUVEC adhesion to EGFL7 coated plates. Several antibodies were identified as cross-species function blocking antibodies, including one designated 18F7 (see co-owned International Patent Application WO 2007/106915, filed 16 Mar. 2007 and published 20 Sep. 2007).

Cloning of Murine 18F7 Variable Domains and Generation of a Chimeric 18F7 Antibody—

Total RNA was extracted from hybridoma cells producing 18F7 using standard methods. The variable light (VL) and variable heavy (VH) domains were amplified using RT-PCR with degenerate primers to the heavy and light chains. The forward primers were specific for the N-terminal amino acid sequence of the VL and VH regions. Respectively, the LC and HC reverse primers were designed to anneal to a region in the

TABLE 5

Humanized 4F11 Variants Expressed as IgG

| Hu4F11 Variant | Light Chain Position | | Heavy Chain Position | | | VH Framework used | Binding to p2S (Biacore ™) Fold change in KD (variant/chimera) | Cell Adhesion Assay (human EGFL7) Variant/ch4F11 (fold) |
|---|---|---|---|---|---|---|---|---|
| | 53 | 54 | 29 | 52 | 98 | | | |
| ch4F11 | N | L | F | T | S | | 1 | 1.00 |
| .v17 | Y | R | F | T | Y | Library 1 | 0.93 | 0.86 |
| .v18 | Y | R | F | T | R | Library 1 | 1.81 | 1.86 |
| .v19 | Y | R | G | T | R | Library 1 | 1.43 | 12.87 |
| .v20 | Y | R | F | T | H | Library 1 | 1.79 | 0.70 |
| .v21 | Y | L | R | T | R | Library 1 | 1.31 | 3.12 |
| .v22 | Y | R | F | T | Y | Library 2 | 1 | 0.81 |
| .v23 | Y | R | F | T | R | Library 2 | 3.88 | nd |
| .v24 | Y | R | G | T | R | Library 2 | 0.48 | 2.52 |
| .v25 | Y | R | F | T | H | Library 2 | 0.56 | 1.82 |
| .v26 | Y | L | R | T | R | Library 2 | 0.66 | 1.38 |

Figure 16:
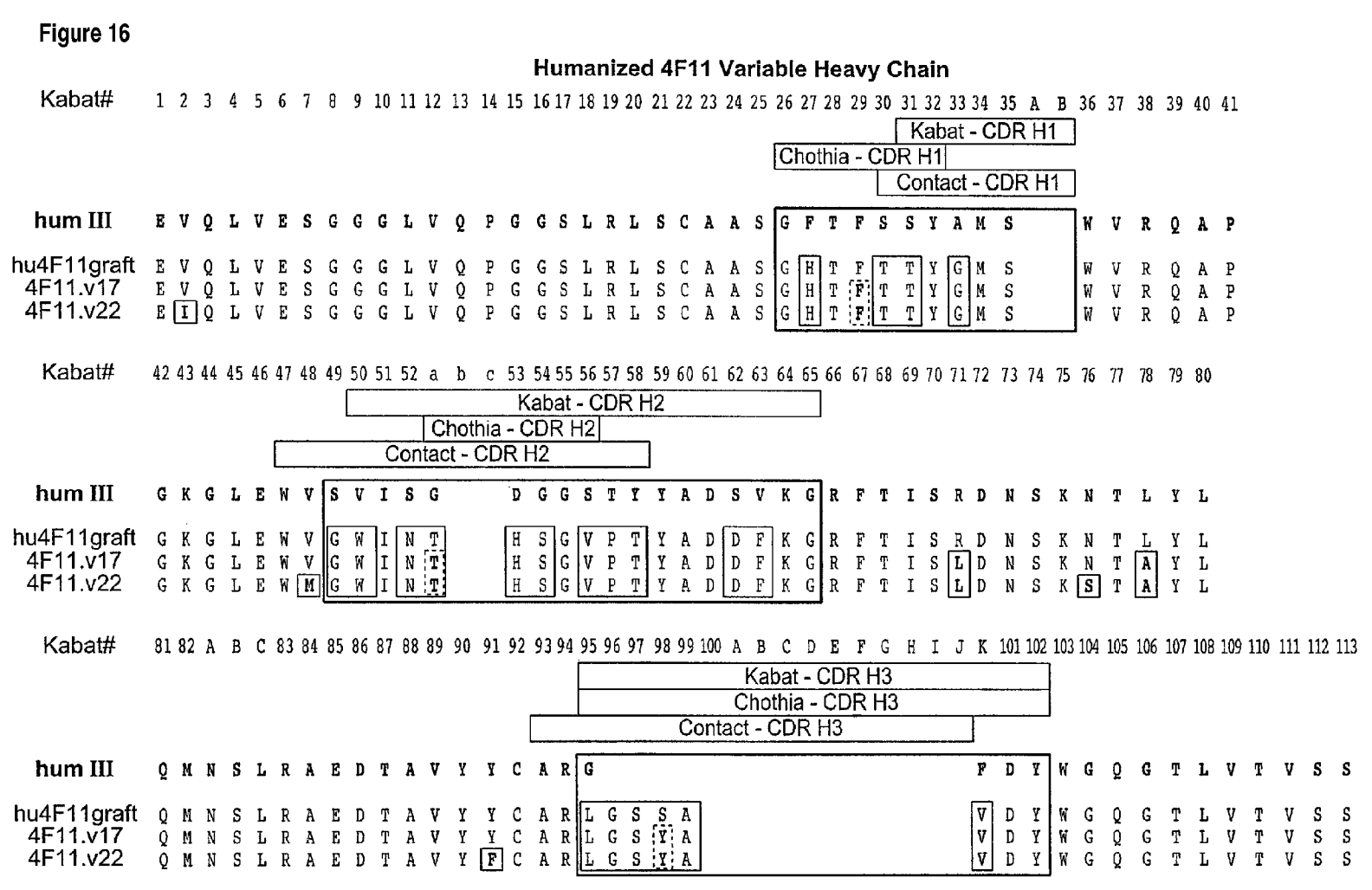

The VL and VH domains from hu4F11.v17 and 4F11.v22 compared to mu4F11 and 4F11.v1 are shown in FIGS. 15 and 16, respectively.

constant light (CL) and constant heavy domain 1 (CH1), which are highly conserved across species. Amplified VL and VH were cloned into mammalian expression vectors to generate a chimeric antibody ch18F7. The polynucleotide sequence of the inserts was determined using routine sequencing methods.

Direct Hypervariable Region Grafts onto the Acceptor Human Consensus Framework—

The phagemid used for this work is a monovalent Fab-g3 display vector and consists of 2 open reading frames under control of a single phoA promoter. The first open reading frame consists of the stII signal sequence fused to the VL and CH1 domains of the acceptor light chain and the second consists of the stII signal sequence fused to the VH and CH1 domains of the acceptor heavy chain followed by the minor phage coat protein P3.

To make the CDR grafts, hypervariable regions from mu18F7 were grafted into the huKI and huIII consensus acceptor frameworks to generate the direct CDR-graft (18F7-graft) (FIGS. 17 and 18). In the VL domain the following regions were grafted to the human consensus acceptor: positions 24-34 (L1; SEQ ID NO: 100), 50-56 (L2; SEQ ID NO: 101) and 89-97 (L3; SEQ ID NO: 102). In the VH domain, positions 26-35 (H1; SEQ ID NO: 103), 49-65 (H2; SEQ ID NO: 104) and 95-102 (H3; SEQ ID NO: 105) were grafted. MacCallum et al. (MacCallum et al. *J. Mol. Biol.* 262: 732-745 (1996)) have analyzed antibody and antigen complex crystal structures and found position 49 of the heavy chain to be part of the contact region thus it seems reasonable to include this position in the definition of CDR-H2 when humanizing antibodies.

The 18F7-graft was generated by Kunkel mutagenesis as both a Fab displayed on phage and as an IgG using separate oligonucleotides for each hypervariable region. Correct clones were identified by DNA sequencing.

Framework Toggle—

To identify framework positions important for binding, a framework toggle phage library was generated to offer either the murine or human amino acid at positions 87 in VL, and positions 48, 67, 69, 71, 73, 75, 76, 78 and 80 in VH. These positions were diversified as outlined in FIG. 19, by Kunkel mutagenesis using 3 oligonucleotides to mutate the 18F7-graft that was used as a template.

Randomization of the Hypervariable Regions—

Full sequence diversity was introduced separately at each position in the hypervariable regions of the 18F7-graft using Kunkel mutagenesis to generate single position libraries that were pooled together. Each position in each hypervariable region of 18F7-graft was fully randomized to all possible 20 amino acids using oligonucleotides encoding NNS at the respective positions. Multiple libraries were made each consisting of 20 members having a single position located within one of the hypervariable regions fully randomized. To cover each position in the hypervariable regions, 76 libraries of this type were generated and combined into a pooled "single position library" (SPL) encompassing single mutations located throughout each hypervariable position. A stop codon (TAA) was introduced in the middle of each CDR to avoid reselecting the wild type CDR grafted sequence. This was accomplished by Kunkel mutagenesis and resulted in 6 different templates for the 18F7-graft—each with a stop codon introduced into a different CDR. When generating the library, the oligonucleotides used to introduce diversity also repaired the stop codon in the corresponding template.

Generation of Phage Libraries—

Oligonucleotides designed to introduce diversity into framework positions or each hypervariable region as outlined above, were phosphorylated separately in 20 μl reactions containing 660 ng of oligonucleotide, 50 mM Tris pH 7.5, 10 mM $MgCl_2$, 1 mM ATP, 20 mM DTT, and 5 U polynucleotide kinase for 1 h at 37° C.

To generate the framework toggle library all 3 phosphorylated oligonucleotides directed to introduce diversity were added simultaneously to the mutagenesis reaction. For the SPL, 76 individual Kunkel mutagenesis reactions were performed in a 96-well PCR plate. From the phosphorylated oligonucleotides reactions (above), 2 μl was added to 300 ng Kunkel template containing the corresponding stop codon in 50 mM Tris pH 7.5, 10 mM $MgCl_2$ in a final volume of 10 μl. The mixture was annealed at 90° C. for 2 min, 50° C. for 5 min and then cooled on ice. The annealed template was then filled in by adding 0.5 μl 10 mM ATP, 0.5 μl 10 mM dNTPs (10 mM each of dATP, dCTP, dGTP and dTTP), 1 μl 100 mM DTT, 1 μl 10× TM buffer (0.5 M Tris pH 7.5, 0.1 M $MgCl_2$), 80 U T4 ligase, and 4 U T7 polymerase in a total volume of 20 μl for 2 h at room temperature. These filled-in and ligated products were then each transformed into XL1-Blue cells, grown in 0.5 ml of 2YT containing 5 μg/ml of tetracycline and M13/KO7 helper phage (MOI 10) for 2 hr at 37° C. and then pooled and transferred to 500 ml 2YT containing 50 μg/ml carbenicillin and grown 16 h at 37° C.

Phage Selections—

Multiple forms of antigen were used for phage selections. Full length or truncated EGFL7 (5 μg/ml) were immobilized in 50 mM sodium bicarbonate pH 9.6 on MaxiSorp™ microtiter plates (Nunc) overnight at 4° C. EMI1 and p5 peptides were also biotinylated either through their free cysteine (using maleimide $PEO_2$-biotin; Pierce) or through the free amine on their amino terminus (using NHS-LC-biotin, Pierce). For biotinylation reactions, a 2-fold molar excess of biotin reagent was used in PBS. Biotinylated EMI1 and p5 peptides were captured on NeutrAvidin® (2 μg/ml) that had been immobilized in 50 mM sodium bicarbonate pH 9.6 on MaxiSorp™ microtiter plates (Nunc) overnight at 4° C. All plates were blocked for at least 1 h using Blocker™ Casein (Pierce).

Phage were harvested from the culture supernatant and suspended in PBS containing 5% powdered milk and 0.05% Tween™ 20 (PBSBT). Following addition of the phage library and a 1 hr incubation, microtiter wells were washed extensively with PBS containing 0.05% Tween™ 20 (PBST) and bound phage were eluted by incubating the wells with 20 mM HCl, 500 mM KCl for 30 min. Eluted phage were neutralized with 1 M Tris, pH 8 and amplified using XL1-Blue cells and M13/KO7 helper phage and grown overnight at 37° C. in 2YT, 50 μg/ml carbenicillin. The titers of phage eluted from a target containing well were compared to titers of phage recovered from a non-target containing well to assess enrichment.

Selection stringency was increased by both capturing phage that bound to decreasing concentrations of biotinylated p5 peptide in solution followed by capture on NeutrAvidin® for 10 min (on rate selection) and by increasing the washing time and temperature to allow weak binding phage to be washed away (off rate selection).

IgG Production—

For screening purposes, IgG variants were initially produced in 293 cells. Vectors coding for VL and VH (25 μg) were transfected into 293 cells using the FuGENE® system. 500 μl of FuGENE® was mixed with 4.5 ml of DMEM media containing no FBS and incubated at room temperature for 5 min. Each chain (25 μg) was added to this mixture and incubated at room temperature for 20 min and then transferred to five T-150 flasks for transfection overnight at 37° C. in 5% $CO_2$. The following day the media containing the transfection mixture was removed and replaced with 23 ml PS04 media with 0.1 ml/L trace elements (A0934) and 10 mg/L insulin (A0940). Cells were incubated for an additional 5 days after which the media was harvested at 1000 rpm for 5 min and sterile filtered using a 0.22 μm low protein-binding filter. Samples could be stored at 4° C. after addition of 2.5 ml 0.1% PMSF for every 125 ml of media.

Affinity Determinations—

Affinity determinations were performed by surface plasmon resonance using a BIAcore™-2000. Truncated EGFL7 or p5 peptide was immobilized (approximately 50-200 RU) in 10 mM sodium acetate pH 4.8 on a CM5 sensor chip. Purified IgG variants were injected (using a 2-fold serial dilution of 0.5 to 1000 nM in PBST) at a flow rate of 30 μL/min. Each sample was analyzed with 3-minute association and 3.5-minute disassociation. After each injection the chip was regenerated using 10 mM glycine pH 1.7.

Binding response was corrected by subtracting a control flow cell from IgG variant flow cells. A 1:1 Languir model of simultaneous fitting of $k_{on}$ and $k_{off}$ was used for kinetics analysis.

Results and Discussion

Humanization of 18F7—

The human acceptor framework used for humanization of mu18F7 is based on the consensus human kappa I VL domain and the consensus human subgroup III VH domain. Each CDR for mu18F7 was identified and grafted into the human acceptor framework to generate a CDR graft that could be displayed as an Fab on phage (FIGS. 17 and 18).

Antigen Evaluation for Phage Selection—

Figure 20:
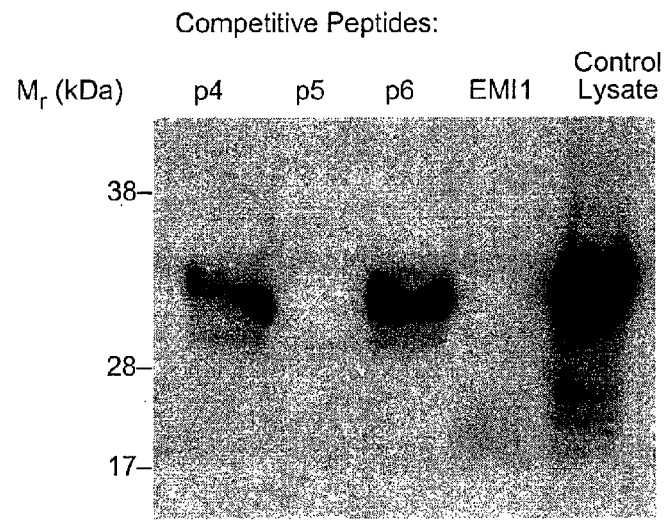
FIG. 20 depicts results demonstrating that mu18F7 binding to EGFL7 can be blocked by EMI1 (SEQ ID NO: 3) or Peptide P5 (SEQ ID NO: 7), but not by Peptides P4 or P6 (SEQ ID NOs: 6 and 8, respectively). Chicken embryonic fibroblasts were transfected with a plasmid containing the HA-tagged full-length human EGFL7 cDNA. Cell lysate prepared from transfected cells was immunoprecipitated with mu18F7 in the presence of 200-fold excess competitive peptides. Immunoprecipitates were analyzed by western blot using an anti-HA antibody.
Figure 21:
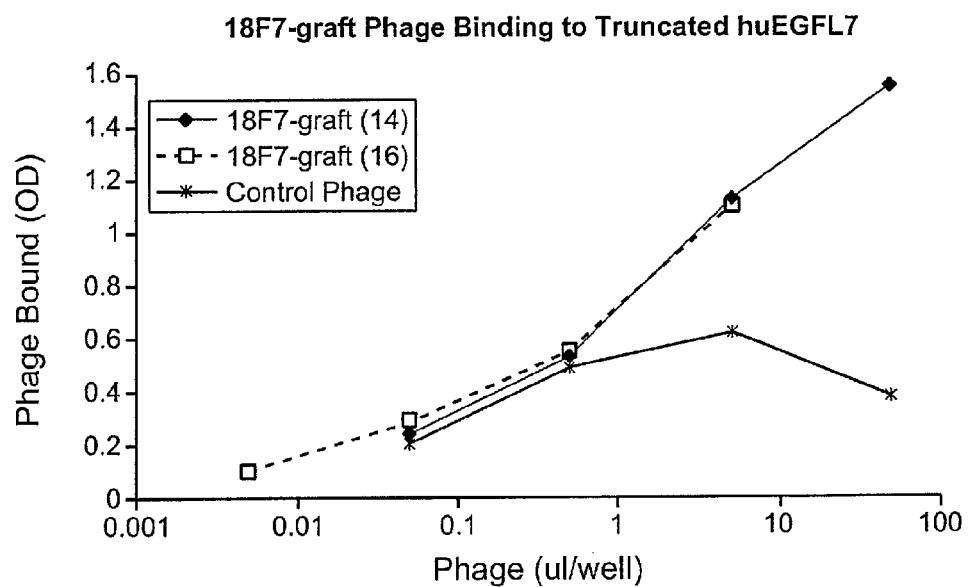
FIG. 21 depicts binding of phage displaying 18F7-graft Fab to truncated huEGFL7 immobilized on a microtiter plate. Both samples of 18F7-graft phage show increased binding to immobilized EGFL7 as a function of increasing phage concentration. A control phage shows background binding similar to levels of 18F7-graft phage at low phage concentrations suggesting some non-specific phage-EGFL7 interaction.
Figure 22:
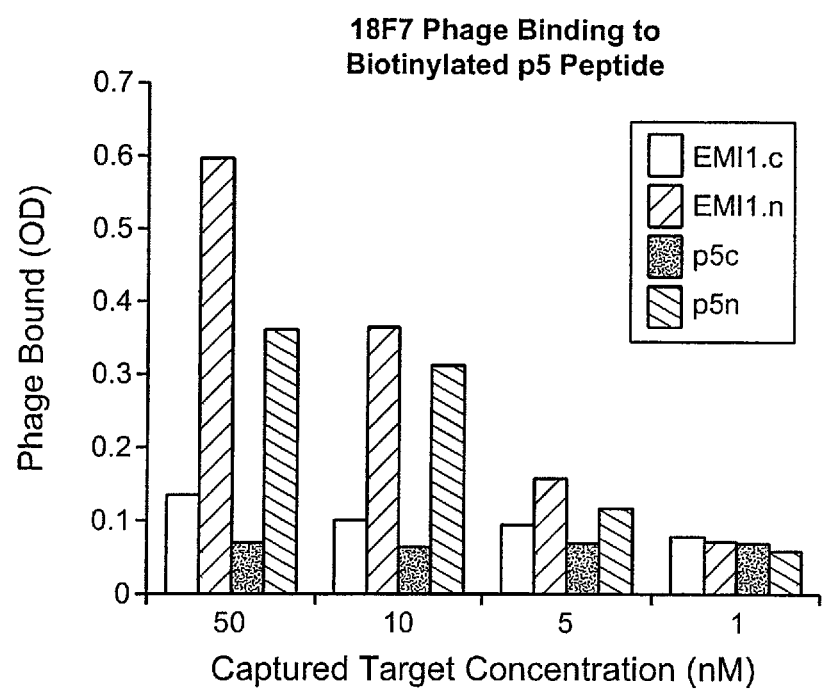
FIG. 22 depicts binding of phage displaying 18F7-graft Fab to EMI1 domain or p5 peptide biotinylated either through a free amino or free thiol.

The 18F7 epitope on EGFL7 was mapped to the first EMI domain and more specifically to peptide p5 using a competition Western blot analysis (FIGS. 1 and 20). Phage displaying the 18F7-graft bound to immobilized full length and truncated EGFL7, but significant non-specific phage binding was also observed using a control phage (FIG. 21). For this reason, the p5 and EMI1 peptides that block 18F7 binding to truncated EGFL7 were used for phage selections. The peptides were biotinylated either through their free cysteine to generate p5c and EMI1c (using maleimide PEO$_2$-biotin; Pierce) or through the free amine on their amino terminus to generate p5n and EMI1n (using NHS-LC-biotin, Pierce). To assess binding, biotinylated peptides were captured in microtiter wells coated with NeutrAvidin®. Following 2 rounds of selection on immobilized truncated EGFL7, the framework toggle library phage pool was used to assess binding to captured biotinylated EMI1 and p5 peptides. The phage pool bound to p5n and EMI1n, but not to p5c or EMI1c (FIG. 22). The amount of phage captured was greatest when a concentration of 50 nM biotinylated peptide was used for binding to the NeutrAvidin® coated well.

Figure 23:
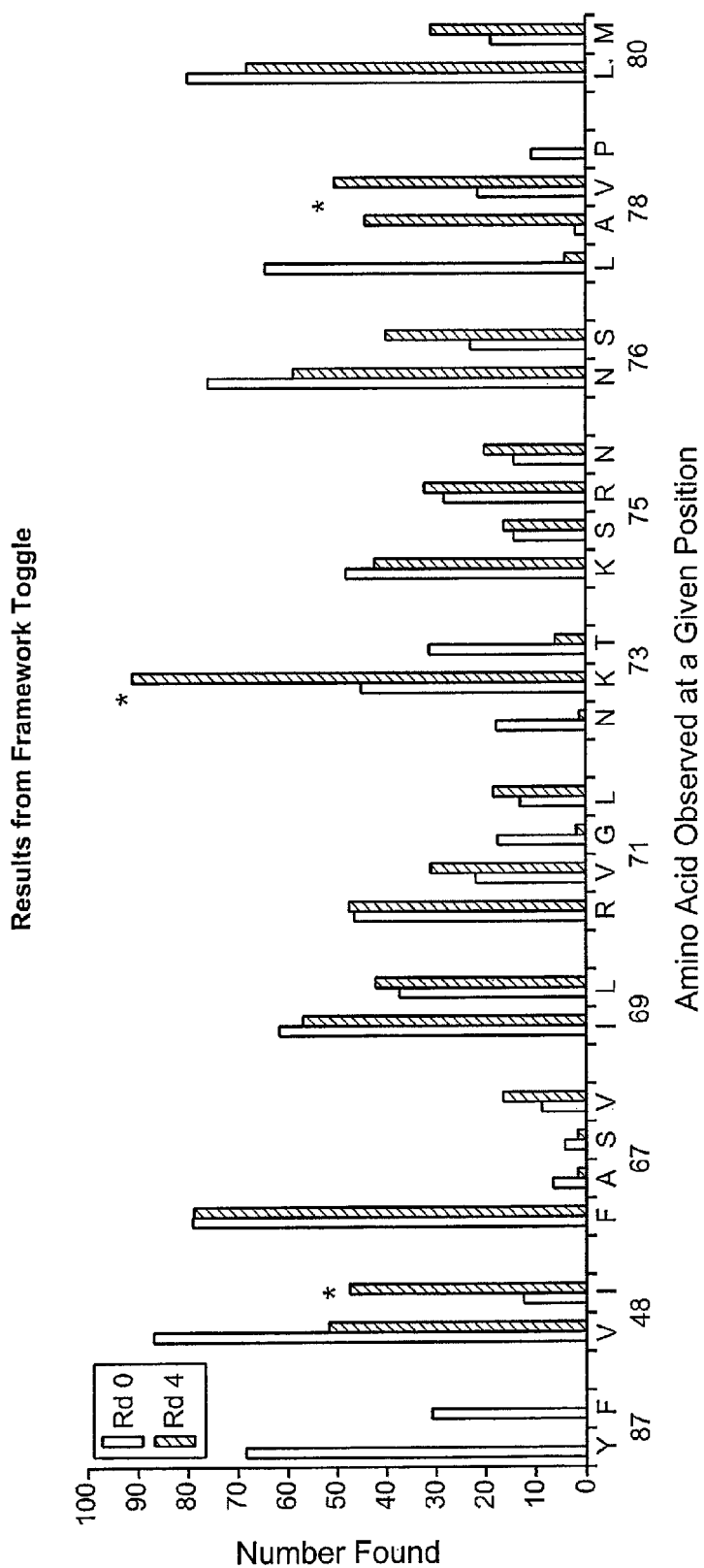
FIG. 23 depicts the abundance of residues found at each framework position during the Framework Toggle. Amino acids introduced at each framework position during the Framework Toggle are listed.

After selection for 2 rounds against immobilized truncated EGFL7, the framework toggle library was further panned for 2 rounds of selection on immobilized biotinylated p5n peptide. DNA sequence analysis of 96 clones from the last round was used to evaluate the amino acid importance, based on abundance, at each toggled position (FIG. 23). Amino acid abundance prior to and after 4 rounds of selection suggested the changes N73K and L78A lead to improved binding. Although less prominent, L78V and V48I also do so and L78V was further studied.

SPLs were explored in an effort to identify further improvements using 4 frameworks derived from the framework toggle library results. The 4 frameworks included the initial CDR graft (18F7-graft), 18F7-graft with N73K (18F7.v2), 18F7-graft with N73K and L78A (18F7.v3), and 18F7-graft with N73K and L78V (18F7.v4). For each framework, an SPL was generated where each position in each CDR was individually randomized to all possible amino acids (a total of 76 libraries, each containing 20 members, pooled into one SPL). Six 18F7-graft DNA templates (containing stop codons in the appropriate CDRs) were used to generate all four SPLs. Framework changes at positions 73 and 78 in VH were introduced during SPL generation by using mutagenic oligonucleotides coding for the appropriate framework changes. Thus, framework and individual CDR positions were mutated simultaneously. The four SPLs were panned for 2 rounds against immobilized truncated EGFL7 followed by 3 rounds of selection on soluble biotinylated p5n peptide that was captured using immobilized NeutrAvidin® as outlined in Table 6:

TABLE 6

SPL Phage Selection Conditions

| | Kon Selection | | Koff Selection | |
|---|---|---|---|---|
| | Antigen | Binding Time | Excess Peptide | Capture |
| Round 1 | Immobilized b-p5N (50 nM on NeutrAvidin ®) | 1 hour | None | — |
| Round 2 | Immobilized b-p5N (50 nM on NeurAvidin ®) | 1 hour | None | — |
| Round 3 | 20 nM b-p5N | 30 min | 3 hours | 10 min |
| Round 4 | 5 nM b-p5N | 30 min | 4.5 hours; 37° C. | 10 min |
| Round 5 | 10 nM b-p5N | 20 min | 70 hours; 37° C. | 10 min |

Selection stringency was gradually increased by decreasing the concentration of biotinylated p5n peptide, reducing the time allowed for binding and increasing the wash time and temperature. The highest phage recovery during the last 3 rounds of selection was observed with SPLs based on 18F7.v3 and 18F7.v4.

Clones from the last round were picked for DNA sequence analysis. Individual sequence changes were identified in each CDR (FIG. 24). The most abundant SP library clones had changes in VL at position S89. Changes that appeared frequently and in more than one SP library were incorporated into 18F7.v3. These variants (.v5 through .v10), the 18F7-graft (.v1) and changes to the VH framework (.v2, .v3 and .v4), were expressed as IgG for further analysis by Biacore™ (Tables 7 and 8).

TABLE 7

18F7-graft Variants Expressed as IgG

| hu18F7grafted variants | Light Chain | Heavy Chain |
|---|---|---|
| .v1 | Graft | Graft |
| .v2 | Graft | 73K |
| .v3 | Graft | 73K & 78A |
| .v4 | Graft | 73K & 78V |
| .v5 | L2:F55G | 73K & 78A |
| .v6 | L3:S89G | 73K & 78A |
| .v7 | L3:S89A | 73K & 78A |
| .v8 | L3:S89V | 73K & 78A |
| .v9 | Graft | 73K & 78A & H1:Y32K |
| .v10 | Graft | 73K & 78A & H3:D100P |

TABLE 8

Biacore™ Analysis of 18F7-graft Variants
Biacore Analysis of 18F7 Variants

| | | Over mEGFL7-CB at 37 C. | | | | | 37 C. over immobolized P5 | | |
|---|---|---|---|---|---|---|---|---|---|
| | | ka (1/Ms/1e5) | kd (1/s*1e4) | KD (nM) | | | ka (1/Ms/1e5) | kd (1/s*1e4) | KD (nM) |
| Chimeric 18F7 | n = 5 | 0.36 ± 0.16 | 0.96 ± 0.78 | 3.17 ± 3.48 | Chimeric 18F7 | n = 5 | 1.09 ± 0.30 | 5.44 ± 0.49 | 5.51 ± 2.46 |
| 18F7 V1 | | 0.97 | 2.74 | 2.82 | 18F7 V1 | | 3.17 | 20 | 6.3 |
| 18F7 V2 | | 1.10 | 1.98 | 1.81 | 18F7 V2 | | 4.58 | 11.9 | 2.59 |
| 18F7 V3 | | 0.55 | 0.905 | 1.64 | 18F7 V3 | | 2.03 | 8.58 | 4.22 |
| 18F7 V4 | | 0.50 | 2.08 | 4.15 | 18F7 V4 | | 1.82 | 13.2 | 7.27 |
| 18F7 V5 | | 0.73 | 1.17 | 1.61 | 18F7 V5 | | 3.30 | 8.92 | 2.7 |
| 18F7 V6 | | 0.50 | 0.204 | 0.408 | 18F7 V6 | n = 3 | 1.21 ± 0.14 | 3.89 ± 0.71 | 3.21 ± 0.49 |
| 18F7 V7 | | 0.70 | 0.958 | 1.38 | 18F7 V7 | | 2.51 | 7.18 | 2.87 |
| 18F7 V8 | | 0.98 | 1.99 | 2.04 | 18F7 V8 | | 4.72 | 10.2 | 2.16 |
| 18F7 V9 | | 0.59 | 0.932 | 1.58 | 18F7 V9 | | 2.28 | 7.63 | 3.35 |
| 18F7 V10 | | 1.60 | 1.95 | 1.22 | 18F7 V10 | | 8.25 | 8.11 | 0.982 |
| 18F7 V6A | n = 2 | 0.55 ± 0.01 | 4.04 ± 0.00 | 7.29 ± 0.17 | 18F7 V6A | n = 2 | 3.73 ± 0.91 | 13.70 ± 1.41 | 3.74 ± 0.52 |
| 18F7 V6B | n = 2 | 0.79 ± 0.25 | 1.74 ± 1.75 | 2.68 ± 3.06 | 18F7 V6B | n = 2 | 1.96 ± 0.25 | 6.38 ± 1.82 | 3.22 ± 0.52 |
| 18F7 V6C | n = 2 | 0.36 ± 0.06 | 0.81 ± 0.36 | 2.40 ± 1.42 | 18F7 V6C | n = 2 | 1.24 ± 0.28 | 5.02 ± 0.31 | 4.13 ± 0.66 |
| 18F7 V6D | | 1.03 | 7.91 | 7.65 | 18F7 V6D | n = 2 | 3.13 ± 1.89 | 23.25 ± 5.59 | 9.77 ± 7.69 |
| 18F7 V6E | | 0.48 | 4.74 | 9.9 | 18F7 V6E | | 3.03 | 15.4 | 5.1 |
| 18F7 V6I | | 0.23 | 4.88 | 21.3 | 18F7 V6I | | 1.90 | 31.6 | 16.7 |
| 18F7 V6J | | 0.21 | 0.164 | 6.8 | 18F7 V6J | | 1.08 | 6.07 | 5.6 |
| 18F7V6K | | 0.28 | 0.454 | 1.6 | 18F7 V6K | | 1.27 | 6.62 | 5.2 |

Figure 25:
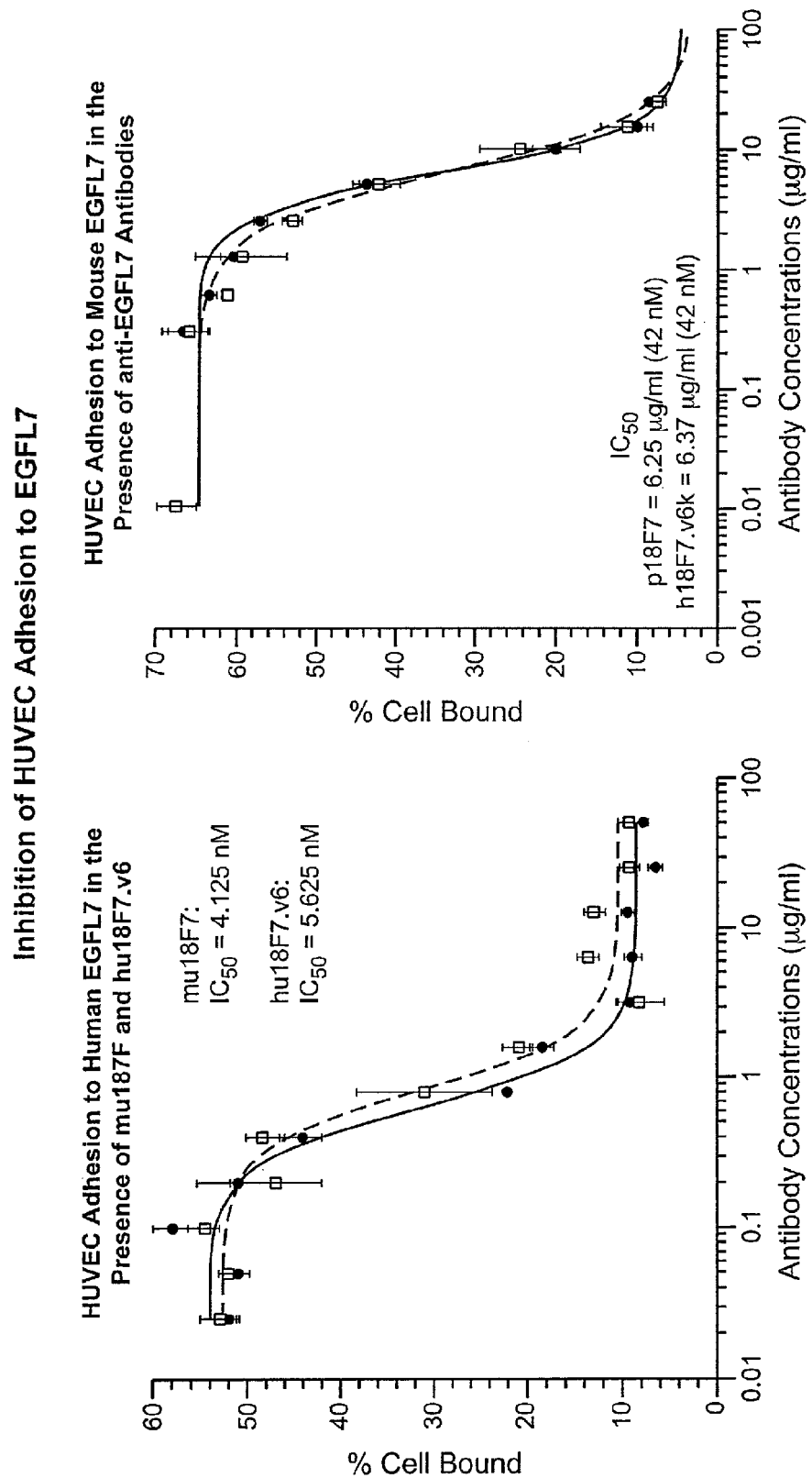
FIG. 25 depicts inhibition of HUVEC adhesion to immobilized human or mouse EGFL7 in vitro by humanized 18F7 variants. HUVECs (20,000 cells/well) were allowed to adhere to 96 well plates coated with 5 µg/ml human or murine EGFL7 in the presence of increasing concentrations of antibody. The number of cells that still adhered to the plates after washing were counted and calculated as percent of the total cells plated into each well.

Biacore™ analysis of these 10 variants indicated all bound quite well to immobilized mEGFL7 or the p5 peptide. 18F7.v6 had the slowest dissociation rate (kd) and was effective in the HUVEC adhesion assay (FIG. 25).

Polishing of 18F7.v6—

Potential iso-aspartic acid forming sites (Asn-Gly) in CDR-L1 (N28,G29) and CDR-H2 (N54, G55) in 18F7.v6 were eliminated by testing alternative amino acids at these positions (Table 9).

TABLE 9

Variants Tested to Eliminate Potential Iso-aspartic Acid Forming Sites

| hu18F7.v6 variants | Light Chain (N28 & G29) | Heavy Chain (N54 & G55) |
|---|---|---|
| .v6A | L1:SG (SEQ ID NO: 243) | .v6 (SEQ ID NO: 104) |
| .v6B | .v6 (SEQ ID NO: 100) | H2:SG (SEQ ID NO: 177) |
| .v6C | .v6 (SEQ ID NO: 100) | H2:NS (SEQ ID NO: 247) |
| .v6D | L1:SG (SEQ ID NO: 243) | H2:SG (SEQ ID NO: 177) |
| .v6E | L1:SG (SEQ ID NO: 243) | H2:NS (SEQ ID NO: 247) |
| .v6I | L1:QG (SEQ ID NO: 244) | H2:NS (SEQ ID NO: 247) |
| .v6J | L1:NS (SEQ ID NO: 245) | H2:NS (SEQ ID NO: 247) |
| .v6K | L1:NA (SEQ ID NO: 246) | H2:NS (SEQ ID NO: 247) |

Figure 26:
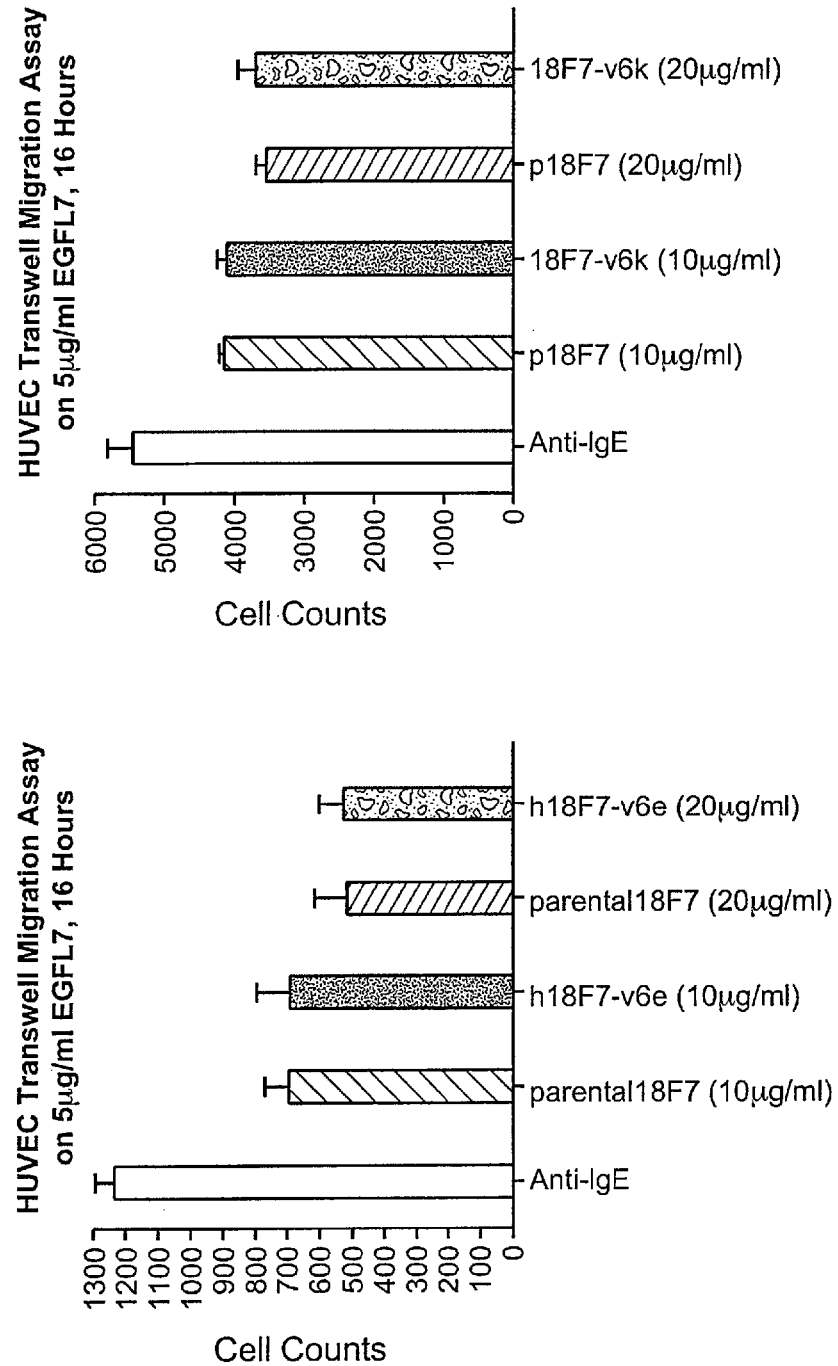
FIG. 26 depicts inhibition of HUVEC transwell migration. HUVECs (50,000 cells per well) were grown for 16 hours in the top chambers of transwell plates, and the membranes in the top chamber were coated with 5 µg/ml recombinant human EGFL7 protein. Various concentrations of control antibody (anti-IgE) or different variants of 18F7 were added to the culture medium in the top and bottom chambers, whereas 20 ng/ml of recombinant human VEGF-165 was added in the bottom wells to stimulate HUVEC migration. Cells migrated to the undersides of the top chambers were counted and plotted against the treatments (antibodies and concentrations).
Figure 28:
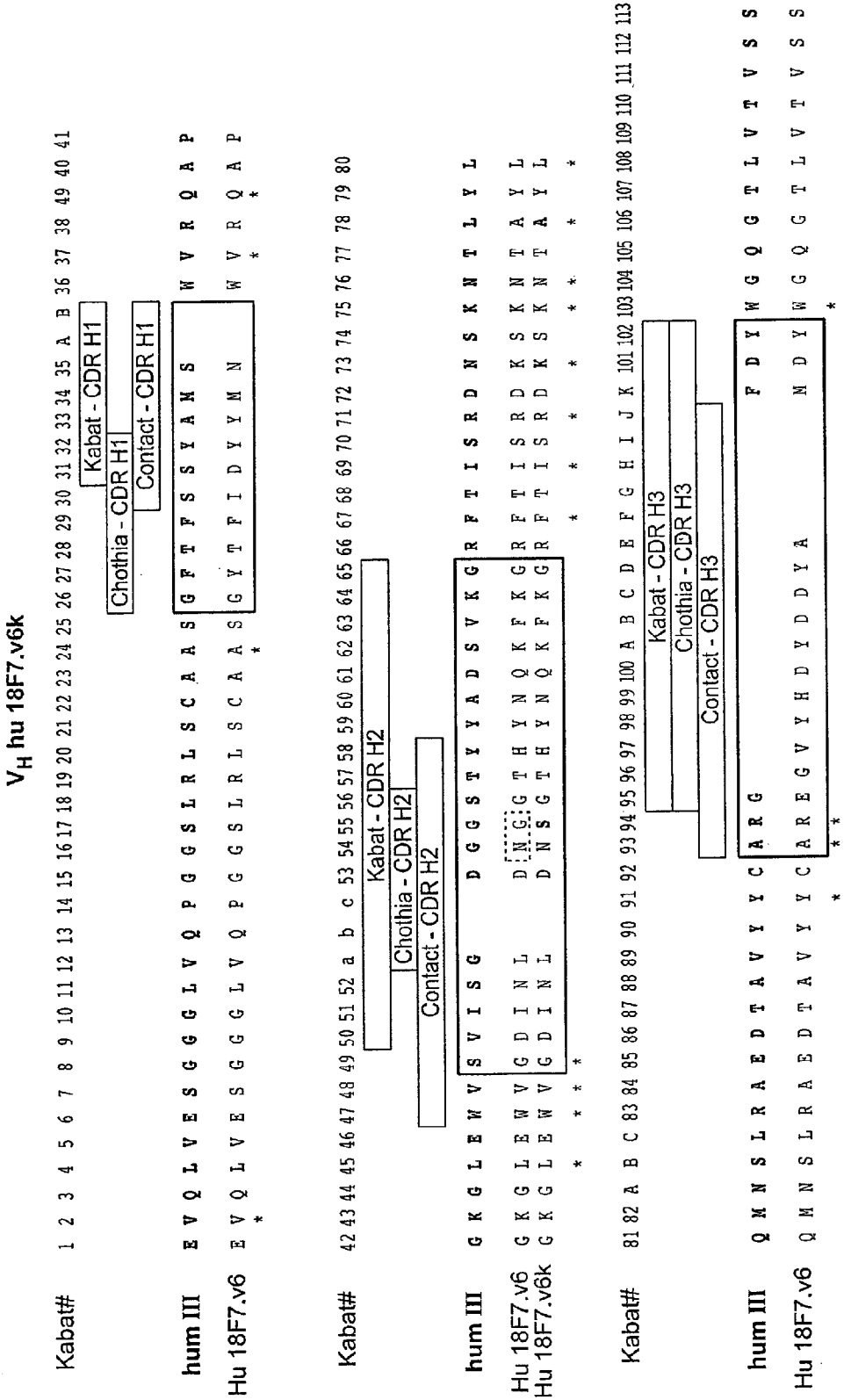
FIG. 28 depicts the amino acid sequence of the variable heavy domain of the human subgroup III consensus (SEQ ID NO: 11), 18F7.v6 (SEQ ID NO: 195), and 18F7.v6k (SEQ ID NO: 196). Positions are numbered according to Kabat and hypervariable regions (SEQ ID NOs: 103, 242, 105) are boxed. Where sequence for 18F7.v6k is not shown (in the first and third parts of the alignment), the corresponding sequence is identical to the sequence for 18F7.v6.

An SG sequence in H2 (.v6B and .v6D) expressed poorly, while this sequence in L1 (.v6A) increased the dissociation rate. In contrast, an NS sequence in H2 (.v6C) had little affect on the kinetics (Tables 8 and 9). Of the other changes sampled in L1 in conjunction with H2:NS (.v6C), the changes NS (.v6J) and NA (.v6K) had a minimal affect on the dissociation rate (Table 8 and 9, FIG. 25). These changes can be used to improve the stability of 18F7.v6 while still maintaining desired biological properties compared to murine 18F7 (FIGS. 25 and 26). The VL and VH domains from hu18F7.v6K are shown in FIGS. 27 and 28, respectively.

Example 3

Treatment of Tumor-Bearing Mice or Neonatal Mice with Humanized Anti-EGFL7 Antibody We investigated the ability of humanized anti-EGFL7 antibodies of the invention (alone and in combination with anti-VEGF therapy) to inhibit angiogenesis and/or tumor growth in a variety of models. We observed anti-EGFL7 antibodies enhance the efficacy of anti-VEGF therapy.

Figure 29:
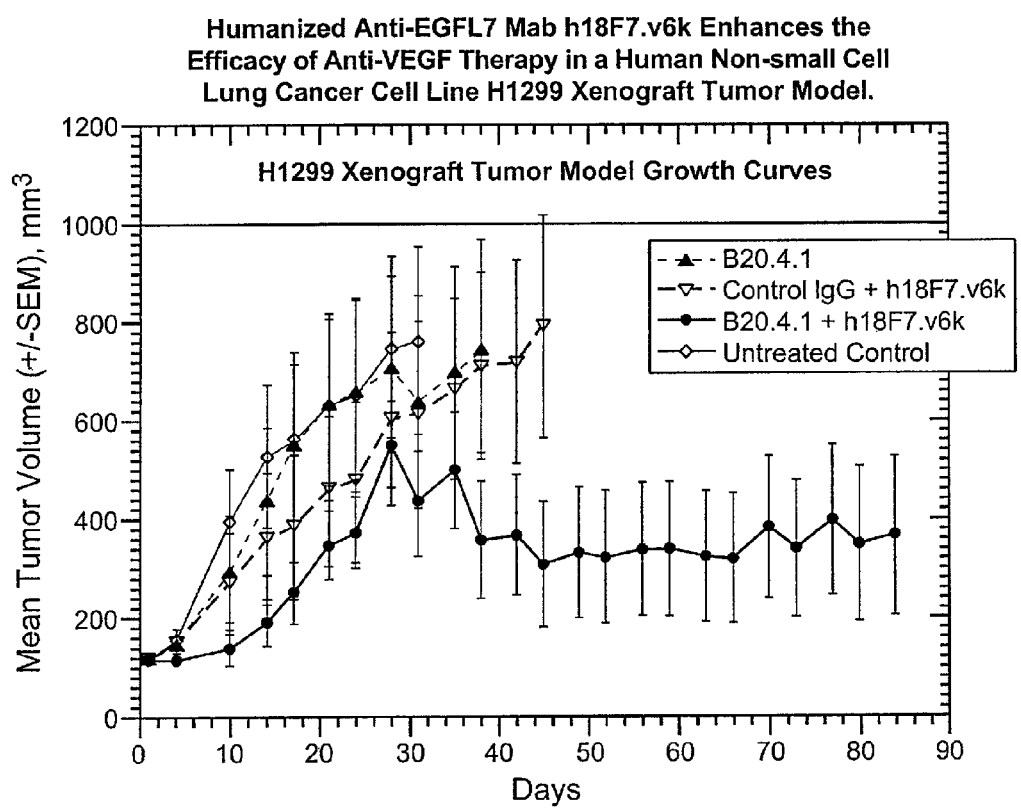
FIG. 29 depicts inhibition of H1299 xenograft tumor growth using hu18F7.v6k alone and in combination with an anti-VEGF antibody. HRLN female nu/nu mice were injected with $1 \times 10^7$ H1299 human non-small cell lung cancer tumor cells subcutaneously and allowed to develop tumors to 80-120 mm³ in sizes. Tumor bearing mice were then randomly separated into four groups (12 mice/group) so that the average tumor volume of each group was at 122 mm³. These mice were then treated as: group 1 received anti-VEGF MAb (B20.4.1) at 10 mg/kg once/week; group 2 received control IgG (anti-ragweed) at 10 mg/kg once/week and anti-EGFL7 MAb (h18F7.v6k) at 10 mg/kg twice/week; group 3 received B20.4.1 at 10 mg/kg once/week+h18F7.v6k at 10 mg/kg twice/week; group 4 was untreated. Tumors were measured twice/week with a caliper and tumor volumes were calculated as "w²×l/2" mm³ (w=tumor width in mm, l=tumor length in mm). Mice were euthanized when their tumors reached 1000 mm³ (this is defined as "mice reached end point"). Group average (mean) tumor volumes+/−standard errors (SEM) were plotted against time until ≥50% of mice reached end point.

HRLN female nu/nu mice were injected subcutaneously with $1 \times 10^7$ H1299 human non-small cell lung cancer tumor cells and allowed to develop tumors to 80-120 mm$^3$. Tumor-bearing mice were then randomly separated into four groups (12 mice each) so that the average tumor size in each group was 122 mm$^3$. These mice were then treated as follows: Group 1: intraperitoneal (ip) injection of anti-VEGF antibody (B20-4.1; WO2005/012359 and WO2005/044853) once per week at 10 mg/kg; Group 2: ip injection of a negative control antibody anti-ragweed IgG once per week at 10 mg/kg and anti-EGFL7 antibody (hu18F7.v6K) twice per week at 10 mg/kg; Group 3: ip injection of B20-4.1 once per week at 10 mg/kg and hu18F7.v6K twice per week at 10 mg/kg; Group 4: no treatment. Tumors were measured twice per week with a caliper and tumor volumes were calculated as $(w^2 \times l)/2$ (w=tumor width in mm, l=tumor length in mm). Mice were euthanized when their tumors reached 1000 mm$^3$ (defined as "mice reached end point"). Group average tumor volumes+/− SEM were plotted against time until≥50% of the mice reached end point. The data from this experiment showed that treatment with neither B20.4-1 nor hu18F7.v6K alone significantly reduced tumor growth over untreated control, although treatment with hu18F7.v6K exhibited a trend toward reduced growth (FIG. 29). In contrast, treatment with both B20.4-1 and hu18F7.v6K significantly inhibited tumor growth (FIG. 29).

Balb-c nude mice were injected subcutaneously in the right flank with $5 \times 10^6$ HM7 carcinoma cells in 0.1 ml Matrigel™. When mean tumor size reached 80-150 mm$^3$, animals were separated into 4 groups of 10 mice each so that the average tumor sizes in all the groups were roughly equal and treated as follows: Group 1: ip injection of anti-ragweed IgG twice per week at 5 mg/kg; Group 2: ip injection of B20-4.1.1 (PCT/US2008/013248) twice per week at 5 mg/kg; Group 3: ip injection of anti-EGFL7 antibody (hu18F7.v6k) twice per week at 10 mg/kg; Group 4: ip injection of B20-4.1.1 twice per week at 5 mg/kg and hu18F7.v6k twice per week at 10 mg/kg. Tumors were measured twice per week with a caliper and the width and length recorded. Mice were euthanized when tumors were greater than 1000 mm³ or when tumor growth or ulceration interfered with animal health. We observed that tumors in Groups 1 and 3 had similar growth rates, whereas tumors in Group 2 grew more slowly than those in Group 1 and tumors in Group 4 exhibited a negative growth.

Figure 30:
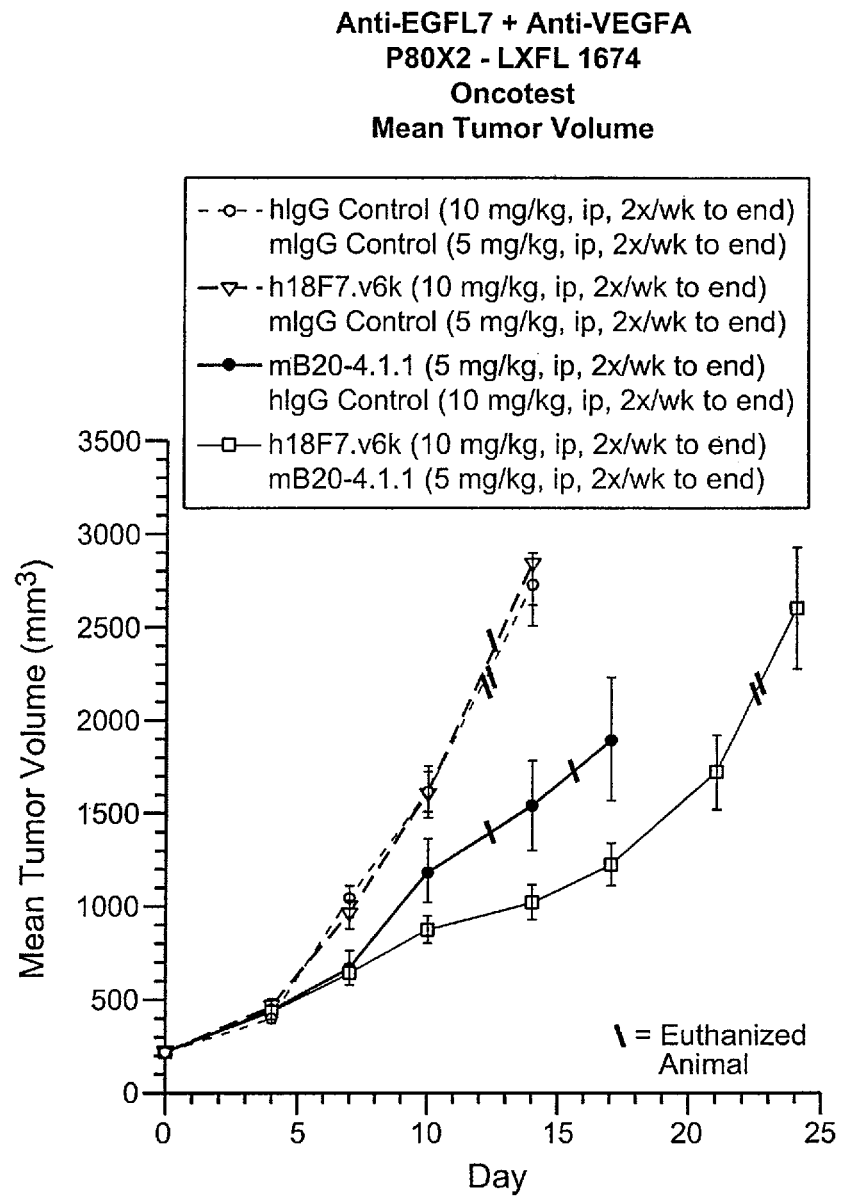
FIG. 30 depicts inhibition of LXFL 1674 xenograft tumor growth using hu18F7.v6k alone and in combination with an anti-VEGF antibody.

Balb-c nude mice were injected subcutaneously in the right flank with primary human large cell lung cancer tumor explants (LXFL 1674). The experiment comprised a reference group (Group 1) dosed with human IgG (hIgG) and murine IgG (mIgG) control antibodies, Group 2 that received hu18F7.v6k and mIgG, Group 3 that received B20-4.1.1 and hIgG, and Group 4 that received hu18F7.v6K and B20-4.1.1. All treatments were given twice weekly ip with hu18F7.v6k (or hIgG) given at 10 mg/kg/dose four hours prior to B20 to (or mIgG) administered at 5 mg/kg/dose. Mice were sacrificed individually when tumor volume exceeded 2000 mm³. Groups were evaluated for efficacy as long as more than 50% of Group 1 control mice were alive (day 14). Group size at the start of dosing was 10 mice bearing one tumor of 5-10 mm in diameter each per mouse. The advantage of the combination therapy over the B20-4.1.1 monotherapy was statistically significant (FIG. 30).

Figure 31:
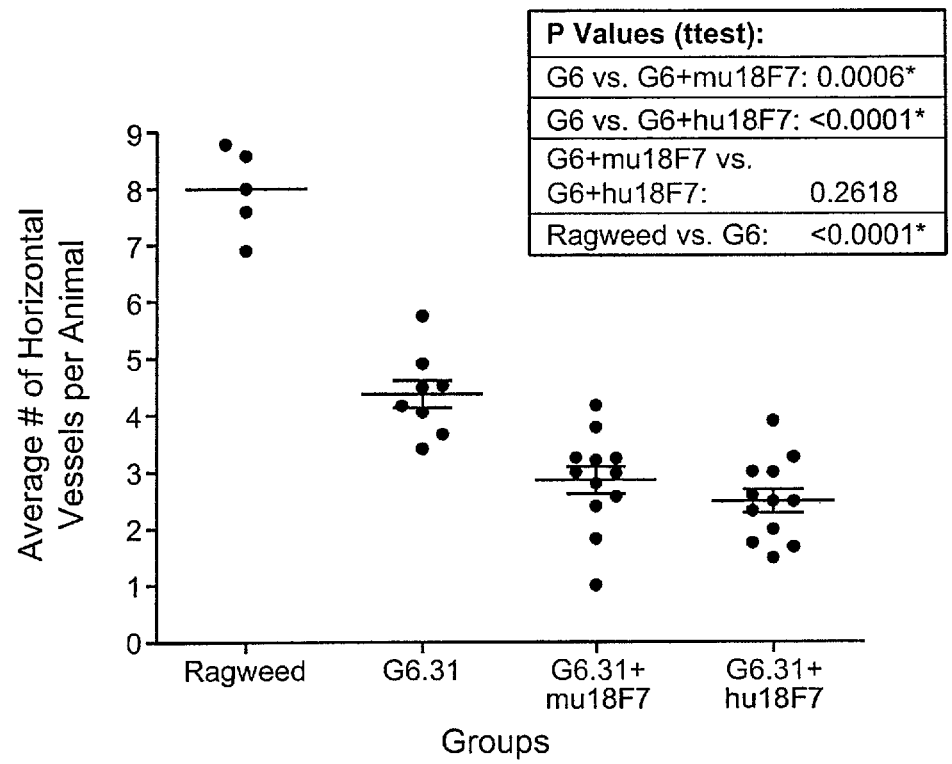
FIG. 31 depicts inhibition of neonatal trachea vascularization using hu18F7.v6k alone and in combination with an anti-VEGF antibody. Note: not all Ragweed control animals were quantified since data distribution was reasonably tight in this group.

We also tested the humanized anti-EGFL7 antibody hu18F7.v6k and its parental antibody murine 18F7 in a murine neonatal organ angiogenesis assay. Newborn mice were injected with antibodies at days 1 and 3 after birth and organs were harvested on day 5. The vasculatures in multiple organs were stained with a vascular endothelial cell marker CD31 and vascular densities were quantified. The groups were: Group 1 which received 15 mg/ml anti-ragweed antibody (n=3/experiment), Group 2 which received 5 mg/ml anti-VEGF antibody (G6.31; WO2005/012359 and WO2005/044853; n=3/experiment) and 10 mg/ml ragweed antibody, Group 3 which received 5 mg/ml G6.31 and 10 mg/ml murine 18F7 (n=4/experiment), and Group 4 which received 5 mg/ml G6.31 and 10 mg/ml hu18F7.v6k (n=4/experiment). The pooled results from three independent experiments are shown in FIG. 31, which demonstrated that the anti-VEGF antibody 66.31 has significant anti-angiogenesis activity, and the combination of G6.31 with either hu18F7.v6k or murine 18F7 significantly enhanced the activity of G6.31. Similar anti-angiogenesis activities were observed in the intestinal villus vasculature. These results confirm that hu18F7.v6k and murine 18F7 have similar anti-angiogenesis activities in this model.

Example 4

Inhibition of Tumor Perfusion and Permeability by Anti-EGFL7 Antibodies in Human Subjects We conducted dynamic contrast-magnetic resonance imaging (DCE-MRI) assessments on human subjects who had been administered with two cycles of 3 mg/kg or 15 mg/kg hu18F7.v6k to explore changes in tumor vasculature in response to the antibody. DCE-MRI is an imaging modality that allows for the functional analysis of tumor microcirculation. Changes in vascular parameters such as $V_e$, the fractional extravascular and extracellular leakage volume, and $K_{trans}$, the volume transfer constant, reflect changes in tumor perfusion and permeability. Two baseline pre-treatment scans were obtained approximately 5-7 days apart (but at least 24 hours apart) prior to dosing in Cycle 1 (for example, Day −1 and Day −7 relative to administration of antibody). Post-treatment scans were obtained on Day 15 of Cycle 1 and on Day 8 of Cycle 2 (±2 days to allow for scheduling difficulties). Evaluable metastatic lesions had to measure ≥3 cm in the liver, or ≥2 cm elsewhere in at least one dimension. In addition to DCE-MRI acquisition sequences, other MRI acquisition sequences, such as diffusion-weighted imaging and T1- and T2-weighted imaging were acquired during the same image acquisition visit for each subject. As shown in Table 10, we observed that treatment with anti-EGFL7 antibodies reduced $F_{trans}$ in some solid tumors by up to approximately 40%.

TABLE 10

| Patent Identifier, liver tumor volume, and hu18F7.v6k dosage | Median $K_{trans}$ | | | |
|---|---|---|---|---|
| | Base 1 | Base 2 | Cycle 1, Day 15 | Cycle 2, Day 8 |
| 3301, 82 cc (3 mg/kg) | ND | 0.021 | 0.0171 | ND |
| 3503, 7 cc (15 mg/kg) | ND | 0.0542 | 0.0435 | 0.0327 |
| 3505, 11 cc (15 mg/kg) | 0.0278 | 0.0288 | 0.0239 | 0.019 |
| 3505, 142 cc (15 mg/kg) | 0.0239 | 0.022 | 0.0229 | 0.02 |
| 3902, 235 cc (3 mg/kg) | 0.022 | 0.019 | 0.02 | 0.022 |

What is claimed is:

1. A method of reducing or inhibiting perfusion and permeability of a tumor which expresses EGFL7 in a subject, the method comprising administering to an individual in need of such treatment an effective amount of an anti-EGFL7 antibody, the antibody comprising a variable domain comprising the following HVR sequences:
HVR-L1 comprising RTSQSLVHINXITYLH, wherein X is G or A (SEQ ID NO: 106, 241);
HVR-L2 comprising RVSNRFS (SEQ ID NO: 101);
HVR-L3 comprising GQSTHVPLT (SEQ ID NO: 131);
HVR-H1 comprising GYTFIDYYMN (SEQ ID NO: 103);
HVR-H2 comprising GDINLDNXGTHYNQKFKG (SEQ ID NO: 104, 242), wherein X is G or S; and
HVR-H3 comprising AREGVYHDYDDYAMDY (SEQ ID NO: 105).

2. A method of reducing or inhibiting perfusion and permeability of a tumor which expresses EGFL7 in a subject, the method comprising administering to an individual in need of such treatment an effective amount of an anti-EGFL7 antibody, wherein the anti-EGFL7 antibody comprises the following HVR sequences: HVR-L1 comprises the amino acid sequence RTSQSLVHINAITYLH (SEQ ID NO: 241), HVR-L2 comprises the amino acid sequence RVSNRFS (SEQ ID NO: 101), HVR-L3 comprises the amino acid sequence GQSTHVPLT (SEQ ID NO: 131), HVR-H1 comprises the amino acid sequence GYTFIDYYMN (SEQ ID NO: 103), HVR-H2 comprises the amino acid sequence GDINLDNSGTHYNQKFKG (SEQ ID NO: 242), and HVR-H3 comprises the amino acid sequence AREGVYHDYDDYAMDY (SEQ ID NO: 105).

3. The method of claim 1 or 2, wherein the heavy chain comprises the following framework sequences: FR-H1 comprises EVQLVESGGGLVQPGGSLRLSCAAS (SEQ ID NO: 197); FR-H2 comprises WVRQAPGKGLEWX$_1$, wherein X$_1$ is I or V (SEQ ID NO: 228); FR-H3 comprises RX$_1$TX$_2$SX$_3$DX$_4$SX$_5$X$_6$TX$_7$YX$_8$QMNSLRAEDTAVYYC, wherein X$_1$ is F or V; X$_2$ is I or L; X$_3$ is selected from the group consisting of L, R, and V; X$_4$ is K or N; X$_5$ is selected from the group consisting of K, N, R, and S; X$_6$ is N or S; X$_7$ is selected from the group consisting of A, L, and V; and X$_8$ is L or M (SEQ ID NO: 229); and FR-H4 comprises WGQGTLVTVSS (SEQ ID NO: 200).

4. The method of claim 3, wherein the heavy chain comprises the following framework sequences: FR-H1 comprises EVQLVESGGGLVQPGGSLRLSCAAS (SEQ ID NO: 197); FR-H2 comprises WVRQAPGKGLEWV (SEQ ID NO: 198); FR-H3 comprises RFTISRDX$_1$SKNTX$_2$YLQMNSLRAEDTAVYYCAR, wherein X$_1$ is N or K; and X$_2$ is selected from the group consisting of A, L, and V (SEQ ID NO: 230); and FR-H4 comprises WGQGTLVTVSS (SEQ ID NO: 200).

5. The method of claim 1 or 2, wherein the light chain comprises the following framework sequences: FR-L1 comprises DIQMTQSPSSLSASVGDRVTITC (SEQ ID NO: 201), FR-L2 comprises WYQQKPGKAPKLLIY (SEQ ID NO: 202), FR-L3 comprises GVPSRFSGSGSGTDFTLTISSLQPEDFATYYC (SEQ ID NO: 203), FR-L4 comprises FGQGTKVEIK (SEQ ID NO: 221) or FGQGTKVEIKR (SEQ ID NO: 204).

6. The method of claim 1, wherein the light chain comprises the variable domain sequence of 18F7.v6 as shown in FIG. 27 (SEQ ID NO: 193) or the variable domain sequence of 18F7.v6k as shown in FIG. 27 (SEQ ID NO: 194).

7. The method of claim 1, wherein the heavy chain comprises the variable domain sequence of 18F7.v6 as shown in FIG. 28 (SEQ ID NO: 195) or the variable domain sequence of 18F7.v6k as shown in FIG. 28 (SEQ ID NO: 196).

8. The method of claim 1, wherein the light chain comprises the variable domain sequence of 18F7.v6 as shown in FIG. 27 (SEQ ID NO: 193) and the heavy chain comprises the variable domain sequence of 18F7.v6 as shown in FIG. 28 (SEQ ID NO: 195).

9. The method of claim 1, wherein the light chain comprises the variable domain sequence of 18F7.v6k as shown in FIG. 27 (SEQ ID NO: 194) and the heavy chain comprises the variable domain sequence of 18F7.v6k as shown in FIG. 28 (SEQ ID NO: 196).

10. The method of claim 1 or 2, wherein at least a portion of the framework sequence is a human consensus framework sequence.

11. The method of claim 10, comprising human κ subgroup 1 consensus framework sequence or heavy chain human subgroup III consensus framework sequence.

12. The method of claim 1 or 2, wherein said antibody is a bispecific antibody.

13. The method of claim 12, wherein said bispecific antibody binds to vascular endothelial growth factor (VEGF).

14. The method of claim 13, wherein said bispecific antibody binds to the same epitope as bevacizumab or ranibizumab.

15. The method of claim 14, wherein said bispecific antibody binds to the same epitope as bevacizumab.

16. The method of claim 1 or 2, wherein the tumor is selected from the group consisting of breast, colorectal, lung, esophageal, bladder, ovarian, pancreatic, and hepatocellular tumor.

17. The method of claim 16, wherein the tumor is a colorectal or lung tumor.

18. The method of claim 1 or 2, further comprising administering to the individual an effective amount of a second medicament, wherein the anti-EGFL7 antibody is a first medicament.

19. The method of claim 18, wherein the second medicament is another antibody, a chemotherapeutic agent, a cytotoxic agent, an anti-angiogenic agent, an immunosuppressive agent, a prodrug, a cytokine, a cytokine antagonist, cytotoxic radiotherapy, a corticosteroid, an anti-emetic, a cancer vaccine, an analgesic, or a growth-inhibitory agent.

20. The method of claim 19, wherein the second medicament is an anti-VEGF antibody.

21. The method of claim 20, where the second medicament is bevacizumab or ranibizumab.

22. The method of claim 21, wherein the second medicament is bevacizumab.

23. The method of claim 22, further comprising administering to the individual an effective amount of a further medicament, wherein the anti-EGFL7 antibody is a first medicament and an anti-VEGF antibody is the second medicament.

24. The method of claim 23, wherein the further medicament is a chemotherapeutic agent.

25. The method of claim 24, wherein the chemotherapeutic agent is FOLFOX.

26. The method of claim 24, wherein the chemotherapeutic agent is carboplatin and paclitaxel.

27. The method of claim 18, further comprising administering to the individual an effective amount of a further medicament, wherein the anti-EGFL7 antibody is a first medicament and an anti-VEGF antibody is the second medicament.

28. The method of claim 27, wherein the further medicament is a chemotherapeutic agent.

29. The method of claim 28, wherein the chemotherapeutic agent is FOLFOX.

30. The method of claim 28, wherein the chemotherapeutic agent is carboplatin and paclitaxel.

* * * * *

SEQUENCE LISTING

<160> NUMBER OF SEQ ID NOS: 247

<210> SEQ ID NO 1
<211> LENGTH: 278
<212> TYPE: PRT
<213> ORGANISM: Mus sp.

<400> SEQUENCE: 1

Met Gln Thr Met Trp Gly Ser Gly Glu Leu Leu Val Ala Trp Phe Leu
1               5                   10                  15

Val Leu Ala Ala Asp Gly Thr Thr Glu His Val Tyr Arg Pro Ser Arg
            20                  25                  30

Arg Val Cys Thr Val Gly Ile Ser Gly Gly Ser Ile Ser Glu Thr Phe

```
                35                  40                  45
Val Gln Arg Val Tyr Gln Pro Tyr Leu Thr Thr Cys Asp Gly His Arg
 50                  55                  60

Ala Cys Ser Thr Tyr Arg Thr Ile Tyr Arg Thr Ala Tyr Arg Arg Ser
 65                  70                  75                  80

Pro Gly Val Thr Pro Ala Arg Pro Arg Tyr Ala Cys Cys Pro Gly Trp
                 85                  90                  95

Lys Arg Thr Ser Gly Leu Pro Gly Ala Cys Gly Ala Ala Ile Cys Gln
                100                 105                 110

Pro Pro Cys Gly Asn Gly Gly Ser Cys Ile Arg Pro Gly His Cys Arg
            115                 120                 125

Cys Pro Val Gly Trp Gln Gly Asp Thr Cys Gln Thr Asp Val Asp Glu
        130                 135                 140

Cys Ser Thr Gly Glu Ala Ser Cys Pro Gln Arg Cys Val Asn Thr Val
145                 150                 155                 160

Gly Ser Tyr Trp Cys Gln Gly Trp Glu Gly Gln Ser Pro Ser Ala Asp
                165                 170                 175

Gly Thr Arg Cys Leu Ser Lys Glu Gly Pro Ser Pro Val Ala Pro Asn
            180                 185                 190

Pro Thr Ala Gly Val Asp Ser Met Ala Arg Glu Glu Val Tyr Arg Leu
        195                 200                 205

Gln Ala Arg Val Asp Val Leu Glu Gln Lys Leu Gln Leu Val Leu Ala
    210                 215                 220

Pro Leu His Ser Leu Ala Ser Arg Ser Thr Glu His Gly Leu Gln Asp
225                 230                 235                 240

Pro Gly Ser Leu Leu Ala His Ser Phe Gln Gln Leu Asp Arg Ile Asp
                245                 250                 255

Ser Leu Ser Glu Gln Val Ser Phe Leu Glu Glu His Leu Gly Ser Cys
            260                 265                 270

Ser Cys Lys Lys Asp Leu
            275

<210> SEQ ID NO 2
<211> LENGTH: 274
<212> TYPE: PRT
<213> ORGANISM: Homo sapiens

<400> SEQUENCE: 2

Met Arg Gly Ser Gln Glu Val Leu Leu Met Trp Leu Leu Val Leu Ala
 1               5                  10                  15

Val Gly Gly Thr Glu His Ala Tyr Arg Pro Gly Arg Arg Val Cys Ala
                20                  25                  30

Val Arg Ala His Gly Asp Pro Val Ser Glu Ser Phe Val Gln Arg Val
            35                  40                  45

Tyr Gln Pro Phe Leu Thr Thr Cys Asp Gly His Arg Ala Cys Ser Thr
 50                  55                  60

Tyr Arg Thr Ile Tyr Arg Thr Ala Tyr Arg Arg Ser Pro Gly Leu Ala
 65                  70                  75                  80

Pro Ala Arg Pro Arg Tyr Ala Cys Cys Pro Gly Trp Lys Arg Thr Ser
                 85                  90                  95

Gly Leu Pro Gly Ala Cys Gly Ala Ala Ile Cys Gln Pro Pro Cys Arg
                100                 105                 110

Asn Gly Gly Ser Cys Val Gln Pro Gly Arg Cys Arg Cys Pro Ala Gly
            115                 120                 125

Trp Arg Gly Asp Thr Cys Gln Ser Asp Val Asp Glu Cys Ser Ala Arg
```

```
                    130                 135                 140
Arg Gly Gly Cys Pro Gln Arg Cys Ile Asn Thr Ala Gly Ser Tyr Trp
145                 150                 155                 160

Cys Gln Cys Trp Glu Gly His Ser Leu Ser Ala Asp Gly Thr Leu Cys
                    165                 170                 175

Val Pro Lys Gly Gly Pro Pro Arg Val Ala Pro Asn Pro Thr Gly Val
            180                 185                 190

Asp Ser Ala Met Lys Glu Glu Val Gln Arg Leu Gln Ser Arg Val Asp
            195                 200                 205

Leu Leu Glu Glu Lys Leu Gln Leu Val Leu Ala Pro Leu His Ser Leu
        210                 215                 220

Ala Ser Gln Ala Leu Glu His Gly Leu Pro Asp Pro Gly Ser Leu Leu
225                 230                 235                 240

Val His Ser Phe Gln Gln Leu Gly Arg Ile Asp Ser Leu Ser Glu Gln
                245                 250                 255

Ile Ser Phe Leu Glu Glu Leu Gly Ser Cys Ser Cys Lys Lys Asp
            260                 265                 270

Ser Gly

<210> SEQ ID NO 3
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Thr Thr Cys Asp Gly His Arg Ala Cys Ser Thr Tyr Arg Thr Ile
1               5                   10                  15

Tyr Arg Thr Ala Tyr Arg Arg Ser Pro Gly
            20                  25

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Pro Ala Arg Pro Arg Tyr Ala Cys Cys Pro Gly Trp Lys Arg Thr Ser
1               5                   10                  15

Gly Leu Pro Gly Ala Cys Gly Ala Ala Ile Cys Gln Pro Pro
            20                  25                  30

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Pro Arg Tyr Ala Cys Cys Pro Gly Trp Lys Arg Thr
1               5                   10

<210> SEQ ID NO 6
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 6

Leu Thr Thr Cys Asp Gly His Arg Ala Cys Ser Thr Tyr
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Cys Ser Thr Tyr Arg Thr Ile Tyr Arg Thr Ala
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Thr Ala Tyr Arg Arg Ser Pro Gly Val Thr Pro Ala
1               5                   10

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys Arg
            100                 105

<210> SEQ ID NO 10
<211> LENGTH: 112
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Ser Val Asp Tyr Asp
            20                  25                  30

Gly Asp Ser Tyr Met Ser Trp Tyr Gln Gln Lys Pro Gly Lys Ala Pro
        35                  40                  45

Lys Leu Leu Ile Tyr Gly Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Val Glu Ile Lys Arg
            100                 105                 110
```

```
<210> SEQ ID NO 11
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Asp Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Phe Asp Tyr Trp Gly Gln Gly Thr Leu Val Thr Val Ser
            100                 105                 110

Ser
```

```
<210> SEQ ID NO 12
<211> LENGTH: 117
<212> TYPE: PRT
<213> ORGANISM: Homo sapiens

<400> SEQUENCE: 12

Glu Val Gln Leu Val Glu Ser Gly Gly Gly Leu Val Gln Pro Gly Gly
 1               5                   10                  15

Ser Leu Arg Leu Ser Cys Ala Ala Ser Gly His Thr Phe Thr Thr Tyr
            20                  25                  30

Gly Met Ser Trp Val Arg Gln Ala Pro Gly Lys Gly Leu Glu Trp Val
        35                  40                  45

Gly Trp Ile Asn Thr His Ser Gly Val Pro Thr Tyr Ala Asp Asp Phe
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Gly Ser Ser Ala Val Asp Tyr Trp Gly Gln Gly Thr Leu
```

Val Thr Val Ser Ser
        115

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(39)

<400> SEQUENCE: 13 gcc tat gca gat atc cag atg acc cag tcc ccg agc tcc      39
Ala Tyr Ala Asp Ile Gln Met Thr Gln Ser Pro Ser Ser
1               5                  10

<210> SEQ ID NO 14
<211> LENGTH: 13
<212> TYPE: PRT
<213> ORGANISM: Artificial Sequence
<220> FEATURE:
<223> OTHER INFORMATION: Synthetic Construct

<400> SEQUENCE: 14

Ala Tyr Ala Asp Ile Gln Met Thr Gln Ser Pro Ser Ser
1               5                  10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Ile Val Leu Thr Gln Ser Pro Ala Ser
1               5                  10

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcctatcgag atatccagmt cacccagtcc ccgagctcc      39

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(39)

<400> SEQUENCE: 17 aca aac gcg tac gct gag gtt cag ctg gtg gag tct ggc      39
Thr Asn Ala Tyr Ala Glu Val Gln Leu Val Glu Ser Gly
1               5                  10

<210> SEQ ID NO 18
<211> LENGTH: 13
<212> TYPE: PRT
<213> ORGANISM: Artificial Sequence
<220> FEATURE:
<223> OTHER INFORMATION: Synthetic Construct

<400> SEQUENCE: 18

Thr Asn Ala Tyr Ala Glu Val Gln Leu Val Glu Ser Gly
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ile Gln Leu Val Gln Ser Gly
1               5

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
acaaacgcgt acgctgagrt ccagctggtg gagtctggc                              39

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 21 ggt aag ggc ctg gaa tgg gtt gca agg att tat cct                         36
Gly Lys Gly Leu Glu Trp Val Ala Arg Ile Tyr Pro
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Construct

<400> SEQUENCE: 22

Gly Lys Gly Leu Glu Trp Val Ala Arg Ile Tyr Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Lys Gly Leu Lys Trp Met Gly Trp Ile Asn Thr
1               5                   10

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggtaagggcc tggaatggrt ggcaaggatt tatcct                             36

<210> SEQ ID NO 25
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(102)

<400> SEQUENCE: 25 gtc aag ggc cgt ttc act ata agc cgc gac aac tcc aaa aac aca ctg     48
Val Lys Gly Arg Phe Thr Ile Ser Arg Asp Asn Ser Lys Asn Thr Leu
1               5                   10                  15 tac cta caa atg aac agc gag gac act gcc gtc tat tat tgt agc cgc     96
Tyr Leu Gln Met Asn Ser Glu Asp Thr Ala Val Tyr Tyr Cys Ser Arg
            20                  25                  30 tgg gga                                                            102
Trp Gly

<210> SEQ ID NO 26
<211> LENGTH: 34
<212> TYPE: PRT
<213> ORGANISM: Artificial Sequence
<220> FEATURE:
<223> OTHER INFORMATION: Synthetic Construct

<400> SEQUENCE: 26

Val Lys Gly Arg Phe Thr Ile Ser Arg Asp Asn Ser Lys Asn Thr Leu
1               5                   10                  15

Tyr Leu Gln Met Asn Ser Glu Asp Thr Ala Val Tyr Tyr Cys Ser Arg
            20                  25                  30

Trp Gly

<210> SEQ ID NO 27
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Phe Lys Gly Arg Phe Ala Phe Ser Leu Glu Thr Ser Ala Ser Thr Ala
1               5                   10                  15

His Leu Gln Ile Asn Asn Glu Asp Thr Ala Thr Tyr Phe Cys Ala Arg
            20                  25                  30

Leu Gly

<210> SEQ ID NO 28
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gtcaagggcc gtttcactwt cagcckcgac amctccrmaa rcacarygta cctacaaatg     60
aacagcgagg acactgccgt ctattwctgt gcgcgtctgg gt                       102

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ser Pro Gly Leu Ala Pro Ala Arg Pro Arg Tyr Ala
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Trp Lys Arg Thr Ser Gly Leu Pro Gly Ala Cys Gly
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Ala Ser Gln Ser Val Asp Tyr Asp Gly Asp Ser Tyr Met Ser
1               5                   10                  15

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Ala Ser Asn Leu Glu Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 33

Gln Gln Asn Asn Glu Asp Pro Tyr Thr
1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly His Thr Phe Thr Thr Tyr Gly Met Ser
1               5                   10

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Trp Ile Asn Thr His Ser Gly Val Pro Thr Tyr Ala Asp Asp Phe
1               5                   10                  15

Lys Gly

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Arg Leu Gly Ser Ser Ala Val Asp Tyr
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Arg Ser Gln Ser Val Asp Tyr Asp Gly Asp Ser Tyr Met Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Ala Ser His Ser Val Asp Tyr Asp Gly Asp Ser Tyr Met Ser
1               5                   10                  15

<210> SEQ ID NO 39
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Ala Ser Gln Ser Gly Asp Tyr Asp Gly Asp Ser Tyr Met Ser
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Ala Ser Gln Ser Val Asp Tyr Arg Gly Asp Ser Tyr Met Ser
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Ala Ser Gln Ser Val Asp Tyr Asp Gly Asp Ser Tyr Val Ser
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Ala Ser Gln Ser Val Asp Tyr Leu Gly Asp Ser Tyr Met Ser
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Ala Ser Gln Ser Val Asp Tyr Trp Gly Asp Ser Tyr Met Ser
1               5                   10                  15

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Ala Ser Tyr Leu Glu Ser
```

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Ala Ser Asn Arg Glu Ser
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Ala Ser Asn Tyr Glu Ser
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Ala Ser Asn Leu Glu Gln
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gln Asn Asn Glu Asp Pro Phe Thr
1               5

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly His Thr Gly Thr Thr Tyr Gly Met Ser
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 50

Gly His Thr Phe Thr Thr Tyr Gly Tyr Ser
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly His Thr Phe Asp Thr Tyr Gly Met Ser
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly His Thr Phe Arg Thr Tyr Gly Met Ser
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Val Thr Phe Thr Thr Tyr Gly Met Ser
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly His Arg Phe Thr Thr Tyr Gly Met Ser
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly His Thr Phe Gly Thr Tyr Gly Met Ser
1               5                   10

<210> SEQ ID NO 56
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 56

Gly His Thr Arg Thr Thr Tyr Gly Met Ser
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly His Thr Ser Thr Thr Tyr Gly Met Ser
1               5                   10

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Trp Ile Asn Trp His Ser Gly Val Pro Thr Tyr Ala Asp Asp Phe
1               5                   10                  15

Lys Gly

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Trp Ile Asn Met His Ser Gly Val Pro Thr Tyr Ala Asp Asp Phe
1               5                   10                  15

Lys Gly

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Trp Ile Asn Thr His Ser Gly Val Pro Thr Met Ala Asp Asp Phe
1               5                   10                  15

Lys Gly

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 61

Gly Trp Ile Asn Thr His Ser Gly Val Pro Thr Tyr Ala His Asp Phe
1               5                   10                  15

Lys Gly

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Any amino acid

<400> SEQUENCE: 62

Gly Trp Ile Asn Thr His Ser Gly Val Pro Thr Tyr Ala Asp Xaa Phe
1               5                   10                  15

Lys Gly

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Trp Ile Asn Ile His Ser Gly Val Pro Thr Tyr Ala Asp Asp Phe
1               5                   10                  15

Lys Gly

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Trp Ile Asn Trp His Ser Gly Val Pro Thr Tyr Ala Asp Asp Phe
1               5                   10                  15

Lys Gly

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Trp Ile Asn Thr Arg Ser Gly Val Pro Thr Tyr Ala Asp Asp Phe
1               5                   10                  15

Lys Gly

<210> SEQ ID NO 66
<211> LENGTH: 18
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 66

Gly Trp Ile Asn Thr His Ser Gly Val Pro Thr Ile Ala Asp Asp Phe
1               5                   10                  15

Lys Gly

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Trp Ile Asn Thr His Ser Gly Val Pro Thr Tyr Ala Asp Asp Phe
1               5                   10                  15

Ser Gly

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Trp Ile Asn Thr His Ser Gly Val Pro Thr Thr Ala Asp Asp Phe
1               5                   10                  15

Lys Gly

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Trp Ile Asn Thr His Ser Gly Val Pro Thr Tyr Ala Asp Thr Phe
1               5                   10                  15

Lys Gly

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Trp Ile Asn Ile His Ser Gly Val Pro Thr Tyr Ala Asp Asp Phe
1               5                   10                  15

Lys Gly

<210> SEQ ID NO 71
<211> LENGTH: 18
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 71

Gly Trp Ile Asn Thr His Ser Gly Val Pro Thr Tyr Ala Asp Met Phe
1               5                   10                  15

Lys Gly

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Trp Ile Asn Thr His Ser Gly Val Pro Thr Tyr Ala Asp Asp Tyr
1               5                   10                  15

Lys Gly

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Trp Ile Asn Thr His Ser Gly Val Pro Thr Tyr Ala Asp Asp Phe
1               5                   10                  15

Lys Arg

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Asn Leu Gly Ser Ser Ala Val Asp Tyr
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Arg Leu Gly Ser Cys Ala Val Asp Tyr
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 76

Ala Arg Leu Gly Ser Tyr Ala Val Asp Tyr
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Arg Leu Gly Ser Ser Ala Val Asp Ala
1               5                   10

<210> SEQ ID NO 78
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Ser
            20                  25                  30

Gly Asp Ser Tyr Met Ser Trp Tyr Gln Gln Lys Pro Gly Lys Ala Pro
        35                  40                  45

Lys Leu Leu Ile Tyr Gly Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Glu Pro Tyr Thr Phe Gly Gln Gly Thr Lys Val Glu Ile Lys Arg
            100                 105                 110

<210> SEQ ID NO 79
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Ser
            20                  25                  30

Gly Asp Ser Tyr Met Ser Trp Tyr Gln Gln Lys Pro Gly Lys Ala Pro
        35                  40                  45

Lys Leu Leu Ile Tyr Gly Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95
```

```
Glu Glu Pro Tyr Thr Phe Gly Gln Gly Thr Lys Val Glu Ile Lys Arg
            100                 105                 110
```

<210> SEQ ID NO 80
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Glu Val Gln Leu Val Glu Ser Gly Gly Gly Leu Val Gln Pro Gly Gly
1               5                   10                  15

Ser Leu Arg Leu Ser Cys Ala Ala Ser Gly His Thr Phe Thr Thr Tyr
            20                  25                  30

Gly Met Ser Trp Val Arg Gln Ala Pro Gly Lys Gly Leu Glu Trp Val
        35                  40                  45

Gly Trp Ile Asn Thr His Ser Gly Val Pro Thr Tyr Ala Asp Asp Phe
    50                  55                  60

Lys Gly Arg Phe Thr Ile Ser Leu Asp Asn Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Leu Gly Ser Ser Ala Val Asp Tyr Trp Gly Gln Gly Thr Leu
            100                 105                 110

Val Thr Val Ser Ser
        115
```

<210> SEQ ID NO 81
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Glu Val Gln Leu Val Glu Ser Gly Gly Gly Leu Val Gln Pro Gly Gly
1               5                   10                  15

Ser Leu Arg Leu Ser Cys Ala Ala Ser Gly His Thr Phe Thr Thr Tyr
            20                  25                  30

Gly Met Ser Trp Val Arg Gln Ala Pro Gly Lys Gly Leu Glu Trp Val
        35                  40                  45

Gly Trp Ile Asn Thr His Ser Gly Val Pro Thr Tyr Ala Asp Asp Phe
    50                  55                  60

Lys Gly Arg Phe Thr Ile Ser Leu Asp Asn Ser Lys Ser Thr Ala Tyr
65                  70                  75                  80

Leu Gln Met Asn Ser Leu Arg Ala Glu Asp Thr Ala Val Tyr Phe Cys
            85                  90                  95

Ala Arg Leu Gly Ser Ser Ala Val Asp Tyr Trp Gly Gln Gly Thr Leu
            100                 105                 110

Val Thr Val Ser Ser
        115
```

<210> SEQ ID NO 82
<211> LENGTH: 112
<212> TYPE: PRT
<213> ORGANISM: Artificial Sequence
<220> FEATURE:

-continued

<223> OTHER INFORMATION: Description of Artificial Sequence: Synthetic
     polypeptide

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Ser
            20                  25                  30

Gly Asp Ser Tyr Met Ser Trp Tyr Gln Gln Lys Pro Gly Lys Ala Pro
        35                  40                  45

Lys Leu Leu Ile Tyr Gly Ala Ser Tyr Arg Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Glu Pro Tyr Thr Phe Gly Gln Gly Thr Lys Val Glu Ile Lys Arg
            100                 105                 110

<210> SEQ ID NO 83
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Ser
            20                  25                  30

Gly Asp Ser Tyr Met Ser Trp Tyr Gln Gln Lys Pro Gly Lys Ala Pro
        35                  40                  45

Lys Leu Leu Ile Tyr Gly Ala Ser Tyr Arg Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Glu Pro Tyr Thr Phe Gly Gln Gly Thr Lys Val Glu Ile Lys Arg
            100                 105                 110

<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly His Thr Phe Thr Thr Tyr
            20                  25                  30

Gly Met Ser Trp Val Arg Gln Ala Pro Gly Lys Gly Leu Glu Trp Val
        35                  40                  45

Gly Trp Ile Asn Thr His Ser Gly Val Pro Thr Tyr Ala Asp Asp Phe
    50                  55                  60

```
Lys Gly Arg Phe Thr Ile Ser Leu Asp Asn Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ala Arg Leu Gly Ser Tyr Ala Val Asp Tyr Trp Gly Gln Gly Thr Leu
            100                 105                 110

Val Thr Val Ser Ser
115

<210> SEQ ID NO 85
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Ile Gln Leu Val Glu Ser Gly Gly Gly Leu Val Gln Pro Gly Gly
  1               5                  10                  15

Ser Leu Arg Leu Ser Cys Ala Ala Ser Gly His Thr Phe Thr Thr Tyr
             20                  25                  30

Gly Met Ser Trp Val Arg Gln Ala Pro Gly Lys Gly Leu Glu Trp Met
         35                  40                  45

Gly Trp Ile Asn Thr His Ser Gly Val Pro Thr Tyr Ala Asp Asp Phe
     50                  55                  60

Lys Gly Arg Phe Thr Ile Ser Leu Asp Asn Ser Lys Ser Thr Ala Tyr
 65                  70                  75                  80

Leu Gln Met Asn Ser Leu Arg Ala Glu Asp Thr Ala Val Tyr Phe Cys
             85                  90                  95

Ala Arg Leu Gly Ser Tyr Ala Val Asp Tyr Trp Gly Gln Gly Thr Leu
            100                 105                 110

Val Thr Val Ser Ser
115

<210> SEQ ID NO 86
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Ser Leu Ser Ala Ser Val Gly
  1               5                  10                  15

Asp Arg Val Thr Ile Thr Cys Arg Thr Ser Gln Ser Leu Val His Ile
             20                  25                  30

Asn Gly Ile Thr Tyr Leu His Trp Tyr Gln Gln Lys Pro Gly Lys Ala
         35                  40                  45

Pro Lys Leu Leu Ile Tyr Arg Val Ser Asn Arg Phe Ser Gly Val Pro
     50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Ser Gln Ser
             85                  90                  95

Thr His Val Pro Leu Thr Phe Gly Gln Gly Thr Lys Val Glu Ile Lys
            100                 105                 110
```

<210> SEQ ID NO 87
<211> LENGTH: 123
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ile Asp Tyr
            20                  25                  30

Tyr Met Asn Trp Val Arg Gln Ala Pro Gly Lys Gly Leu Glu Trp Val
        35                  40                  45

Gly Asp Ile Asn Leu Asp Asn Gly Gly Thr His Tyr Asn Gln Lys Phe
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Val Tyr His Asp Tyr Asp Tyr Ala Met Asp Tyr
            100                 105                 110

Trp Gly Gln Gly Thr Leu Val Thr Val Ser Ser
        115                 120

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 88

Glu Asp Phe Ala Thr Tyr Tyr Cys Ser Gln Ser Thr His
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 89

Glu Asp Leu Gly Val Tyr Phe Cys Ser Gln Ser Thr His
1               5                   10

<210> SEQ ID NO 90
<211> LENGTH: 39
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 90
gaagacttcg caacttatta ctgtagccag agcacccac                    39

<210> SEQ ID NO 91

```
<210> SEQ ID NO 91
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gaagacttcg caacttattw ctgtagccag agcacccac                                39

<210> SEQ ID NO 92
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Lys Gly Leu Glu Trp Val Gly Asp Ile Asn Leu Asp
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Lys Ser Leu Glu Trp Ile Gly Asp Ile Asn Leu Asp
1               5                   10

<210> SEQ ID NO 94
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ggtaagggcc tggaatgggt tggtgatatc aacctggat                                39

<210> SEQ ID NO 95
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ggtaagggcc tggaatggrt cggtgatatc aacctggat                                39

<210> SEQ ID NO 96
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Lys Phe Lys Gly Arg Phe Thr Ile Ser Arg Asp Thr Ser Lys Asn
1               5                   10                  15

Thr Leu Tyr Leu Gln Met Asn Ser Leu Arg
```

```
<210> SEQ ID NO 97
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Lys Phe Lys Gly Lys Ala Thr Leu Thr Val Asp Lys Ser Ser Ser
1               5                   10                  15

Thr Ala Tyr Met Glu Leu His Ser Leu Thr
            20                  25

<210> SEQ ID NO 98
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cagaaattca aggtcgttt cactataagc cgcgacacct ccaaaaacac actgtaccta      60
caaatgaaca gcttaaga                                                  78

<210> SEQ ID NO 99
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
cagaaattca aggtcgtky cactmtcagc sktgacamgt ccarsarcac asygtacmtg      60
caaatgaaca gcttaaga                                                  78

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Thr Ser Gln Ser Leu Val His Ile Asn Gly Ile Thr Tyr Leu His
1               5                   10                  15

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Val Ser Asn Arg Phe Ser
1               5

<210> SEQ ID NO 102
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Gln Ser Thr His Val Pro Leu Thr
1               5

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Tyr Thr Phe Ile Asp Tyr Tyr Met Asn
1               5                   10

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Asp Ile Asn Leu Asp Asn Gly Gly Thr His Tyr Asn Gln Lys Phe
1               5                   10                  15

Lys Gly

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Arg Glu Gly Val Tyr His Asp Tyr Asp Asp Tyr Ala Met Asp Tyr
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Thr Ser Gln Ser Leu Val His Ile Asn Gly Ile Thr Tyr Leu His
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107
```

Arg Thr Ser Gln Ser Leu Val His Tyr Asn Gly Ile Thr Tyr Leu His
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Thr Ser Gln Ser Leu Val Pro Ile Asn Gly Ile Thr Tyr Leu His
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Thr Ser Gln Ser Leu Val His Ile Asn Gly Ile Thr Tyr Leu His
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Thr Ser Gln Ser Leu Val His Leu Asn Gly Ile Thr Tyr Leu His
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Leu Thr Ser Gln Ser Leu Val His Ile Asn Gly Ile Thr Tyr Leu His
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Trp Ser Gln Ser Leu Val His Ile Asn Gly Ile Thr Tyr Leu His
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Arg Pro Ser Gln Ser Leu Val His Ile Asn Gly Ile Thr Tyr Leu His
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Thr His Gln Ser Leu Val His Ile Asn Gly Ile Thr Tyr Leu His
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Thr Ser Gln Ser Val Val His Ile Asn Gly Ile Thr Tyr Leu His
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Thr Ser Gln Ser Leu Val His Thr Asn Gly Ile Thr Tyr Leu His
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Thr Ser Gln Ser Leu Val His Leu Asn Gly Ile Thr Tyr Leu His
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Thr Ser Gln Ser Leu Val His Pro Asn Gly Ile Thr Tyr Leu His
1               5                   10                  15

<210> SEQ ID NO 119
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Thr Ser Gln Ser Leu Val His Ile Asn Gly Ile Thr Tyr Leu Gly
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Thr Thr Ser Gln Ser Leu Val His Ile Asn Gly Ile Thr Tyr Leu His
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Leu Thr Ser Gln Ser Leu Val His Ile Asn Gly Ile Thr Tyr Leu His
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Arg Thr Ser Asp Ser Leu Val His Ile Asn Gly Ile Thr Tyr Leu His
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Arg Thr Ser Gln Gly Leu Val His Ile Asn Gly Ile Thr Tyr Leu His
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Thr Ser Gln Ser Leu Val His Tyr Asn Gly Ile Thr Tyr Leu His
1               5                   10                  15
```

```
<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Val Ser Asn Asp Phe Ser
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Arg Val Ser Asn Arg Ile Ser
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Val Ser Asn Arg Thr Ser
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Val Ser Asn Arg Gly Ser
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Arg Val Ser Asn Arg Ala Ser
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 130

Ala Gln Ser Thr His Val Pro Leu Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Gln Ser Thr His Val Pro Leu Thr
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Leu Gln Ser Thr His Val Pro Leu Thr
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Gln Ser Cys His Val Pro Leu Thr
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ser Gln Ser Thr Phe Val Pro Leu Thr
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Gln Ser Thr His Val Pro Leu Thr
1               5

<210> SEQ ID NO 136
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 136

Gly Gln Ser Thr His Val Pro Leu Thr
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Leu Gln Ser Thr His Val Pro Leu Thr
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Gln Ser Thr His Val Pro Leu Thr
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asn Gln Ser Thr His Val Pro Leu Thr
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Gln Ser Thr His Val Pro Leu Thr
1               5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ile Gln Ser Thr His Val Pro Leu Thr
1               5
```

-continued

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Leu Gln Ser Thr His Val Pro Leu Thr
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Val Gln Ser Thr His Val Pro Leu Thr
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Thr Gln Ser Thr His Val Pro Leu Thr
1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Lys Gln Ser Thr His Val Pro Leu Thr
1               5

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Tyr Thr Val Ile Asp Tyr Tyr Met Asn
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Tyr Thr Phe Ile Asp Tyr Tyr Ile Asn
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Tyr Asn Phe Ile Asp Tyr Tyr Met Asn
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Tyr Thr Phe Met Asp Tyr Tyr Met Asn
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Tyr Thr Phe Arg Asp Tyr Tyr Met Asn
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Tyr Thr Phe Ser Asp Tyr Tyr Met Asn
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Tyr Thr Phe Ile Asp Gln Tyr Met Asn
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic

```
                            peptide

<400> SEQUENCE: 153

Gly Tyr Thr Phe Ile Asp Lys Tyr Met Asn
1               5                   10

<210> SEQ ID NO 154
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Asp Ile Asn Leu Asp Gly Gly Thr His Tyr Asn Gln Lys Phe
1               5                   10                  15

Lys Gly

<210> SEQ ID NO 155
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Asp Ile Asn Leu Asp Asn Gly Lys Thr His Tyr Asn Gln Lys Phe
1               5                   10                  15

Lys Gly

<210> SEQ ID NO 156
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Asp Ile Asn Leu Leu Asn Gly Gly Thr His Tyr Asn Gln Lys Phe
1               5                   10                  15

Lys Gly

<210> SEQ ID NO 157
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Asp Ile Asn Leu Asp Asn Gly Arg Thr His Tyr Asn Gln Lys Phe
1               5                   10                  15

Lys Gly

<210> SEQ ID NO 158
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 158

Gly Asp Ile Asn Leu Asp Asn Gly Ile Thr His Tyr Asn Gln Lys Phe
1               5                   10                  15

Lys Gly

<210> SEQ ID NO 159
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Asp Ile Asn Leu Asp Asn Gly Gly Gly His Tyr Asn Gln Lys Phe
1               5                   10                  15

Lys Gly

<210> SEQ ID NO 160
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Asp Ile Asn Leu Asp Asn Gly Gly Thr His Tyr Ser Gln Lys Phe
1               5                   10                  15

Lys Gly

<210> SEQ ID NO 161
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Asp Ile Asn Leu Asp Asn Gly Gly Thr His Tyr Asn Asn Lys Phe
1               5                   10                  15

Lys Gly

<210> SEQ ID NO 162
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Asp Ile Asn Leu Asp Asn Gly Gly Thr His Tyr Asn Gln Lys Gln
1               5                   10                  15

Lys Gly

<210> SEQ ID NO 163
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 163

Gly Asp Ile Asn Leu Asp Asn Gly Gly Thr His Tyr Asn Gln Lys Phe
1               5                   10                  15

Thr Gly

<210> SEQ ID NO 164
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Asp Ile Asn Leu Asp Asn Gly Gly Thr His Tyr Asn Gln Lys Phe
1               5                   10                  15

Lys His

<210> SEQ ID NO 165
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Asp Ile Asn Leu Asp Asn Gly Gly Thr His Tyr Asn Gln Lys Phe
1               5                   10                  15

Lys Ser

<210> SEQ ID NO 166
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Asp Ile Asn Ala Asp Asn Gly Gly Thr His Tyr Asn Gln Lys Phe
1               5                   10                  15

Lys Gly

<210> SEQ ID NO 167
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Asp Ile Asn Leu Asp Asn Gly Thr Thr His Tyr Asn Gln Lys Phe
1               5                   10                  15

Lys Gly

<210> SEQ ID NO 168
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 168

Gly Asp Ile Asn Leu Asp Asn Gly Gly Thr His Tyr Asn Ala Lys Phe
1               5                   10                  15

Lys Gly

<210> SEQ ID NO 169
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Asp Ile Asn Leu Asp Asn Gly Gly Thr His Tyr Asn Asn Lys Phe
1               5                   10                  15

Lys Gly

<210> SEQ ID NO 170
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Asp Ile Asn Leu Asp Asn Gly Gly Thr His Tyr Asn Gln Val Phe
1               5                   10                  15

Lys Gly

<210> SEQ ID NO 171
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Asp Ile Asn Leu Asp Asn Gly Gly Thr His Tyr Asn Gln Lys Phe
1               5                   10                  15

Lys Arg

<210> SEQ ID NO 172
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Asp Ile Asn Leu Asp Arg Gly Gly Thr His Tyr Asn Gln Lys Phe
1               5                   10                  15

Lys Gly

<210> SEQ ID NO 173
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 173

Gly Asp Ile Asn Asn Asp Asn Gly Gly Thr His Tyr Asn Gln Lys Phe
1               5                   10                  15

Lys Gly

<210> SEQ ID NO 174
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Asp Ile Asn Pro Asp Asn Gly Gly Thr His Tyr Asn Gln Lys Phe
1               5                   10                  15

Lys Gly

<210> SEQ ID NO 175
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Asp Ile Asn Leu Arg Asn Gly Gly Thr His Tyr Asn Gln Lys Phe
1               5                   10                  15

Lys Gly

<210> SEQ ID NO 176
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Asp Ile Asn Leu Asp Tyr Gly Gly Thr His Tyr Asn Gln Lys Phe
1               5                   10                  15

Lys Gly

<210> SEQ ID NO 177
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Asp Ile Asn Leu Asp Ser Gly Gly Thr His Tyr Asn Gln Lys Phe
1               5                   10                  15

Lys Gly

<210> SEQ ID NO 178
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 178

Gly Asp Ile Asn Leu Asp Arg Gly Gly Thr His Tyr Asn Gln Lys Phe
1               5                   10                  15

Lys Gly

<210> SEQ ID NO 179
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Asp Ile Asn Leu Asp Lys Gly Gly Thr His Tyr Asn Gln Lys Phe
1               5                   10                  15

Lys Gly

<210> SEQ ID NO 180
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Asp Ile Asn Leu Asp Asn Gly Val Thr His Tyr Asn Gln Lys Phe
1               5                   10                  15

Lys Gly

<210> SEQ ID NO 181
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Asp Ile Asn Leu Asp Asn Gly Ser Thr His Tyr Asn Gln Lys Phe
1               5                   10                  15

Lys Gly

<210> SEQ ID NO 182
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Asp Ile Asn Leu Asp Asn Gly Gly Arg His Tyr Asn Gln Lys Phe
1               5                   10                  15

Lys Gly

<210> SEQ ID NO 183
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 183

Gly Asp Ile Asn Leu Asp Asn Gly Gly Thr His Val Asn Gln Lys Phe
1               5                   10                  15

Lys Gly

<210> SEQ ID NO 184
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Asp Ile Asn Leu Asp Asn Gly Gly Thr His Ile Asn Gln Lys Phe
1               5                   10                  15

Lys Gly

<210> SEQ ID NO 185
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Asp Ile Asn Leu Asp Asn Gly Gly Thr His Leu Asn Gln Lys Phe
1               5                   10                  15

Lys Gly

<210> SEQ ID NO 186
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Asp Ile Asn Leu Asp Asn Gly Gly Thr His Tyr Asn Gln Lys Phe
1               5                   10                  15

Lys Arg

<210> SEQ ID NO 187
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gly Asp Ile Asn Leu Asp Asn Gly Gly Thr His Tyr Asn Gln Lys Phe
1               5                   10                  15

Lys Ser

<210> SEQ ID NO 188
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 188

Asn Arg Glu Gly Val Tyr His Asp Tyr Asp Asp Tyr Ala Met Asp Tyr
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Thr Arg Glu Gly Val Tyr His Asp Tyr Asp Asp Tyr Ala Met Asp Tyr
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ala Arg Glu Gly Val Tyr His Pro Tyr Asp Asp Tyr Ala Met Asp Tyr
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ala Arg Glu Gly Val Tyr His Pro Tyr Asp Asp Tyr Ala Met Asp Tyr
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ala Arg Glu Gly Val Tyr His Asp Tyr Asp Asp Tyr Ala Trp Asp Tyr
1               5                   10                  15

<210> SEQ ID NO 193
<211> LENGTH: 113
<212> TYPE: PRT
<213> ORGANISM: Homo sapiens

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Val His Ile
                20                  25                  30

Asn Gly Ile Thr Tyr Leu His Trp Tyr Gln Gln Lys Pro Gly Lys Ala
            35                  40                  45

Pro Lys Leu Leu Ile Tyr Arg Val Ser Asn Arg Phe Ser Gly Val Pro
        50                  55                  60
```

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gly Gln Ser
                85                  90                  95

Thr His Val Pro Leu Thr Phe Gly Gln Gly Thr Lys Val Glu Ile Lys
            100                 105                 110

Arg

<210> SEQ ID NO 194
<211> LENGTH: 113
<212> TYPE: PRT
<213> ORGANISM: Homo sapiens

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Val His Ile
            20                  25                  30

Asn Ala Ile Thr Tyr Leu His Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gly Gln Ser
                85                  90                  95

Thr His Val Pro Leu Thr Phe Gly Gln Gly Thr Lys Val Glu Ile Lys
            100                 105                 110

Arg

<210> SEQ ID NO 195
<211> LENGTH: 123
<212> TYPE: PRT
<213> ORGANISM: Homo sapiens

<400> SEQUENCE: 195

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ile Asp Tyr
            20                  25                  30

Tyr Met Asn Trp Val Arg Gln Ala Pro Gly Lys Gly Leu Glu Trp Val
        35                  40                  45

Gly Asp Ile Asn Leu Asp Asn Gly Gly Thr His Tyr Asn Gln Lys Phe
    50                  55                  60

Lys Gly Arg Phe Thr Ile Ser Arg Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Val Tyr His Asp Tyr Asp Tyr Ala Met Asp Tyr
            100                 105                 110

Trp Gly Gln Gly Thr Leu Val Thr Val Ser Ser
        115                 120

<210> SEQ ID NO 196
<211> LENGTH: 123
<212> TYPE: PRT
<213> ORGANISM: Homo sapiens

<400> SEQUENCE: 196

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Ile Asp Tyr
            20                  25                  30
Tyr Met Asn Trp Val Arg Gln Ala Pro Gly Lys Gly Leu Glu Trp Val
        35                  40                  45
Gly Asp Ile Asn Leu Asp Asn Ser Gly Thr His Tyr Asn Gln Lys Phe
    50                  55                  60
Lys Gly Arg Phe Thr Ile Ser Arg Asp Lys Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Glu Gly Val Tyr His Asp Tyr Asp Tyr Ala Met Asp Tyr
            100                 105                 110
Trp Gly Gln Gly Thr Leu Val Thr Val Ser Ser
        115                 120

<210> SEQ ID NO 197
<211> LENGTH: 25
<212> TYPE: PRT
<213> ORGANISM: Homo sapiens

<400> SEQUENCE: 197

Glu Val Gln Leu Val Glu Ser Gly Gly Gly Leu Val Gln Pro Gly Gly
1               5                   10                  15
Ser Leu Arg Leu Ser Cys Ala Ala Ser
            20                  25

<210> SEQ ID NO 198
<211> LENGTH: 13
<212> TYPE: PRT
<213> ORGANISM: Homo sapiens

<400> SEQUENCE: 198

Trp Val Arg Gln Ala Pro Gly Lys Gly Leu Glu Trp Val
1               5                   10

<210> SEQ ID NO 199
<211> LENGTH: 30
<212> TYPE: PRT
<213> ORGANISM: Homo sapiens

<400> SEQUENCE: 199

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys
            20                  25                  30

<210> SEQ ID NO 200
<211> LENGTH: 11
<212> TYPE: PRT
<213> ORGANISM: Homo sapiens

<400> SEQUENCE: 200

Trp Gly Gln Gly Thr Leu Val Thr Val Ser Ser
1               5                   10

<210> SEQ ID NO 201
<211> LENGTH: 23

```
<212> TYPE: PRT
<213> ORGANISM: Homo sapiens

<400> SEQUENCE: 201

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 202
<211> LENGTH: 15
<212> TYPE: PRT
<213> ORGANISM: Homo sapiens

<400> SEQUENCE: 202

Trp Tyr Gln Gln Lys Pro Gly Lys Ala Pro Lys Leu Leu Ile Tyr
1               5                   10                  15

<210> SEQ ID NO 203
<211> LENGTH: 32
<212> TYPE: PRT
<213> ORGANISM: Homo sapiens

<400> SEQUENCE: 203

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 204
<211> LENGTH: 11
<212> TYPE: PRT
<213> ORGANISM: Homo sapiens

<400> SEQUENCE: 204

Phe Gly Gln Gly Thr Lys Val Glu Ile Lys Arg
1               5                   10

<210> SEQ ID NO 205
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ala or Arg
<220> FEATURE:
<221> NAME/KEY: MOD_RES
<222> LOCATION: (8)..(8)
<223> OTHER INFORMATION: Thr or Asn
<220> FEATURE:
<221> NAME/KEY: MOD_RES
<222> LOCATION: (13)..(13)
<223> OTHER INFORMATION: Ala or Leu

<400> SEQUENCE: 205

Arg Phe Thr Ile Ser Xaa Asp Xaa Ser Lys Asn Thr Xaa Tyr Leu Gln
1               5                   10                  15

Met Asn Ser Leu Arg Ala Glu Asp Thr Ala Val Tyr Tyr Cys
            20                  25                  30

<210> SEQ ID NO 206
<211> LENGTH: 31
<212> TYPE: PRT
```

<213> ORGANISM: Homo sapiens

<400> SEQUENCE: 206

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 207
<211> LENGTH: 32
<212> TYPE: PRT
<213> ORGANISM: Homo sapiens

<400> SEQUENCE: 207

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 208
<211> LENGTH: 31
<212> TYPE: PRT
<213> ORGANISM: Homo sapiens

<400> SEQUENCE: 208

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser
            20                  25                  30

<210> SEQ ID NO 209
<211> LENGTH: 32
<212> TYPE: PRT
<213> ORGANISM: Homo sapiens

<400> SEQUENCE: 209

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Arg
<220> FEATURE:
<221> NAME/KEY: MOD_RES
<222> LOCATION: (4)..(4)
<223> OTHER INFORMATION: His or Gln
<220> FEATURE:
<221> NAME/KEY: MOD_RES
<222> LOCATION: (6)..(6)
<223> OTHER INFORMATION: Gly or Val
<220> FEATURE:
<221> NAME/KEY: MOD_RES
<222> LOCATION: (9)..(9)
<223> OTHER INFORMATION: Asp, Leu, Arg, Ser or Trp
<220> FEATURE:
<221> NAME/KEY: MOD_RES
<222> LOCATION: (14)..(14)
<223> OTHER INFORMATION: Met or Val

```
<400> SEQUENCE: 210

Lys Xaa Ser Xaa Ser Xaa Asp Tyr Xaa Gly Asp Ser Tyr Xaa Ser
1               5                   10                  15

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asn or Tyr
<220> FEATURE:
<221> NAME/KEY: MOD_RES
<222> LOCATION: (5)..(5)
<223> OTHER INFORMATION: Leu, Arg or Tyr
<220> FEATURE:
<221> NAME/KEY: MOD_RES
<222> LOCATION: (7)..(7)
<223> OTHER INFORMATION: Gln or Ser

<400> SEQUENCE: 211

Gly Ala Ser Xaa Xaa Glu Xaa
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asp or Glu
<220> FEATURE:
<221> NAME/KEY: MOD_RES
<222> LOCATION: (8)..(8)
<223> OTHER INFORMATION: Phe or Tyr

<400> SEQUENCE: 212

Gln Gln Asn Asn Glu Xaa Pro Xaa Thr
1               5

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: His or Val
<220> FEATURE:
<221> NAME/KEY: MOD_RES
<222> LOCATION: (3)..(3)
<223> OTHER INFORMATION: Arg or Thr
<220> FEATURE:
<221> NAME/KEY: MOD_RES
<222> LOCATION: (4)..(4)
<223> OTHER INFORMATION: Phe, Gly, Arg or Ser
<220> FEATURE:
<221> NAME/KEY: MOD_RES
<222> LOCATION: (5)..(5)
<223> OTHER INFORMATION: Asp, Gly, Arg or Thr
<220> FEATURE:
<221> NAME/KEY: MOD_RES
```

```
<222> LOCATION: (9)..(9)
<223> OTHER INFORMATION: Met or Tyr

<400> SEQUENCE: 213

Gly Xaa Xaa Xaa Xaa Thr Tyr Gly Xaa Ser
1               5                   10

<210> SEQ ID NO 214
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ile, Met, Thr or Trp
<220> FEATURE:
<221> NAME/KEY: MOD_RES
<222> LOCATION: (6)..(6)
<223> OTHER INFORMATION: His or Arg
<220> FEATURE:
<221> NAME/KEY: MOD_RES
<222> LOCATION: (12)..(12)
<223> OTHER INFORMATION: Ile, Met, Thr or Tyr
<220> FEATURE:
<221> NAME/KEY: MOD_RES
<222> LOCATION: (14)..(14)
<223> OTHER INFORMATION: Asp or His
<220> FEATURE:
<221> NAME/KEY: MOD_RES
<222> LOCATION: (15)..(15)
<223> OTHER INFORMATION: Asp, Met or Thr
<220> FEATURE:
<221> NAME/KEY: MOD_RES
<222> LOCATION: (16)..(16)
<223> OTHER INFORMATION: Phe or Tyr
<220> FEATURE:
<221> NAME/KEY: MOD_RES
<222> LOCATION: (17)..(17)
<223> OTHER INFORMATION: Lys or Ser
<220> FEATURE:
<221> NAME/KEY: MOD_RES
<222> LOCATION: (18)..(18)
<223> OTHER INFORMATION: Gly or Arg

<400> SEQUENCE: 214

Gly Trp Ile Asn Xaa Xaa Ser Gly Val Pro Thr Xaa Ala Xaa Xaa Xaa
1               5                   10                  15

Xaa Xaa

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asn or Arg
<220> FEATURE:
<221> NAME/KEY: MOD_RES
<222> LOCATION: (6)..(6)
<223> OTHER INFORMATION: Arg, Cys, His, Ser or Tyr
<220> FEATURE:
<221> NAME/KEY: MOD_RES
<222> LOCATION: (10)..(10)
<223> OTHER INFORMATION: Ala or Tyr

<400> SEQUENCE: 215

Ala Xaa Leu Gly Ser Xaa Ala Val Asp Xaa
```

```
1               5                   10
```

<210> SEQ ID NO 216
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Val

<400> SEQUENCE: 216

```
Glu Xaa Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 217
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ile, Met or Val

<400> SEQUENCE: 217

```
Trp Val Arg Gln Ala Pro Gly Lys Gly Leu Glu Trp Xaa
1               5                   10
```

<210> SEQ ID NO 218
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Phe or Ile
<220> FEATURE:
<221> NAME/KEY: MOD_RES
<222> LOCATION: (6)..(6)
<223> OTHER INFORMATION: Leu or Arg
<220> FEATURE:
<221> NAME/KEY: MOD_RES
<222> LOCATION: (8)..(8)
<223> OTHER INFORMATION: Asn or Thr
<220> FEATURE:
<221> NAME/KEY: MOD_RES
<222> LOCATION: (10)..(10)
<223> OTHER INFORMATION: Ala, Glu, Lys or Thr
<220> FEATURE:
<221> NAME/KEY: MOD_RES
<222> LOCATION: (11)..(11)
<223> OTHER INFORMATION: Asn or Ser
<220> FEATURE:
<221> NAME/KEY: MOD_RES
<222> LOCATION: (13)..(13)
<223> OTHER INFORMATION: Ala, Leu, Met, Thr or Val
<220> FEATURE:
<221> NAME/KEY: MOD_RES
<222> LOCATION: (29)..(29)
<223> OTHER INFORMATION: Phe or Tyr

<400> SEQUENCE: 218

```
Arg Phe Thr Xaa Ser Xaa Asp Xaa Ser Xaa Xaa Thr Xaa Tyr Leu Gln
1               5                   10                  15

Met Asn Ser Leu Arg Ala Glu Asp Thr Ala Val Tyr Xaa Cys Ala Arg
            20                  25                  30
```

<210> SEQ ID NO 219
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

```
Trp Gly Gln Gly Thr Leu Val Thr Val Ser Ser
1               5                   10
```

<210> SEQ ID NO 220
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Leu or Arg
<220> FEATURE:
<221> NAME/KEY: MOD_RES
<222> LOCATION: (13)..(13)
<223> OTHER INFORMATION: Ala, Leu, Met, Thr or Val

<400> SEQUENCE: 220

```
Arg Phe Thr Ile Ser Xaa Asp Asn Ser Lys Asn Thr Xaa Tyr Leu Gln
1               5                   10                  15

Met Asn Ser Leu Arg Ala Glu Asp Thr Ala Val Tyr Tyr Cys Ala Arg
            20                  25                  30
```

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

```
Phe Gly Gln Gly Thr Lys Val Glu Ile Lys
1               5                   10
```

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Gln, Arg, Ser or Thr
<220> FEATURE:
<221> NAME/KEY: MOD_RES
<222> LOCATION: (2)..(2)
<223> OTHER INFORMATION: Pro, Thr or Trp
<220> FEATURE:
<221> NAME/KEY: MOD_RES
<222> LOCATION: (3)..(3)
<223> OTHER INFORMATION: His or Ser
<220> FEATURE:

```
<221> NAME/KEY: MOD_RES
<222> LOCATION: (4)..(4)
<223> OTHER INFORMATION: Asp or Gln
<220> FEATURE:
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (6)..(6)
<223> OTHER INFORMATION: Leu or Val
<220> FEATURE:
<221> NAME/KEY: MOD_RES
<222> LOCATION: (8)..(8)
<223> OTHER INFORMATION: His or Pro
<220> FEATURE:
<221> NAME/KEY: MOD_RES
<222> LOCATION: (9)..(9)
<223> OTHER INFORMATION: Ile, Leu, Pro, Thr or Tyr
<220> FEATURE:
<221> NAME/KEY: MOD_RES
<222> LOCATION: (10)..(10)
<223> OTHER INFORMATION: Asn, Gln or Ser
<220> FEATURE:
<221> NAME/KEY: MOD_RES
<222> LOCATION: (11)..(11)
<223> OTHER INFORMATION: Ala, Gly or Ser
<220> FEATURE:
<221> NAME/KEY: MOD_RES
<222> LOCATION: (16)..(16)
<223> OTHER INFORMATION: Gly or His

<400> SEQUENCE: 222

Xaa Xaa Xaa Xaa Xaa Xaa Val Xaa Xaa Xaa Xaa Ile Thr Tyr Leu Xaa
1               5                   10                  15

<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp or Arg
<220> FEATURE:
<221> NAME/KEY: MOD_RES
<222> LOCATION: (6)..(6)
<223> OTHER INFORMATION: Ala, Gly, Phe, Ile or Thr

<400> SEQUENCE: 223

Arg Val Ser Asn Xaa Xaa Ser
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, Gly, Ile, Lys, Leu, Asn, Ser, Thr or Val
<220> FEATURE:
<221> NAME/KEY: MOD_RES
<222> LOCATION: (4)..(4)
<223> OTHER INFORMATION: Cys or Thr
<220> FEATURE:
<221> NAME/KEY: MOD_RES
<222> LOCATION: (5)..(5)
<223> OTHER INFORMATION: Phe or His
```

```
<400> SEQUENCE: 224

Xaa Gln Ser Xaa Xaa Val Pro Leu Thr
1               5

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asn or Thr
<220> FEATURE:
<221> NAME/KEY: MOD_RES
<222> LOCATION: (4)..(4)
<223> OTHER INFORMATION: Phe or Val
<220> FEATURE:
<221> NAME/KEY: MOD_RES
<222> LOCATION: (5)..(5)
<223> OTHER INFORMATION: Ile, Met, Arg or Ser
<220> FEATURE:
<221> NAME/KEY: MOD_RES
<222> LOCATION: (7)..(7)
<223> OTHER INFORMATION: Tyr, Gln or Lys
<220> FEATURE:
<221> NAME/KEY: MOD_RES
<222> LOCATION: (9)..(9)
<223> OTHER INFORMATION: Ile or Met

<400> SEQUENCE: 225

Gly Tyr Xaa Xaa Xaa Asp Xaa Tyr Xaa Asn
1               5                   10

<210> SEQ ID NO 226
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Leu, Asn or Pro
<220> FEATURE:
<221> NAME/KEY: MOD_RES
<222> LOCATION: (6)..(6)
<223> OTHER INFORMATION: Asp, Leu or Arg
<220> FEATURE:
<221> NAME/KEY: MOD_RES
<222> LOCATION: (7)..(7)
<223> OTHER INFORMATION: Gly, Lys, Asn, Arg, Ser or Tyr
<220> FEATURE:
<221> NAME/KEY: MOD_RES
<222> LOCATION: (8)..(8)
<223> OTHER INFORMATION: Gly or Ser
<220> FEATURE:
<221> NAME/KEY: MOD_RES
<222> LOCATION: (9)..(9)
<223> OTHER INFORMATION: Gly, Ile, Lys, Arg, Ser, Thr or Val
<220> FEATURE:
<221> NAME/KEY: MOD_RES
<222> LOCATION: (10)..(10)
<223> OTHER INFORMATION: Gly, Arg or Thr
<220> FEATURE:
<221> NAME/KEY: MOD_RES
<222> LOCATION: (12)..(12)
<223> OTHER INFORMATION: Ile, Leu, Val or Tyr
<220> FEATURE:
<221> NAME/KEY: MOD_RES
<222> LOCATION: (13)..(13)
<223> OTHER INFORMATION: Asn or Ser
<220> FEATURE:
```

```
<221> NAME/KEY: MOD_RES
<222> LOCATION: (14)..(14)
<223> OTHER INFORMATION: Ala, Asn or Gln
<220> FEATURE:
<221> NAME/KEY: MOD_RES
<222> LOCATION: (15)..(15)
<223> OTHER INFORMATION: Lys or Val
<220> FEATURE:
<221> NAME/KEY: MOD_RES
<222> LOCATION: (16)..(16)
<223> OTHER INFORMATION: Phe or Gln
<220> FEATURE:
<221> NAME/KEY: MOD_RES
<222> LOCATION: (17)..(17)
<223> OTHER INFORMATION: Lys or Thr
<220> FEATURE:
<221> NAME/KEY: MOD_RES
<222> LOCATION: (18)..(18)
<223> OTHER INFORMATION: Gly, His, Arg or Ser

<400> SEQUENCE: 226

Gly Asp Ile Asn Xaa Xaa Xaa Xaa Xaa Xaa His Xaa Xaa Xaa Xaa Xaa
1               5                   10                  15

Xaa Xaa

<210> SEQ ID NO 227
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, Asn or Thr
<220> FEATURE:
<221> NAME/KEY: MOD_RES
<222> LOCATION: (8)..(8)
<223> OTHER INFORMATION: Asp or Pro
<220> FEATURE:
<221> NAME/KEY: MOD_RES
<222> LOCATION: (14)..(14)
<223> OTHER INFORMATION: Met or Trp

<400> SEQUENCE: 227

Xaa Arg Glu Gly Val Tyr His Xaa Tyr Asp Asp Tyr Ala Xaa Asp Tyr
1               5                   10                  15

<210> SEQ ID NO 228
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ile or Val

<400> SEQUENCE: 228

Trp Val Arg Gln Ala Pro Gly Lys Gly Leu Glu Trp Xaa
1               5                   10

<210> SEQ ID NO 229
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (2)..(2)
<223> OTHER INFORMATION: Phe or Val
<220> FEATURE:
<221> NAME/KEY: MOD_RES
<222> LOCATION: (4)..(4)
<223> OTHER INFORMATION: Ile or Leu
<220> FEATURE:
<221> NAME/KEY: MOD_RES
<222> LOCATION: (6)..(6)
<223> OTHER INFORMATION: Leu, Arg or Val
<220> FEATURE:
<221> NAME/KEY: MOD_RES
<222> LOCATION: (8)..(8)
<223> OTHER INFORMATION: Lys or Asn
<220> FEATURE:
<221> NAME/KEY: MOD_RES
<222> LOCATION: (10)..(10)
<223> OTHER INFORMATION: Lys, Asn, Arg or Ser
<220> FEATURE:
<221> NAME/KEY: MOD_RES
<222> LOCATION: (11)..(11)
<223> OTHER INFORMATION: Asn or Ser
<220> FEATURE:
<221> NAME/KEY: MOD_RES
<222> LOCATION: (13)..(13)
<223> OTHER INFORMATION: Ala, Leu or Val
<220> FEATURE:
<221> NAME/KEY: MOD_RES
<222> LOCATION: (15)..(15)
<223> OTHER INFORMATION: Leu or Met

<400> SEQUENCE: 229

Arg Xaa Thr Xaa Ser Xaa Asp Xaa Ser Xaa Xaa Thr Xaa Tyr Xaa Gln
 1               5                  10                  15

Met Asn Ser Leu Arg Ala Glu Asp Thr Ala Val Tyr Tyr Cys
            20                  25                  30

<210> SEQ ID NO 230
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Asn or Lys
<220> FEATURE:
<221> NAME/KEY: MOD_RES
<222> LOCATION: (13)..(13)
<223> OTHER INFORMATION: Ala, Leu or Val

<400> SEQUENCE: 230

Arg Phe Thr Ile Ser Arg Asp Xaa Ser Lys Asn Thr Xaa Tyr Leu Gln
 1               5                  10                  15

Met Asn Ser Leu Arg Ala Glu Asp Thr Ala Val Tyr Tyr Cys Ala Arg
            20                  25                  30

<210> SEQ ID NO 231
<211> LENGTH: 30
<212> TYPE: PRT
<213> ORGANISM: Homo sapiens

<400> SEQUENCE: 231

Arg Phe Thr Ile Ser Ala Asp Ser Ser Lys Asn Thr Ala Tyr Leu Gln
 1               5                  10                  15

Met Asn Ser Leu Arg Ala Glu Asp Thr Ala Val Tyr Tyr Cys
            20                  25                  30
```

-continued

```
<210> SEQ ID NO 232
<211> LENGTH: 6
<212> TYPE: DNA
<213> ORGANISM: Unknown
<220> FEATURE:
<223> OTHER INFORMATION: Description of Unknown: Eukaryotic sequence
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: misc_feature
<222> LOCATION: (2)..(2)
<223> OTHER INFORMATION: n is a, c, g, or t

<400> SEQUENCE: 232 cncaat                                                                      6

<210> SEQ ID NO 233
<211> LENGTH: 6
<212> TYPE: DNA
<213> ORGANISM: Unknown
<220> FEATURE:
<223> OTHER INFORMATION: Description of Unknown: Eukaryotic sequence

<400> SEQUENCE: 233 aataaa                                                                      6

<210> SEQ ID NO 234
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 234

Lys Ala Ser Gln Ser Val Asp Tyr Ser Gly Asp Ser Tyr Met Ser
1               5                   10                  15

<210> SEQ ID NO 235
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 235

Gly Ala Ser Tyr Arg Glu Ser
1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 236

Gln Gln Asn Asn Glu Glu Pro Tyr Thr
1               5

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 237

Ala Arg Leu Gly Ser Tyr Ala Val Asp Tyr
1               5                   10

<210> SEQ ID NO 238
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 238

Glu Ile Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 239
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 239

Trp Val Arg Gln Ala Pro Gly Lys Gly Leu Glu Trp Met
1               5                   10

<210> SEQ ID NO 240
<211> LENGTH: 32
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 240

Arg Phe Thr Ile Ser Leu Asp Asn Ser Lys Ser Thr Ala Tyr Leu Gln
1               5                   10                  15

Met Asn Ser Leu Arg Ala Glu Asp Thr Ala Val Tyr Phe Cys Ala Arg
            20                  25                  30

<210> SEQ ID NO 241
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 241

Arg Thr Ser Gln Ser Leu Val His Ile Asn Ala Ile Thr Tyr Leu His
1               5                   10                  15

<210> SEQ ID NO 242
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 242
```

```
Gly Asp Ile Asn Leu Asp Asn Ser Gly Thr His Tyr Asn Gln Lys Phe
1               5                   10                  15

Lys Gly

<210> SEQ ID NO 243
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 243

Arg Thr Ser Gln Ser Leu Val His Ile Ser Gly Ile Thr Tyr Leu His
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 244

Arg Thr Ser Gln Ser Leu Val His Ile Gln Gly Ile Thr Tyr Leu His
1               5                   10                  15

<210> SEQ ID NO 245
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 245

Arg Thr Ser Gln Ser Leu Val His Ile Asn Ser Ile Thr Tyr Leu His
1               5                   10                  15

<210> SEQ ID NO 246
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 246

Arg Thr Ser Gln Ser Leu Val His Ile Asn Ala Ile Thr Tyr Leu His
1               5                   10                  15

<210> SEQ ID NO 247
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 247

Gly Asp Ile Asn Leu Asp Asn Ser Gly Thr His Tyr Asn Gln Lys Phe
1               5                   10                  15

Lys Gly
```